(12) United States Patent
Smolke et al.

(10) Patent No.: US 8,865,667 B2
(45) Date of Patent: Oct. 21, 2014

(54) HIGHER-ORDER CELLULAR INFORMATION PROCESSING DEVICES

(75) Inventors: Christina D. Smolke, Pasadena, CA (US); Maung Nyan Win, San Gabriel, CA (US); Chase Beisel, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1051 days.

(21) Appl. No.: 12/283,614

(22) Filed: Sep. 12, 2008

(65) Prior Publication Data

US 2009/0098561 A1 Apr. 16, 2009

Related U.S. Application Data

(60) Provisional application No. 60/993,659, filed on Sep. 12, 2007.

(51) Int. Cl.
| | | |
|---|---|---|
| *A61K 48/00* | (2006.01) | |
| *C12N 15/11* | (2006.01) | |
| *C12N 15/115* | (2010.01) | |
| *B82Y 10/00* | (2011.01) | |
| *A61K 31/7105* | (2006.01) | |
| *G06N 3/00* | (2006.01) | |
| *C12N 15/113* | (2010.01) | |

(52) U.S. Cl.
CPC .......... *G06N 3/002* (2013.01); *C12N 2310/141* (2013.01); *C12N 15/111* (2013.01); *C12N 15/115* (2013.01); *B82Y 10/00* (2013.01); *A61K 31/7105* (2013.01); *C12N 15/113* (2013.01)
USPC ...................................................... 514/44 R

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. | |
| 4,426,330 A | 1/1984 | Sears | |
| 4,501,728 A | 2/1985 | Geho et al. | |
| 4,534,899 A | 8/1985 | Sears | |
| 4,737,323 A | 4/1988 | Martin et al. | |
| 4,837,028 A | 6/1989 | Allen et al. | |
| 4,897,355 A | 1/1990 | Eppstein et al. | |
| 5,013,556 A | 5/1991 | Woodle | |
| 5,013,830 A | 5/1991 | Ohtsuka et al. | |
| 5,093,246 A | 3/1992 | Cech | |
| 5,108,921 A | 4/1992 | Low | |
| 5,176,996 A | 1/1993 | Hogan | |
| 5,213,804 A | 5/1993 | Martin | |
| 5,214,135 A | 5/1993 | Srivastava et al. | |
| 5,227,170 A | 7/1993 | Sullivan | |
| 5,256,775 A | 10/1993 | Froehler | |
| 5,264,221 A | 11/1993 | Tagawa | |
| 5,264,423 A | 11/1993 | Cohen et al. | |
| 5,264,564 A | 11/1993 | Matteucci | |
| 5,270,163 A | 12/1993 | Gold | |
| 5,276,019 A | 1/1994 | Cohen et al. | |
| 5,354,844 A | 10/1994 | Beug | |
| 5,356,633 A | 10/1994 | Woodle | |
| 5,395,619 A | 3/1995 | Zalipsky | |
| 5,416,016 A | 5/1995 | Low | |
| 5,417,978 A | 5/1995 | Tari | |
| 5,459,127 A | 10/1995 | Felgner | |
| 5,462,854 A | 10/1995 | Coassin | |
| 5,469,854 A | 11/1995 | Unger | |
| 5,512,295 A | 4/1996 | Kornberg | |
| 5,521,291 A | 5/1996 | Curiel | |
| 5,525,719 A | 6/1996 | Srivastava et al. | |
| 5,527,528 A | 6/1996 | Allen | |
| 5,534,259 A | 7/1996 | Zalipsky | |
| 5,543,152 A | 8/1996 | Webb | |
| 5,543,158 A | 8/1996 | Gref | |
| 5,547,932 A | 8/1996 | Curiel | |
| 5,556,948 A | 9/1996 | Tagawa | |
| 5,580,575 A | 12/1996 | Unger | |
| 5,582,981 A | 12/1996 | Toole | |
| 5,583,020 A | 12/1996 | Sullivan | |
| 5,591,721 A | 1/1997 | Agrawal | |
| 5,595,756 A | 1/1997 | Bally | |
| 5,736,392 A | 4/1998 | Hawley-Nelson et al. | |
| 5,756,291 A | 5/1998 | Griffin | |
| 5,767,099 A | 6/1998 | Harris et al. | |

(Continued)

FOREIGN PATENT DOCUMENTS

| | | |
|---|---|---|
| AU | 2004206255 B2 | 8/2008 |
| WO | WO 88/04300 | 6/1988 |

(Continued)

OTHER PUBLICATIONS

Bayer et al. Nature Biotechnology 2005, vol. 23, pp. 337-343.*
U.S. Appl. No. 12/218,628, filed Mar. 26, 2009, Christina D. Smolke.
C. Mateus, S. V. Avery, Destabilized green fluorescent protein for monitoring dynamic changes in yeast gene expression with flow cytometry. Yeast 16, 1313-1323 (2000).
M. N. Win, C. D. Smolke, A modular and extensible RNA-based gene-regulatory platform for engineering cellular function. Proc Natl Acad Sci USA 104, 14283 (2007).
Y. Yokobayashi, R. Weiss, F. H. Arnold, Directed evolution of a genetic circuit. Proc Natl Acad Sci USA 99, 16587 (2002).
S. Basu, R. Mehreja, S. Thiberge, M. T. Chen, R. Weiss, Spatiotemporal control of gene expression with pulse-generating networks. Proc Natl Acad Sci USA 101: 6355 (2004).
E. Levine, Z. Zhang, T. Kuhlman, T. Hwa, Quantitative Characteristics of Gene Regulation by Small RNA. PLoS Biol 5: e229 (2007).

(Continued)

*Primary Examiner* — Tracy Vivlemore
(74) *Attorney, Agent, or Firm* — McCarter & English, LLP; Yu Lu; Jin Wang, Esq.

(57) ABSTRACT

The invention provides various signal processing devices for integrating two or more biological signals (e.g., the presence, absence or concentration of specific ligands, etc.) to generate a status output, or a response that modulates one or more biological activities based on the status of the biological signals. The various described signal processing/integration mechanisms may be combined with one another to provide the device with more flexibility in integrating high-order cellular information. The signal processing devices of the invention have many uses in various biological systems, including gene expression control or ligand-concentration sensing.

26 Claims, 34 Drawing Sheets

(56) References Cited

U.S. PATENT DOCUMENTS

| | | | |
|---|---|---|---|
| 5,777,153 | A | 7/1998 | Lin et al. |
| 5,780,053 | A | 7/1998 | Ashley et al. |
| 5,830,430 | A | 11/1998 | Unger et al. |
| 5,830,653 | A | 11/1998 | Froehler et al. |
| 5,851,548 | A | 12/1998 | Dattagupta et al. |
| 5,855,910 | A | 1/1999 | Ashley et al. |
| 6,458,559 | B1 | 10/2002 | Shi et al. |
| 2002/0106648 | A1 | 8/2002 | Lizardi et al. |
| 2002/0150996 | A1 | 10/2002 | Nilsen-Hamilton |
| 2002/0166132 | A1 | 11/2002 | Scherman et al. |
| 2003/0105051 | A1 | 6/2003 | McSwiggen |
| 2003/0124595 | A1 | 7/2003 | Lizardi |
| 2003/0157030 | A1 | 8/2003 | Davis et al. |
| 2004/0063654 | A1 | 4/2004 | Davis |
| 2004/0072785 | A1 | 4/2004 | Wolff et al. |
| 2004/0086884 | A1 | 5/2004 | Beach |
| 2004/0162235 | A1 | 8/2004 | Trubetskoy et al. |
| 2004/0204377 | A1 | 10/2004 | Rana et al. |
| 2005/0003362 | A1 | 1/2005 | Crylov et al. |
| 2005/0026286 | A1 | 2/2005 | Chi et al. |
| 2005/0037496 | A1 | 2/2005 | Rozema et al. |
| 2005/0042227 | A1 | 2/2005 | Zankel et al. |
| 2005/0048647 | A1 | 3/2005 | Taira et al. |
| 2005/0064595 | A1 | 3/2005 | MacLachlan et al. |
| 2005/0265957 | A1 | 12/2005 | Monahan et al. |
| 2006/0008910 | A1 | 1/2006 | MacLachlan et al. |
| 2006/0088864 | A1 | 4/2006 | Smolke et al. |
| 2006/0178327 | A1 | 8/2006 | Yeung et al. |
| 2006/0240093 | A1 | 10/2006 | MacLachlan et al. |
| 2007/0077571 | A1* | 4/2007 | Ellington et al. ............ 435/6 |
| 2007/0083947 | A1 | 4/2007 | Huang et al. |
| 2007/0231392 | A1 | 10/2007 | Wagner et al. |
| 2008/0038296 | A1 | 2/2008 | Brahmbhatt et al. |
| 2008/0107694 | A1 | 5/2008 | Trogden et al. |
| 2008/0112916 | A1 | 5/2008 | Wagner et al. |
| 2008/0152661 | A1 | 6/2008 | Rozema et al. |

FOREIGN PATENT DOCUMENTS

| | | |
|---|---|---|
| WO | WO 88/09810 | 12/1988 |
| WO | WO 89/10134 | 11/1989 |
| WO | WO 90/11364 | 10/1990 |
| WO | WO 90/14074 A1 | 3/1991 |
| WO | WO 91/16024 A1 | 10/1991 |
| WO | WO 91/17424 A1 | 11/1991 |
| WO | WO 92/03568 A1 | 3/1992 |
| WO | WO 97/42317 | 11/1997 |
| WO | WO 98/13526 A1 | 4/1998 |
| WO | WO 9904800 | 2/1999 |
| WO | WO 99/27133 | 6/1999 |
| WO | WO 99/54506 | 10/1999 |
| WO | WO 00/20040 | 4/2000 |
| WO | WO 2004033653 A2 | 4/2004 |
| WO | WO 2004/048545 A2 | 6/2004 |
| WO | WO 2004/065601 A2 | 8/2004 |
| WO | WO 2005001039 A2 | 1/2005 |
| WO | WO 2006086669 | 8/2006 |
| WO | WO 2007/089607 A2 | 8/2007 |
| WO | WO 2008/036825 A2 | 3/2008 |

OTHER PUBLICATIONS

S. S. Hebert et al., Loss of microRNA cluster miR-29a/b-1 in sporadic Alzheimer's disease correlates with increased BACE1/β-secretase expression. Proc Natl Acad Sci USA 105: 6415 (2008).

G. A. Calin et al., MiR-15a and miR-16-1 cluster functions in human leukemia. Proc Natl Acad Sci USA 105: 5166 (2008).

A. Ventura et al., Targeted Deletion Reveals Essential and Overlapping Functions of the miR-17~92 Family of miRNA Clusters. Cell 132: 875-886 (2008).

R. Welz, R. R. Breaker, Ligand binding and gene control characteristics of tandem riboswitches in Bacillus anthracis. RNA 13: 573 (2007).

G. A. Soukup, G. A. Emilsson, R. R. Breaker, Altering molecular recognition of RNA aptamers by allosteric selection. J Mol Biol 298: 623 (2000).

D. A. Rodionov, I. Dubchak, A. Arkin, E. Alm, M. S. Gelfand, Reconstruction of regulatory and metabolic pathways in metal-reducing δ-proteobacteria. Genome Biol 5: R90 (2004).

K. Rinaudo et al., A universal RNAi-based logic evaluator that operates in mammalian cells. Nat Biotechnol 25: 795 (2007).

T. L. Deans, C. R. Cantor, 1. J. Collins, A Tunable Genetic Switch Based on RNAi and Repressor Proteins for Regulating Gene Expression in Mammalian Cells. Cell 130: 363 (2007).

Koch, The metabolism of methylpurines by *Escherichia coli*: I. tracer studies. J. Biol Chem 219: 181-188, (1956).

Khosla et al., Metabolic engineering for drug discovery and development. Nat Rev Drug Discov 2: 1019-1025, (2003).

Kobayashi et al., Programmable cells: Interfacing natural and engineered gene networks. Proc Natl Acad Sci USA 101: 8414-8419, (2004).

Berens et al., A tetracycline-binding RNA aptamer. Bioorg Med Chem 9: 2549-2556, (2001).

Nagai et al., A variant of yellow fluorescent protein with fast and efficient maturation for cell-biological applications. Nat Biotechnol 20: 87-90, (2002).

Ellington et al., In vitro selection of RNA molecules that bind specific ligands. Nature 346: 818-22 (1990).

Tuerk et al., Systematic evolution of ligands by exponential enrichment: RNA ligands to bacteriophage T4 DNA polymerase. Science 249: 505-10 (1990).

Batzer et al., Enhanced evolutionar PCR using oligonucleotides with inosine at the 3'-terminus. Nucleic Acid Res.19: 5081 (1991).

Ohtsuka et al., An alternative approach to deoxyoligonucleotides as hybridization probes by insertion of deoxyinosine at ambiguous codon positions. J Biol. Chem. 260: 2605-2608 (1985).

Rossolini et al., Use of deoxyinosine-containing primers vs degenerate primers for polymerase chain reaction based on ambiguous sequence information. Mol. Cell. Probes 8: 91-98 (1994).

Werstuck and Green, Controlling Gene Expression in Living Cells Through Small Molecule-RNA Interactions. Science 282: 296-298 (1998).

Famulok, Oligonucleotide aptamers that recognize small molecules. Curr. Opin. Struct. Biol. 9: 324-9 (1999).

Lorsch and Szostak, In vitro selection of RNA aptamers specific for cyanocobalamin. Biochemistry, 33: 973 (1994).

Mannironi et al., In Vitro Selection of Dopamine RNA Ligands. Biochemistry 36: 9726 (1997).

Blind, Cytoplasmic RNA modulators of an inside-out signal-transduction cascade. Proc. Natl. Acad. Sci. USA 96: 3606-3610 (1999).

Huizenga and Szostak, A DNA Aptamer That Binds Adenosine and ATP. Biochemistry, 34: 656-665 (1995).

Letsinger et al., Cholesteryl-conjugated oligonucleotides: synthesis, properties, and activity as inhibitors of replication of human immunodeficiency virus in cell culture. Proc Natl Acad Sci. USA 86: 6553-6556 (1989).

Lemaitre et al., Specific antiviral activity of a poly(L-lysine)-conjugated oligodeoxyribonucleotide sequence complementary to vesicular stomatitis virus N protein mRNA initiation site. Proc Natl Acad Sci. USA 84: 648-652 (1987).

Krol et al., Modulation of eukaryotic gene expression by complementary RNA or DNA sequences. BioTechniques 6: 958-976 (1988).

Zon, Oligonucleotide analogues as potential chemotherapeutic agents. Pharm. Res. 5: 539-549 (1988).

Perry-O'Keefe et al. Peptide nucleic acid pre-gel hybridization: An alternative to Southern hybridization. Proc. Natl. Acad. Sci. USA 93: 14670 (1996).

Eglom et al. PNA hybridizes to complementary oligonucleotides obeying the Watson-Crick hydrogen-bonding rules. Nature 365: 566 (1993).

Gautier et al., Alpha-DNA. IV: Alpha-anomeric and beta-anomeric tetrathymidylates covalently linked to intercalating oxazolopyridocarbazole. Synthesis, physicochemical properties and poly (rA) binding. Nucl. Acids Res. 15: 6625-6641 (1987).

(56) References Cited

OTHER PUBLICATIONS

Inoue et al., Synthesis and hybridization studies on two complementary nona(2'-O-methyl)ribonucleotides. Nucl. Acids Res. 15: 6131-6148 (1987).
Inoue et al., Sequence-dependent hydrolysis of RNA using modified oligonucleotide splints and RNase H., FEBS Lett. 215: 327-330 (1987).
Brennecke et al., Towards a complete description of the microRNA complement of animal genomes. Genome Biology 4: 228 (2003).
Kim et al., Small RNAs: classification, biogenesis, and function. Mol. Cells 19:1-15 (2005).
Berge et al., "Pharmaceutical Salts," J. of Pharm Sci., 66:1-19 (1977).
C. C. Guet, M. B. Elowitz, W. Hsing, S. Leibler, Combinatorial synthesis of genetic networks, Science 296: 1466 (2002).
B. P. Kramer, C. Fischer, M. Fussenegger, BioLogic gates enable logical transcription control in mammalian cells. Biotechnol Bioeng 87: 478 (2004).
R. S. Cox, 3rd, M. G. Surette, M. B. Elowitz, Programming gene expression with combinatorial promoters. Mol Syst Biol 3: 145 (2007).
J. C. Anderson, C. A. Voigt, A. P. Arkin, Environmental signal integration by a modular AND gate. Mol Syst Biol 3: 133 (2007).
G. Seelig, D. Soloveichik, D. Y. Zhang, E. Winfree, Science 314: 1585 (2006).
Y. Benenson, B. Gil, U. Ben-Dor, R. Adar, E. Shapiro, An autonomous molecular computer for logical control of gene expression. Nature 429: 423 (2004).
R. M. Dirks, N. A. Pierce, Triggered amplification by hybridization chain reaction. Proc Natl Acad Sci USA 101: 15275 (2004).
M. N. Stojanovic, D. Stefanovic, A deoxyribozyme-based molecular automaton Nat Biotechnol 21: 1069 (2003).
R. Penchovsky, R. R. Breaker, Computational design and experimental validation of oligonucleotide-sensing allosteric ribozymes Nat Biotechnol 23: 1424 (2005).
R. R. Breaker, Engineered allosteric ribozymes as biosensor components. Curr Opin Biotechnol 13:31 (2002).
M. P. Robertson, A. D. Ellington, In vitro selection of an allosteric ribozyme that transduces analytes to amplicons Nat Biotechnol 17: 62 (1999).
F. J. Isaacs, D. J. Dwyer, J. J. Collins, RNA synthetic biology Nat Biotechnol 24: 545 (2006).
B. Suess, J. E. Weigand, Engineered riboswitches: overview, problems and trends. RNA Biol 5: 24 (2008).
B. D. Brown et al., Endogenous microRNA can be broadly exploited to regulate transgene expression according to tissue, lineage and differentiation state Nat Biotechnol 25: 1457 (2007).
M. Parisien, F. Major, The MC-Fold and MC-Sym pipeline infers RNA structure from sequence data Nature 452: 51 (2008).
D. H. Mathews, D. H. Turner, Prediction of RNA secondary structure by free energy minimization. Curr Opin Struct Biol 16: 270 (2006).
M. N. Win, C. D. Smolke, A modular and extensible RNA-based gene-regulatory platform for engineering cellular function. Proc Natl Acad Sci USA 104: 14283 (2007).
T. Hermann, D. J. Patel, Adaptive recognition by nucleic acid aptamers. Science 287: 820 (2000).
A. Khvorova, A. Lescoute, E. Westhof, S. D. Jayasena, Sequence elements outside the hammerhead ribozyme catalytic core enable intracellular activity. Nat Struct Bioi 10: 708 (2003).
M. Mandal et al., A glycine-dependent riboswitch that uses cooperative binding to control gene expression. Science 306: 275 (2004).
N. Sudarsan et al., Tandem riboswitch architectures exhibit complex gene control functions. Science 314: 300 (2006).
R. Welz, R. R. Breaker, Select this articleLigand binding and gene control characteristics of tandem riboswitches in *Bacillus anthracis* RNA 13: 573 (2007).
M. T. Woodside et al., Nanomechanical measurements of the sequence-dependent folding landscapes of single nucleic acid hairpins Proc Natl Acad Sci USA 103: 6190 (2006).
Beisel et al., "Model-guided design of ligand-regulated RNAi for programmable control of gene expression," 2008 Molecular Systems Biology 4:224.
Chen et al., "Genetic control of mammalian T-cell proliferation with synthetic RNA regulatory systems." 2010 Proc. Natl. Acad. Sci. USA. 107: 8531-6.
Culler et al., "Functional selection and systematic analysis of intronic splicing elements identifies active sequence motifs and associated splicing factors." 2010 Nuc. Acids Res. 38: 5152-65.
Hoff et al., "In vivo fluorescent detection of Fe-S clusters coordinated by human GRX2." 2009 Chem. Biol. 16: 1299-308.
Smolke, "Building outside of the box: iGEM and the BioBricks Foundation." 2009 Nat. Biotech. 27:1099-102.
Smolke, "It's the DNA that counts." 2009 Science. 324: 1156-7.
Beisel et al., "Design principles for riboswitch function." 2009 PLoS Comp. Biol. 5: e1000363.
Win et al., "Frameworks for programming biological function through RNA parts and devices." 2009 Chem. Biol. 16: 298-310.
Bayer et al., "Synthetic control of a fitness tradeoff in yeast nitrogen metabolism." 2009 J. Biol. Eng. 3: 1.
Hoff et al., "Fluorescence detection of a protein-bound 2Fe2S cluster." 2009 Chembiochem. 10: 667-70.
Hawkins et al., "Production of benzylisoquinoline alkaloids in *Saccharomyces cerevisiae*." 2008 Nat. Chem. Biol. 4: 564-73.
Benenson, "Small hairpin RNA as a small molecule sensor." 2008 Mol. Sys. Biol. 4: 227.
Keasling, "From yeast to alkaloids." 2008 Nat. Chem. Biol. 4: 524-5.
Win et al., "Higher-order cellular information processing with synthetic RNA devices." 2008 Science. 322: 456-60.
Shapiro et al., "RNA computing in a living cell." 2008 Science. 322: 387-8.
Baker et al., "Engineering life: building a Fab for biology." 2006 Scientific American. 294: 44-51.
Win et al., "Codeine-binding RNA aptamers and rapid determination of their binding constants using a direct coupling surface plasmon resonance assay." 2006 Nuc. Acids Res. 34: 5670-82.
Pfleger et al., "Combinatorial engineering of intergenic regions in operons tunes expression of multiple genes." 2006 Nat. Biotech. 24: 1027-32.
Hawkins et al., "The regulatory roles of the galactose permease and kinase in the induction response of the GAL network in *Saccharomyces cerevisiae*." 2006 J. Biol. Chem. 281: 13485-92.
Isaacs et al., "Plug and play with RNA." 2005 Nat. Biotech. 23: 306-7.
Martin et al., "Redesigning cells for the production of complex organic molecules." 2002 ASM News 68: 336-43.
Smolke et al., "Effect of gene location, mRNA secondary structures, and Rnase sites on expression of two genes in an engineered operon." 2002 Biotech. Bioeng. 80: 762-76.
Smolke et al., "Effect of copy number and mRNA processing and stabilization on transcript and protein levels from an engineered dual-gene operon." 2002 Biotech. Bioeng. 78: 412-24.
Smolke et al., "Effects of transcription induction homogeneity and transcript stability on expression of two genes in a constructed operon." 2001 Appl. Micro. Biotech. 57: 689-96.
Smolke et al., "Controlling the metabolic flux through the carotenoid pathway using directed mRNA processing and stabilization." 2001 Met. Eng. 3: 313-21.
Buskirk et al., Engineering a Ligand-Dependent RNA Transcriptional Activator. 2004 Chemistry & Biology 11 :1157-1163.
Buskirk et al., In Vivo Evolution of an RNA-Based Transcriptional Activator. 2003 Chemistry & Biology 10:533-540.
Famulok , Bringing Picomolar Protein Detection Into Proximity. 2002 Nature Biotechnology 20:448-449.
Fredriksson et al., Protein Detection Using Proximity-Dependent DNA Litagation Assays. 2002 Nature Biotechnology 20:473-477.
Hesselberth et al., Simultaneous Detection of Diverse Analytes with an Aptazyme Ligase Array. 2003 Analytical Biochemistry 312:106-112.
Luzi et al., New Trends in Affinity Sensing: Aptamers for Ligand Binding. 2003 Trends in Analytical Chemistry 22:810-818.

(56) References Cited

OTHER PUBLICATIONS

Nutiu et al., Structure-Switching Signaling Aptamers: Transducing Molecular Recognition Into Fluorescence Signaling. 2004 Chem. Eur. J. 10:1868-1876.
Nutiu et al., Structure-Switching Signaling Aptamers. 2003 J. Am. Chem. Soc. 125:4771-4778.
Silverman, Rube Goldberg Goes (RIBO)Nuclear? Molecular Switches and Sensors Made From RNA. 2003 RNA 9:377-383.
Winkler et al., An mRNA Structure That Controls Gene Expression by Binding FMN. 2002 PNAS 99:15908-15913.
Winkler et al., Genetic Control by Metabolite-Binding Riboswitches. 2003 ChemBioChem 4:1024-1032.
Al-Douahji et al., The cyclin kinase inhibitor p21WAF1/C1P1 is required for glomerular hypertrophy in experimental diabetic nephropathy. 1999 Kidnev Int 56:1691-1699.
Banerjee et al., Control of developmental timing by small temporal RNAs: a paradigm for RNA-mediated reaulation of gene expression. 2002 Bioessavs 24:119-129.
Barrick et al., New RNA motifs suggest an expanded scope for riboswitches in bacterial genetic control. 2004 Proc Natl Acad Sci USA 101:6421-6426.
Bartel, MicroRNAs: genomics, biogenesis, mechanism, and function. 2004 Cell 116:281-297.
Been and Cech, One binding site determines sequence specificity of Tetrahymena pre-rRNA self-splicing, trans-splicing, and RNA enzyme activity. 1986 Cell 47:207-216.
Benoist et al., In vivo sequence requirements of the SV40 early promotor region. 1981 Nature 290:304-310.
Brinster et al., Regulation of metallothionein-thymidine kinase fusion plasmids injected into mouse eggs. 1982 Nature 296:39-42.
Brummelkamp et al., A system for stable expression of short interfering RNAs in mammalian cells. 2002 Science 296:550-553.
Buskirk et al., Engineering a ligand-dependent RNA transcriptional activator. 2004 Chem Biol 11:1157-1163.
Caplen et al., Specific inhibition of gene expression by small double-stranded RNAs in invertebrate and vertebrate systems. 2001 Proc Natl Acad Sci USA 98:9742-9747.
Caponigro et al., A small segment of the MATa1 transcript promotes mRNA decay in Saccharomyces cerevisiae: a stimulatory role for rare codons. 1993 Mol Cell Biol 13:5141-5148.
Chen et al., Synthesis of oligodeoxyribonucleotide N3' -> P5' phosphoramidates. 1995 Nucleic Acids Res 23:2661-2668.
Cox et al., Automated selection of aptamers against protein targets translated in vitro: from gene to aptamer. 2002 Nucleic Acids Res 30:e108.
Dragun et al., Inhibition of intercellular adhesion molecule-1 with antisense deoxynucleotides prolonos renal isograft survival in the rat. 1998 Kidnev Int 54:2113-2122.
Dragun et al., ICAM-1 antisense oligodesoxynucleotides prevent reperfusion injury and enhance immediate graft function in renal transplantation. 1998 Kidnev Int 54:590-602.
Elbashir et al., Duplexes of 21-nucleotide RNAs mediate RNA interference in cultured mammalian cells. 2001 Nature 411:494-498.
Gardner et al., Inferring genetic networks and identifying compound mode of action via expression profiling. 2003 Science 301:102-105.
Gil et al., Induction of apoptosis by the dsRNA-dependent protein kinase (PKR): mechanism of action. 2000 Apoptosis 5:107-114.
Good, Diverse antisense mechanisms and applications. 2003 Cell Mol Life Sci 60:823-824.
Good, Translation repression by antisense sequences. 2003 Cell Mol Life Sci 60:854-861.
Gouda et al., Free energy calculations for theophylline binding to an RNA aptamer: Comparison of MM-PBSA and thermodynamic integration methods. 2003 Biopolymers 68:16-34.
Haller et al., Antisense oligonucleotides for ICAM-1 attenuate reperfusion injury and renal failure in the rat. 1996 Kidnev Int 50:473-480.
Hamm et al., Anti-idiotype RNA selected with an anti-nuclear export signal antibody is actively transported in oocytes and inhibits Rev- and cap-dependent RNA export. 1997 Proc Natl Acad Sci USA 94:12839-12844.
Haseloff et al., Simple RNA enzymes with new and highly specific endoribonuclease activities. 1988 Nature 334:585-591.
Heidenreich et al., RNase H-independent antisense activity of oligonucleotide N3' -> P5' phosphoramidates. 1997 Nucleic Acids Res 25:776-780.
Hesselberth et al., Simultaneous detection of diverse analytes with an aptazyme ligase array. 2003 Anal Biochem 312:106-112.
Hirschbein et al., 31P NMR spectroscopy in oligonucleotide research and development. 1997 Antisense Nucleic Acid Drug Dev 7:55-61.
Isaacs et al., Engineered riboregulators enable post-transcriptional control of gene expression. 2004 Nat Biotechnol 22:841-847.
Jhaveri et al., In vitro selection of signaling aptamers. 2000 Nat Biotechnol 18:1293-1297.
Jose et al., Cooperative binding of effectors by an allosteric ribozyme. 2001 Nucleic Acids Res 29:1631-1637.
Kertsburg et al., A versatile communication module for controlling RNA folding and catalysis. 2002 Nucleic Acids Res 30:4599-4606.
Kipshidze et al., "local delivery of c-myc neutrally charged antisense oligonucleotides with transport catheter inhibits myointimal hyperplasia and positively affects vascular remodeling in the rabbit balloon injury model." 2001 Catheter Cardiovasc Interv 54:247-256.
Kipshidze et al., Intramural coronary delivery of advanced antisense oligonucleotides reduces neointimal formation in the porcine stent restenosis model. 2002 JAm Coll Cardiol 39:1686-1691.
Koizumi et al., Allosteric selection of ribozymes that respond to the second messengers cGMP and cAMP. 1999 Nat Struct Biol 6:1062-1071.
Kramer et al., Role for antisense RNA in regulating circadian clock function in *Neurospora crassa*. 2003 Nature 421:948-952.
Kutryk et al., "local intracoronary administration of antisense oligonucleotide against c-myc for the prevention of in-stent restenosis: results of the randomized investigation by the Thoraxcenter of antisense DNA using local delivery and IVUS after coronary stenting (ITALICS) trial." 2002 J Am Coll Cardiol 39:281-287.
Kuwabara et al., Allosterically controllable ribozymes with biosensor functions. 2000 Curr Opin Chem Biol 4:669-677.
Kuwabara et al., Allosterically controllable maxizyme-mediated suppression of progression of leukemia in mice. 2001 Biomacromolecules 2:1220-1228.
Kuwabara et al., Allosterically controlled single-chained maxizymes with extremely high and soecific activity. 2001 Biomacromolecules 2:788-799.
Lavorana et al., In search of antisense. 2004 Trends Biochem Sci 29:88-94.
Lilley, The origins of RNA catalysis in ribozymes. 2003 Trends Biochem Sci 28:495-501.
Mandal et al., Adenine riboswitches and gene activation by disruption of a transcription terminator. 2004 Nat Struct Mol Biol 11:29-35.
Mathews et al., Incorporating chemical modification constraints into a dynamic programming algorithm for prediction of RNA secondary structure. 2004 Proc Natl Acad Sci USA 101:7287-7292.
McCaffrey et al., RNA interference in adult mice. 2002 Nature 418:38-39.
McManus et al., Gene silencing using micro-RNA desianed hairpins. 2002 RNA 8:842-850.
Nutiu et al., Structure-switching signaling aptamers. 2003 J Am Chem Soc 125:4771-4778.
Paddison et al., Stable suppression of gene expression by RNAi in mammalian cells. 2002 Proc Natl Acad Sci USA 99:1443-1448.
Paddison et al., Short hairpin RNAs (shRNAs) induce sequence-specific silencing in mammalian cells. 2002 Genes Dev 16:948-958.
Piganeau et al., In vitro selection of allosteric ribozymes: theory and experimental validation. 2001 J Mol Biol 312:1177-1190.
Robertson et al., Design and optimization of effector-activated ribozyme ligases. 2000 Nucleic Acids Res 28:1751-1759.
Roth et al., Selection in vitro of allosteric ribozymes. 2004 Methods Mol Biol 252:145-164.

(56) References Cited

OTHER PUBLICATIONS

Samarsky et al., A small nucleolar RNA:ribozyme hybrid cleaves a nucleolar RNA target in vivo with near-perfect efficiency. 1999 Proc Natl Acad Sci USA 96:6609-6614.
Sarver et al., Ribozymes as potential anti-HIV-1 therapeutic agents. 1990 Science 247:1222-1225.
Scherer et al., Recent applications of RNAi in mammalian systems. 2004 Curr Pharm Biotechnol 5:355-360.
Scherer et al., Approaches for the sequence-specific knockdown of Mrna. 2003 Nat Biotechnol 21:1457-1465.
Smolke et al., Coordinated, differential expression of two genes through directed mRNA cleavage and stabilization by secondary structures. 2000 Appl Environ Microbiol 66:5399-5405.
Soukup et al., Generating new ligand-binding RNAs by affinity maturation and disintegration of allosteric ribozymes. 2001 RNA 7:524-536.
Soukup et al., Design of allosteric hammerhead ribozymes activated by ligand-induced structure stabilization. 1999 Structure 7:783-791.
Stein et al., Oligodeoxynucleotides as inhibitors of gene expression: a review. 1988 Cancer Res 48:2659-2668.
Stojanovic et al., Modular aptameric sensors. 2004 J Am Chem Soc 126:9266-9270.
Sui et al., A DNA vector-based RNAi technology to suppress gene expression in mammalian cells. 2002 Proc Natl Acad Sci USA 99:5515-5520.
Taira et al., Construction of a novel RNA-transcript-trimming plasmid which can be used both in vitro in place of run-off and (G)-free transcriptions and in vivo as multi-sequences transcription vectors. 1991 Nucleic Acids Res 19:5125-5130.
Tang et al., Rational design of allosteric ribozymes. 1997 Chem Biol 4:453-459.
Vacek et al., Antisense-mediated redirection of mRNA splicing. 2003 Cell Mol Life Sci 60:825-833.
Wagner et al., Nucleotide sequence of the thymidine kinase gene of herpes simplex virus type 1. 1981 Proc Natl Acad Sci USA 78:1441-1445.
Wagner, Gene inhibition using antisense oligodeoxynucleotides. 1994 Nature 372:333-335.
Wang et al., A general approach for the use of oligonucleotide effectors to regulate the catalysis of RNA-cleaving ribozymes and DNAzymes. 2002 Nucleic Acids Res 30:1735-1742.
Wang et al., A general strategy for effector-mediated control of RNA-cleaving ribozymes and DNA enzymes. 2002 J Mol Biol 318:33-43.
Watkins et al., Metabolomics and biochemical profiling in drug discovery and development. 2002 Curr Opin Mol Ther 4:224-228.
Weiss et al., Antisense RNA gene therapy for studying and modulating biological processes. 1999 Cell Mol Life Sci 55:334-358.
Wilda et al., Killing of leukemic cells with a BCRIABL fusion gene by RNA interference I (RNAi). 2002 Oncogene 21:5716-5724.
Wilson et al., The interaction of intercalators and groove-binding agents with DNA triplehelical structures: the influence of ligand structure, DNA backbone modifications and sequence. 1994 J Mol Recognit 7:89-98.
Winkler et al., Control of gene expression by a natural metabolite-responsive ribozyme. 2004 Nature 428:281-286.
Winkler et al., Thiamine derivatives bind messenger RNAs directly to regulate bacterial gene expression. 2002 Nature 419:952-956.
Yamamoto et al., Identification of a functional promoter in the long terminal repeat of *Rous sarcoma virus*. 1980 Cell 22:787-797.
Yelin et al., Widespread occurrence of antisense transcription in the human genome. 2003 Nat Biotechnol 21:379-386.
Yen et al., Exogenous control of mammalian gene expression through modulation of RNA self-cleavage. 2004 Nature 431:471-476.
Yu et al., RNA interference by expression of short-interfering RNAs and hairpin RNAs in mammalian cells. 2002 Proc Natl Acad Sci USA 99:6047-6052.
Zaug et al., A labile phosphodiester bond at the ligation junction in a circular intervening sequence RNA. 1984 Science 224:574-578.
Zaug et al., The intervening sequence RNA of Tetrahymena is an enzyme. 1986 Science 231:470-475.
Zaug et al., The Tetrahymena ribozyme acts like an RNA restriction endonuclease. 1986 Nature 324:429-433.
Zimmermann et al., Interlocking structural motifs mediate molecular discrimination by a theophylline-binding RNA. 1997 Nat Struct Biol 4:644-649.
Zimmermann et al., Molecular interactions and metal binding in the theophylline-binding core of an RNA aptamer. 2000 RNA 6:659-667.
Vuyisich et al., Controlling protein activity with ligand-regulated RNA aptamers. 2002 Chemistry & Biology, 9:907-913.
Agrawal et al., RNA interference: biology, mechanism, and applications. 2003 Microbiology and Molecular Biology Reviews, 67:657-685.
Soukup et al., Nucleic acid molecular switches. 1999 Trends in Biotechnology 17:469-476.
Carmell et al., RNase III enzymes and the initiation of gene silencing. 2004 Nature Structural & Molecular Biology, 11:214-218.
An et al., Artificial control of gene expression in mammalian cells by modulating RNA interference through aptamer-small molecule interaction, 2006, RNA 12(5):710-716.
Bauer G. et al., Engineered riboswitches as novel tools in molecular biology, 2006, Journal of Biotechnology 124(1):4-11.
Berezovski et al., Nonequilibrium Capillary Electrophoresis of Equilibrium Mixtures: A Universal Tool for Development of Aptamers, 2005, J. Am. Chem. Soc. 127:3165-3171.
Davidson et al., Synthetic RNA circuits, 2007, Nature Chemical Biology 3(1):23-28.
Desai et al., Genetic screens and selections for small molecules based on a synthetic riboswitch that activates protein translation. 2004, Journal of the American Chemical Society 126:13247-13254.
Drabovich et al., Selection of Smart Aptamers by Equilibrium Capillary Electrophoresis of Eauilibrium Mixtures (ECEEM). 2005 J. Am. Chem. Soc. 127:11224-11225.
John J. Rossi, Targeted cleavage: Tuneable cis-cleaving ribozymes. 2007 PNAS 104(38):14881-14882.
Mendonsa et al., In Vito Evolution of Functional DNA Using Capillary Electrophoresis. 2004 J. Am. Chem. Soc. 126:20-21.
Mendonsa et al., In Vitro Selection of Aptamers with Affinity for Neuropeptide Y Using D Capillarv Electrophoresis. 2005 J. Am. Chem. Soc. 127:9382-9383.
Mendonsa et al., In Vitro Selection of High-Affinity DNA Ligands for Human IgE Using Capillary Electrophoresis. 2004 Anal. Chern. 76:5387-5392.
Smolke et al., Molecular Switches for Cellular Sensors. 2005 Engineering & Science 67(4):28-37.
Suess et al., A theophylline responsive riboswitch based on helix slipping contois gene expression in vivo. 2004 Nucleic Acids Research. 32(4):1610-1614.
Win et al., RNA as a Versatile and Powerful Platform for Engineering Genetic Regulartory Tools. 2007 Biotechnoloay and Genetic Engineering Reviews 24:311-346.
Berens et al., Synthetic riboregulators—an alternative means to control gene expression. 2005 Gene Therapy and Molecular Biology 9:417-422.
Stein et al., Physicochemical properties of phosphborothioate oligodeoxynucleotides. 1988 Nucl. Acids Res. 16:3209-3221.
Sarin et al., Inhibition of acquired immunodeficiency syndrome virus by oligodeoxynucleoside methylphosphonates. 1988 Proc. Natl. Acad. Sci. USA 85:7448-7451.
MacRae et al., Structural Basis for Double-Stranded RNA Processing by Dicer. 2006 Science 311(5758):195-198.
Zeng and Cullen, Structural requirements for pre-microRNA binding and nuclear export by Exportin 5. 2004 Nucleic Acids Res. 32(16):4776-85.
Griffiths-Jones, The microRNA Registry. 2004 Nucleic Acids Res. 32:D109-111.
Griffiths-Jones et al., miRBase: microRNA sequences, targets and gene nomenclature. 2006 Nucleic Acids Res. 34:D140-144.
Soukup and Breaker, Relationship between internucleotide linkage geometry and the stability of RNA. 1999 RNA 5:1308-1325.
Abbas-Terki et al., Lentiviral-mediated RNA interference. 2002 Hum Gene Ther 13: 2197-2201.

(56) References Cited

OTHER PUBLICATIONS

Hutvagner et al., Sequence-specific inhibition of small RNA function. 2004 PLoS Biol 2: E98.
Meister, Sequence-specific inhibition of microRNA- and siRNA-induced RNA silencing. 2004 RNA 10:544-550.
Bartlett and Davis, Insights into the kinetics of siRNA-mediated gene silencing from live-cell and live-animal bioluminescent imaging. 2006 Nucleic Acids Res 34:322-333.
Malphettes and Fussenegger, Impact of RNA interference on gene networks. 2006 Metab Eng 8:672-683.
Raab and Stephanopoulos, Dynamics of gene silencing by RNA interference. 2004 Biotechnol Bioeng 88:121-132.
Kiga et al., An RNA aptamer to the xanthine-guanine base with a distinctive mode of purine recognition. 1998 Nucleic Acids Res 26:1755-1760.
Thompson et al., Group I aptazymes as genetic regulatory switches. 2002 BMC Biotechnol 2:21.
Suel et al., Tunability and noise dependence in differentiation dynamics. 2007 Science 315:1716-1719.
Gardner et al., Construction of a genetic toggle switch in *Escherichia coli*. 2000 Nature 403:339-342.
Yi et al., Exportin-5 mediates the nuclear export of premicroRNAs and short hairpin RNAs. 2003 Genes Dev 17:3011-3016.
Ketting et al., Dicer functions in RNA interference and in synthesis of small RNA involved in developmental timing in *C. elegans*. 2001 Genes Dev 15:2654-2659.
Gregory et al., Human RISC couples microRNA biogenesis and posttranscriptional gene silencing. 2005 Cell 123:631-640.
Kok et al., Human TRBP and PACT directly interact with each other and associate with dicer to facilitate the production of small interfering RNA. 2007 J Biol Chem 282:17649-17657.
Lee et al., The role of PACT in the RNA silencing pathway. 2006 EMBO J 25:522-532.
Matranga et al., Passenger-strand cleavage facilitates assembly of siRNA into Ag02-containing RNAi enzyme complexes. 2005 Cell 123:607-620.
Rand et al., Argonaute2 cleaves the anti-guide strand of siRNA during RISC activation. 2005 Cell 123:621-629.
Westerhout and Berkhout, A systematic analysis of the effect of target RNA structure on RNA interference. 2007 Nucleic Acids Res. 35(13):4322-4330.
Grimm et al., Fatality in mice due to oversaturation of cellular microRNNshort hairpin RNA pathways. 2006 Nature 441:537-541.
Yi et al., Overexpression of exportin 5 enhances RNA interference mediated by short hairpin RNAs and microRNAs. 2005 RNA 11:220-226.
Danilova et al., RNAKinetics: a web server that models secondary structure kinetics of an elongating RNA. 2006 J Bioinform Comput Biol 4:589-596.
Croft et al., Is prokaryotic complexity limited by accelerated growth in regulatory overhead? 2003 Genome Biology 5:P2.
Dueber et al., Engineering synthetic signaling proteins with ultrasensitive input-output control. 2007 Nat Biotechnol 25:660-662.
Elowitz and Leibler, A synthetic oscillatory network of transcriptional regulators. 2000 Nature 403:335-338.
Flotte, Size does matter: overcoming the adeno-associated virus packaging limit. 2000 Respir Res 1:16-18.
Grate and Wilson, Inducible regulation of the *S. cerevisiae* cell cycle mediated by an RNA aptamer-ligand complex. 2001 Bioorg Med Chem 9:2565-2570.
Grieger and Samulski, Packaging capacity of adeno-associated virus serotypes: impact of larger genomes on infectivity and postentry steps. 2005 J Virol 79:9933-9944.
Grundy and Henkin, From ribosome to riboswitch: control of gene expression in bacteria by RNA structural rearrangements. 2006 Crit Rev Biochem Mol Biol 41:329-338.

Hall et al., Computational selection of nucleic acid biosensors via a slip structure model. 2007 Biosens Bioelectron 22:1939-1947.
Hooshangi et al., Ultrasensitivity and noise propagation in a synthetic transcriptional cascade. 2005 Proc Natl Acad Sci USA 102: 3581-3586.
Huang and Ferrell, Ultrasensitivity in the mitogen-activated protein kinase cascade. 1996 Proc Natl Acad Sci USA 93: 10078-10083.
Jenison et al., High-resolution molecular discrimination by RNA. 1994 Science 263:1425-1429.
Lee et al., Aptamer database. 2004 Nucleic Acids Res 32:D95-100.
Lynch et al., A high-throughput screen for synthetic riboswitches reveals mechanistic insights into their function. 2007 Chem Biol 14:173-184.
Ogawa and Maeda, An artificial aptazyme-based riboswitch and its cascading system in *E. coli*. 2008 Chembiochem 9:206-209.
Shalgi et al., Global and Local Architecture of the Mammalian microRNA-Transcription Factor Regulatory Network. 2007 PLoS Comput Biol 3:e131.
Sudarsan et al., Metabolite-binding RNA domains are present in the genes of eukaryotes. 2003 RNA 9:644-647.
Suess et al., Conditional gene expression by controlling translation with tetracycline-binding aptamers. 2003 Nucleic Acids Res 31:1853-1858.
Weigand and Suess, Tetracycline aptamer-controlled regulation of pre-mRNA splicing in yeast. 2007 Nucleic: Acids Res 35:4179-4185.
Wieland and Hartig, Improved aptazyme design and in vivo screening enable riboswitching in bacteria. 2008 Angew Chem Int Ed Engl47:2604-2607.
Javaherian et al., Selection of aptamers for a protein target in cell lysate and their application to protein purification. 2009 Nucleic Acids Res. 37(8):e62.
Yunusov et al., Kinetic capillary electrophoresis-based affinity screening of aptamer clones. 2009 Anal Chim Acta. 631(1):102-7.
Amarzguioui et. al. , Tolerance for mutations and chemical modifications in a siRNA, *Nucleic Acid Research* 31: 589-595, 2003.
Chiu & Rana, RNAi in Human Cells: Basic Structural and Functional Features of Small Interfering RNA, Mol. Cell 10: 549-561,2002.
Chiu & Rana, siRNA function in RNAi: A chemical modification analysis, RNA 9: 1034-1048,2003.
Geiger, Burgstaller et al., RNA aptamers that bind L-arginine with sub-micromolar dissociation constants and high enantioselectivity,Nucleic Acids Research vol. 24, Issue 6, 1029-1036, 1996.
Hamada et al.,Effects on RNA Interference in Gene Expression (RNAi) in Cultured Mammalian Cells of Mismatches and the Introduction of Chemical Modifications at the 3'-Ends of siRNAs, *Antisense Nucleic Acid Drug Dev*. 12(5): 301-309,2002.
Harborth et al.,Sequence, Chemical, and Structural Variation of Small Interfering RNAs and Short Hairpin RNAs and the Effect on Mammalian Gene Silencing ,*Antisense Nucleic Acid Drug Dev*. 13(2): 83-105,2003.
Hwang et al., A Hexanucleotide Element Directs MicroRNA Nuclear Import, *Science* 315: 97-100, 2007.
Kim et al., Synthetic dsRNA Dicer substrates enhance RNAi potency and efficacy ,*Nature Biotech*. 23: 222-226, 2008.
Lescoute and Westhof, Topology of three-way junctions in folded RNAs, *RNA* 12: 83-93, 2006.
Li and Breaker, Kinetics of RNA Degradation by Specific Base Catalysis of Transesterification Involving the 2'-Hydroxyl Group, *J Am. Chem. Soc*. 121: 5364-5372, 1999.
McBride et al., Artificial miRNAs mitigate shRNA-mediated toxicity in the brain: Implications for the therapeutic development of RNAi, *PNAS* 105: 5868, 2008.
Nickols et al.,Suppression of androgen receptor-mediated gene expression by a sequence-specific DNA-binding polyamide ,*Proc. Natl.Acad. Sci. USA* 104: 10418-10423,2007.
Ohrt et ai., Fluorescence correlation spectroscopy and fluorescence cross-correlation spectroscopy reveal the cytoplasmic origination of loaded nuclear RISC in vivo in human cells, *Nucleic Acids Res*. 36(20): 6439-6449, 2008.

(56) References Cited

OTHER PUBLICATIONS

Schwarz et. al., Evidence that siRNAs Function as Guides, Not Primers, in the *Drosophila* and Human RNAi Pathways, Mol. Cell 10: 537-548, 2002.

Soukup and Soukup, Riboswitches exert genetic control through metabolite-induced conformational change, Current Opinions in Structural Biology 14: 344, 2004.

Zhou et al., Novel Dual Inhibitory Function Aptamer-siRNA Delivery System for HIV-1 Therapy, *Molecular Therapy* 16: 1481-1489, 2008.

* cited by examiner

Figure 25   output protein (high when A+B)

FIG. 27A

Single-input gates
Single-input Buffer gates

L2bulge1 (Buffer1 from Fig. 2B)
5'<u>CCTAGG</u>*AAACAAACAAA*GCTGTCACCGGA|TGTCCTT|TCCGGTCTGATGAGTCC|GT|GTCC
|ATACCAGCATCGTCTTGATGCCCTTGGCAG|GGACGGGACGA|GGACAAACAGC*AAAAA*
*GAAAAATAAAA*<u>CTCGAG</u>

L2bulge5 (Buffer5 from Fig. 2B)
5'<u>CCTAGG</u>*AAACAAACAAA*GCTGTCACCGGA|TGTGCTT|TCCGGTCTGATGAGTCC|GT|GTCC
A|ATACCAGCATCGTCTTGATGCCCTTGGCAG|TGGACGGGACGA|GGACAAACAGC*AAA*
*AAGAAAAATAAAA*<u>CTCGAG</u>

L2bulge8 (Buffer8 from Fig. 2B)
5'<u>CCTAGG</u>*AAACAAACAAA*GCTGTCACCGGA|TGTGCTT|TCCGGTCTGATGAGTCC|GT|TGTCC
|ATACCAGCATCGTCTTGATGCCCTTGGCAG|GGACGGGACGGA|GGACAAACAGC*AAAA*
*AGAAAAATAAAA*<u>CTCGAG</u>

L2bulge9
5'<u>CCTAGG</u>*AAACAAACAAA*GCTGTCACCGGA|TGTGCTT|TCCGGTCTGATGAGTCC|GT|TGTCC
A|ATACCAGCATCGTCTTGATGCCCTTGGCAG|TGGATGGGGACGGA|GGACAAACAGC*A*
*AAAGAAAATAAAA*<u>CTCGAG</u>

L2bulge1tc (Buffer-tc from Fig. 2B)
5'<u>CCTAGG</u>*AAACAAACAAA*GCTGTCACCGGA|TGTGCTT|TCCGGTCTGATGAGTCC|GT|GTCC
|AAAACATACCAGATTTCGATCTGGAGAGGTGAAGAATTCGACCACCT|GGACGGGACGA|
GGACAAACAC*AAAAAGAAAAATAAAA*<u>CTCGAG</u>

Single-input Inverter gates

L2bulgeOff1 (Inverter1 from Fig. 2B)
5'<u>CCTAGG</u>*AAACAAACAAA*GCTGTCACCGGA|TGTGCTT|TCCGGTCTGATGAGTCC|GT|GTTGC
TG|ATACCAGCATCGTCTTGATGCCCTTGG|CAG|CAGTGGACGA|GGACAAACAGC*AAAAA*
*GAAAAATAAAA*<u>CTCGAG</u>

L2bulgeOff1tc
5'<u>CCTAGG</u>*AAACAAACAAA*GCTGTCACCGGA|TGTGCTT|TCCGGTCTGATGAGTCC|GT|TGTTG
AGG|AAAACATACCAGATTTCGATCTGGAGAGGTGAAGAATTCGACCA|CCTCCTTATGG
GA|GGACAAACAGC*AAAAAGAAAAATAAAA*<u>CTCGAG</u>

L2bulgeOff2tc

FIG. 27B

5'CCTAGG*AAACAAACAAA*GCTGTCACCGGA|TGTGCTT|TCCGGTCTGATGAGTCCGTATGA
GG|AAAACATACCAGATTTCGATCTGGAGAGGTGAAGAATTCGACCA|CCTCCTTAGAGG
|AGGACAAACGC*AAAAAGAAAAATAAAAA*CTCGAG

L2bulgeOff3tc
5'CCTAGG*AAACAAACAAA*GCTGTCACCGGA|TGTGCTT|TCCGGTCTGATGAGTCCGTTGAT
GAGG|AAAACATACCAGATTTCGATCTGGAGAGGTGAAGAATTCGACCA|CCTCCTTAGA
GGA|GGACAAACAGC*AAAAAGAAAAATAAAAA*CTCGAG L2cm4 (Inverter4 from Fig. 2B)
5'CCTAGG*AAACAAACAAA*GCTGTCACCGGA|TGTGCTT|TCCGGTCTGATGAGTCCGTCCTG
G|ATACCAGCATCGTCTTGATGCCCTTGGCAG|TCATAGA|GGACAAACAGC*AAAAAGAAAA
ATAAAAA*CCGAG L1cm10
5'CCTAGG*AAACAAACAAA*GCTGTCACCGGA|TGT|AAATG|ATACCAGCATCGTCTTGATGCC
|CTTGGCAG|CTGC|GCTT|TCCGGTCTGATGAGTCC|GTGAGGACAAACAGC*AAAAAGAAAAA
TAAAAA*CTGAG

Higher-order devices (SI 1: signal integration within the 3' UTR)

Two coupled Buffer or Inverter gates responsive to the same input

2xL2bulge1 (2xBuffer1 from Fig. 2B)
5'CCTAGG*AAACAAACAAA*GCTGTCACCGGA|TGTGCTT|TCCGGTCTGATGAGTCCGTGTCC
|ATACCAGCATCGTCTTGATGCCCTTGGCAG|GGACGGGAC|GA|GGACAAACAGCAAAAA
GAAAAATAAAAACTCGAG*AAACAAACAAA*GCTGTCACCGGA|TGTGCTT|TCCGGTCTGATGA
GTCCGT|GTCC|ATACCAGCATCGTCTTGATGCCCTTGGCAG|GGACGGGAC|GA|GGACAAA
|CAGC*AAAAAGAAAAATAAAA*CTCGAG 2xL2bulgeOff1 (2xInverter1 from Fig. 2B)
5'CCTAGG*AAACAAACAAA*GCTGTCACCGGA|TGTGCTT|TCCGGTCTGATGAGTCCGTGTTGC
TG|ATACCAGCATCGTCTTGATGCCCTTGG|CAGCAGTGGAC|GA|GGACAAACAGCAAAA
AGAAAAATAAAAACTCGAG*AAACAAACAAA*GCTGTCACCGGA|TGTGCTT|TCCGGTCTGATG
A|GTCCGT|GTTGCTG|ATACCAGCATCGTCTTGATGCCCTTGG|CAGCAGTGGAC|GA|GGAC
AAA|CAGC*AAAAAGAAAATAAAAA*CTCGAG

AND gates

AND1 (L2bulge1+L2bulge1tc)
5'CCTAGG*AAACAAACAAA*GCTGTCACCGGA|TGTGCTT|TCCGGTCTGATGAGTCCGTGTCC
|ATACCAGCATCGTCTTGATGCCCTTGGCAG|GGACGGGAC|GA|GGACAAACAGCAAAAA
GAAAAATAAAAACTCGAG*AAACAAACAAA*GCTGTCACCGGA|TGTGCTT|TCCGGTCTGATGA
GTCCGT|GTCC|AAAACATACCAGATTTCGATCTGGAGAGGTGAAGAATTCGACCACCT|GG
ACGGGAC|GA|GGACAAACGC*AAAAAGAAAAATAAAAA*CTCGAG

FIG. 27C

AND2 (L2bulge9+L2bulge1tc)
5'CCTAGG*AAACAAACAAA*GCTGTCACCGGATGTGCTTTCCGGTCTGATGAGTCCGTTGTCC
AATACCAGCATCGTCTTGATGCCCTTGGCAGTGGATGGGGACGGAGGACGAAACAGCA
AAAAGAAAATAAAAA*CTCGAGAAACAAACAAA*GCTGTCACCGGATGTGCTTTCCGGTCTG
ATGAGTCCGTGTCCAAAACATACCAGATTTCGATCTGGAGAGGTGAAGAATTCGACCAC
CTGGACGGGACGAGGACGAAACAGC*AAAAAGAAAAATAAAAA*CTCGAG

NOR gates

NOR1 (L2bulgeOff1+L2bulgeOff1tc)
5'CCTAGG*AAACAAACAAA*GCTGTCACCGGATGTGCTTTCCGGTCTGATGAGTCCGTGTTGC
TGATACCAGCATCGTCTTGATGCCCTTGGCAGCAGTGGACGAGGACGAAACAGCAAAA
AGAAAAATAAAAA*CTCGAGAAACAAACAAA*GCTGTCACCGGATGTGCTTTCCGGTCTGATG
AGTCCGTTGTTGAGGAAAACATACCAGATTTCGATCTGGAGAGGTGAAGAATTCGACCA
CCTCCTTATGGGAGGACGAAACAGC*AAAAAGAAAAATAAAAA*CTCGAG NOR2 (L2bulgeOff1+L2bulgeOff2tc)
5'CCTAGG*AAACAAACAAA*GCTGTCACCGGATGTGCTTTCCGGTCTGATGAGTCCGTGTTGC
TGATACCAGCATCGTCTTGATGCCCTTGGCAGCAGTGGACGAGGACGAAACAGCAAAA
AGAAAAATAAAAA*CTCGAGAAACAAACAAA*GCTGTCACCGGATGTGCTTTCCGGTCTGATG
AGTCCGTATGAGGAAAACATACCAGATTTCGATCTGGAGAGGTGAAGAATTCGACCAC
CTCCTTAGAGGAGGACGAAACAGC*AAAAAGAAAAATAAAAA*CTCGAG

Bandpass filter

Bandpass filter1 (L2bulge1+L2bulgeOff1)
5'CCTAGG*AAACAAACAAA*GCTGTCACCGGATGTGCTTTCCGGTCTGATGAGTCCGTGTCC
ATACCAGCATCGTCTTGATGCCCTTGGCAGGGACGGGACGAGGACGAAACAGC*AAAAA
GAAAAATAAAAACTCGAGAAACAAACAAA*GCTGTCACCGGATGTGCTTTCCGGTCTGATGAGT
CCGTGTTGCTGATACCAGCATCGTCTTGATGCCCTTGGCAGCAGTGGACGAGGACGAA
ACAGC*AAAAAGAAAAATAAAAA*CTCGAG Higher-order devices (SI 2: signal integration at the ribozyme core through two stems)

NAND gates

NAND1 (L1cm10-L2bulgeOff1tc)
5'CCTAGG*AAACAAACAAA*GCTGTCACCGGATGTAAATGATACCAGCATCGTCTTGATGCC
CTTGGCAGCTGCGCTTTCCGGTCTGATGAGTCCGTTGTTGAGGAAAACATACCAGATTT
CGATCTGGAAGGTGAAGAATTCGACCACCTCCTTATGGGAGGACGAAACAGC*AAAAAG
AAAAATAAAAA*CTCGAG NAND2 (L1cm10-L2bulgeOff3tc)
5'CCTAGG*AAACAAACAAA*GCTGTCACCGGATGTAAATGATACCAGCATCGTCTTGATGCC
CTTGGCAGCTGCGCTTTCCGGTCTGATGAGTCCGTTGATGAGGAAAACATACCAGATTT

FIG. 27D

CGATCTGGAAGGTGAAGAATTCGACCACCTCCTTAGAGGAGGAC GAAA CAGC*AAAAAG AAAAATAAAAA*CTCGAG

Higher-order devices (SI 3: signal integration at a single ribozyme stem)

AND gates

AND1 (tc-theo-On1)
5'CCTAGG*AAACAAACAAA*GCTG TC ACCGGATGTGCTTTCCGGT CTGATGA GTCCGTGTCC ATACCAGCATCGCTCAAAAACATACCAGATTTCGATCTGGAGAGGTGAAGAATTCGACCA CCTGAGTCTGATGCCCTTGGCAGGGACGGGACGAGGAC GAAA CAGC*AAAAAGAAAAATA AAAA*CTCGAG AND2 (tc-theo-On2)
5'CCTAGG*AAACAAACAAA*GCTG TC ACCGGATGTGCTTTCCGGT CTGATGA GTCCGTGTCC ATACCAGCATCGCTAAAAACATACCAGATTTCGATCTGGAGAGGTGAAGAATTCGACCAC CTAGTCTTGTGCCCTTGGCAGGGACGGGACGAGGAC GAAA CAGC*AAAAAGAAAAATAAAA A*CTCGAG AND3 (tc-theo-On3)
5'CCTAGG*AAACAAACAAA*GCTG TC ACCGGATGTGCTTTCCGGT CTGATGA GTCCGTGTCC ATACCAGCATCGTGTAAAAACATACCAGATTTCGATCTGGAGAGGTGAAGAATTCGACCA CCTACATCTGATGCCCTTGGCAGGGACGGGACGAGGAC GAAA CAGC*AAAAAGAAAAATA AAAA*CTCGAG

OR gates

OR1 (tc/theo-On1)
5'CCTAGG*AAACAAACAAA*GCTG TC ACCGGATGTGCTTTCCGGT CTGATGA GTCCGTGTCC ATACCAGCATCGGGCCTAAAAACATACCAGATTTCGATCTGGAGAGGTGAAGAATTCGA CCACCTAGGTTCTTGATGCCCTTGGCAGGGACGGGACGAGGAC GAAA CAGC*AAAAAGA AAAATAAAAA*CTCGAG OR2 (tc/theo-On2)
5'CCTAGG*AAACAAACAAA*GCTG TC ACCGGATGTGCTTTCCGGT CTGATGA GTCCGTGTCC ATACCAGCATCGGTGGTAAAAACATACCAGATTTCGATCTGGAGAGGTGAAGAATTCGA CCACCTACCATCTTGATGCCCTTGGCAGGGACGGGACGAGGAC GAAA CAGC*AAAAAGAA AAATAAAAA*CTCGAG

Two coupled internal gates responsive to the same input theo-theo-On1
5'CCTAGG*AAACAAACAAA*GCTG TC ACCGGATGTGCTTTCCGGT CTGATGA GTCCGTGTCC ATACCAGCATCGTTTATACCAGCATCGTCTTGATGCCCTTGGCAGAAATCTTGATGCCCT TGGCAGGGCGGGACGAGGAC GAAA CAGC*AAAAAGAAAAATAAAAA*CTCGAG theo-theo-On2

FIG. 27E

5'<u>CCTAGG</u>*AAACAAACAAA*GCTG▰ACCGGA|TGTGCTT|TCCGGT▰GTCCGTGTCC
|ATACCAGCATCG|TTGA|ATACCAGCATCGTCTTGATGCCCTTGGCAG|TTGA|TCTTGATGC|
|CCTTGGCAG|GACGGGACGAGGAC▰CAGC*AAAAAGAAAAATAAAAA*<u>CTCGAG</u> theo-theo-On3
5'<u>CCTAGG</u>*AAACAAACAAA*GCTG▰ACCGGA|TGTGCTT|TCCGGT▰GTCCGTGTCC
|ATACCAGCATCG|ATTG|ATACCAGCATCGTCTTGATGCCCTTGGCAG|CAGT|TCTTGATGC|
|CCTTGGCAG|GACGGGACGAGGAC▰CAGC*AAAAAGAAAAATAAAAA*<u>CTCGAG</u> theo-theo-On4
5'<u>CCTAGG</u>*AAACAAACAAA*GCTG▰ACCGGA|TGTGCTT|TCCGGT▰GTCCGTGTCC
|ATACCAGCATCG|TATG|ATACCAGCATCGTCTTGATGCCCTTGGCAG|CGTA|TCTTGATGC|
|CCTTGGCAG|GACGGGACGAGGAC▰CAGC*AAAAAGAAAAATAAAAA*<u>CTCGAG</u> theo-theo-On5
5'<u>CCTAGG</u>*AAACAAACAAA*GCTG▰ACCGGA|TGTGCTT|TCCGGT▰GTCCGTGTCC
|ATACCAGCATCG|ATC|ATACCAGCATCGTCTTGATGCCCTTGGCAG|GAT|TCTTGATGCCC|
|TTGGCAG|GGCGGGACGAGGAC▰CAGC*AAAAAGAAAAATAAAAA*<u>CTCGAG</u> theo-theo-On6
5'<u>CCTAGG</u>*AAACAAACAAA*GCTG▰ACCGGA|TGTGCTT|TCCGGT▰GTCCGTGTCC
|ATACCAGCATCG|ATTG|ATACCAGCATCGTCTTGATGCCCTTGGCAG|CAAT|TCTTGATGC|
|CCTTGGCAG|GACGGGACGAGGAC▰CAGC*AAAAAGAAAAATAAAAA*<u>CTCGAG</u> theo-theo-On7
5'<u>CCTAGG</u>*AAACAAACAAA*GCTG▰ACCGGA|TGTGCTT|TCCGGT▰GTCCGTGTCC
|ATACCAGCATCG|GTAA|ATACCAGCATCGTCTTGATGCCCTTGGCAG|TTGC|TCTTGATGC|
|CCTTGGCAG|GACGGGACGAGGAC▰CAGC*AAAAAGAAAAATAAAAA*<u>CTCGAG</u> theo-theo-On8
5'<u>CCTAGG</u>*AAACAAACAAA*GCTG▰ACCGGA|TGTGCTT|TCCGGT▰GTCCGTGTCC
|ATACCAGCATCG|TTGA|ATACCAGCATCGTCTTGATGCCCTTGGCAG|TTGA|TCTTGATGC|
|CCTTGGCAG|GACGGGACGAGGAC▰CAGC*AAAAAGAAAAATAAAAA*<u>CTCGAG</u> theo-theo-On9
5'<u>CCTAGG</u>*AAACAAACAAA*GCTG▰ACCGGA|TGTGCTT|TCCGGT▰GTCCGTGTCC
|ATACCAGCATCG|GTTGA|ATACCAGCATCGTCTTGATGCCCTTGGCAG|TTGAT|TCTTGAT|
|GCCCTTGGCG|GACGGGACGAGGAC▰CAGC*AAAAAGAAAAATAAAAA*<u>CTCGAG</u> theo-theo-On10 (Cooperative Buffer gate)
5'<u>CCTAGG</u>*AAACAAACAAA*GCTG▰ACCGGA|TGTGCTT|TCCGGT▰GTCCGTGTCC
|ATACCAGCATCG|GTTGA|ATACCAGCATCGTCTTGATGCCCTTGGCAG|TTGAC|TCTTGAT|
|GCCCTTGGCG|GGATAGGACGAGGAC▰CAGC*AAAAAGAAAAATAAAAA*<u>CTCGAG</u> theo-theo-On11 (Cooperative Buffer gate)

FIG. 27F

5'CCTAGG*AAACAAACAAA*GCTGTCACCGGATGTGCTTTCCGGTCTGATGAGTCCGTGTCC
ATACCAGCATCGGTTGAATACCAGCATCGTCTTGATGCCCTTGGCAGTTGATTCTTGAT
GCCCTTGGCGGATAGGACGAGGACGAAACAGC*AAAAAGAAAAATAAAAA*CTCGAG theo-theo-On12 (Cooperative Buffer gate)
5'CCTAGG*AAACAAACAAA*GCTGTCACCGGATGTGCTTTCCGGTCTGATGAGTCCGTGTCC
ATACCAGCATCGATTGAATACCAGCATCGTCTTGATGCCCTTGGCAGTTGATTCTTGAT
GCCCTTGGCGGATAGGACGAGGACGAAACAGC*AAAAAGAAAAATAAAAA*CTCGAG theo-theo-On13 (Cooperative Buffer gate)
5'CCTAGG*AAACAAACAAA*GCTGTCACCGGATGTGCTTTCCGGTCTGATGAGTCCGTGTCC
ATACCAGCATCGTGTTATACCAGCATCGTCTTGATGCCCTTGGCAGAATGTCTTGATGC
CCTTGGCAGGATAGGACGAGGACGAAACAGC*AAAAAGAAAAATAAAAA*CTCGAG

Two coupled internal Inverter gates responsive to the same input theo-theo-Off1
5'CCTAGG*AAACAAACAAA*GCTGTCACCGGATGTGCTTTCCGGTCTGATGAGTCCGTGTTAT
GATACCAGCATCGACATACCAGCATCGTCTTGATGCCCTTGGCAGGTTCTTGATGCCCT
TGGCAGCAGGACGAGGACGAAACAGC*AAAAAGAAAAATAAAAA*CTCGAG theo-theo-Off2
5'CCTAGG*AAACAAACAAA*GCTGTCACCGGATGTGCTTTCCGGTCTGATGAGTCCGTGTTGC
TGATACCAGCATCGACATACCAGCATCGTCTTGATGCCCTTGGCAGGTTCTTGATGCCC
TTGGCAGCGTGGACGAGGACGAAACAGC*AAAAAGAAAAATAAAAA*CTCGAG theo-theo-Off3

5'CCTAGG*AAACAAACAAA*GCTGTCACCGGATGTGCTTTCCGGTCTGATGAGTCCGTGTTAT
GATACCAGCATCGGACATACCAGCATCGTCTTGATGCCCTTGGCAGGTTTCTTGATGCC
CTTGGCAGATGGACGAGGACGAAACAGC*AAAAAGAAAAATAAAAA*CTCGAG theo-theo-Off4
5'CCTAGG*AAACAAACAAA*GCTGTCACCGGATGTGCTTTCCGGTCTGATGAGTCCGTGTGTC
TGATACCAGCATCGACATACCAGCATCGTCTTGATGCCCTTGGCAGGTTCTTGATGCCC
TTGGCAGCGGGACGAGGACGAAACAGC*AAAAAGAAAAATAAAAA*CTCGAG theo-theo-Off5
5'CCTAGG*AAACAAACAAA*GCTGTCACCGGATGTGCTTTCCGGTCTGATGAGTCCGTGTGTC
CTGATACCAGCATCGGACATACCAGCATCGTCTTGATGCCCTTGGCAGGTTTCTTGATG
CCCTTGGCGCAGGGACGAGGACGAAACAGC*AAAAAGAAAAATAAAAA*CTCGAG theo-theo-Off6 (Cooperative Inverter gate)
5'CCTAGG*AAACAAACAAA*GCTGTCACCGGATGTGCTTTCCGGTCTGATGAGTCCGTGTTAT
GATACCAGCATCGGCATACCAGCATCGTCTTGATGCCCTTGGCAGGTTCTTGATGCCCT
TGGCAGCAGGACGAGGACGAAACAGC*AAAAAGAAAAATAAAAA*CTCGAG theo-theo-Off7

FIG. 27G

5'CCTAGG*AAACAAACAAA*GCTGTCACCGGATGTGCTTTCCGGTCTGATGAGTCCGTGTTGC
TGATACCAGCATCGACATACCAGCATCGTCTTGATGCCCTTGGCAGGTTCTTGATGCCC
TTGGCAGCGGGACGAGGACGAAACAGC*AAAAAGAAAAATAAAAA*CTCGAG theo-theo-Off8
5'CCTAGG*AAACAAACAAA*GCTGTCACCGGATGTGCTTTCCGGTCTGATGAGTCCGTGTGTT
TGATACCAGCATCGACATACCAGCATCGTCTTGATGCCCTTGGCAGGTTCTTGATGCCC
TTGGCAGCAGGACGAGGACGAAACAGC*AAAAAGAAAAATAAAAA*CTCGAG

Mutated coupled internal gates theo-theo-On1M1
5'CCTAGG*AAACAAACAAA*GCTGTCACCGGATGTGCTTTCCGGTCTGATGAGTCCGTGTCC
AGACCAGCATCGTTTATACCAGCATCGTCTTGATGCCCTTGGCAGAAATCTTGATGCCT
ATGGCAGGGCGGGACGAGGACGAAACAGC*AAAAAGAAAAATAAAAA*CTCGAG theo-theo-On1M2
5'CCTAGG*AAACAAACAAA*GCTGTCACCGGATGTGCTTTCCGGTCTGATGAGTCCGTGTCC
ATACCAGCATCGTTTATACCAGCATCGTCTTGATGCCTATGGCAGAAATCTTGATGCCC
TTGGCAGGGCGGGACGAGGACGAAACAGC*AAAAAGAAAAATAAAAA*CTCGAG theo-theo-On13M1
5'CCTAGG*AAACAAACAAA*GCTGTCACCGGATGTGCTTTCCGGTCTGATGAGTCCGTGTCC
ATACCAGCATCGTGTTATACCAGCATCGTCTTGATGCCCTTGGCAGAATGTCTTGATGC
CTATGGCAGGATAGGACGAGGACGAAACAGC*AAAAAGAAAAATAAAAA*CTCGAG theo-theo-On13M2
5'CCTAGG*AAACAAACAAA*GCTGTCACCGGATGTGCTTTCCGGTCTGATGAGTCCGTGTCC
ATACCAGCATCGTGTTAGACCAGCATCGTCTTGATGCCTATGGCAGAATGTCTTGATGC
CCTTGGCAGGATAGGACGAGGACGAAACAGC*AAAAAGAAAAATAAAAA*CTCGAG theo-theo-Off2M1
5'CCTAGG*AAACAAACAAA*GCTGTCACCGGATGTGCTTTCCGGTCTGATGAGTCCGTGTTGC
TGAGACCAGCATCGACATACCAGCATCGTCTTGATGCCCTTGGCAGGTTCTTGATGCCT
ATGGCAGCGTGGACGAGGACGAAACAGC*AAAAAGAAAAATAAAAA*CTCGAG theo-theo-Off2M2
5'CCTAGG*AAACAAACAAA*GCTGTCACCGGATGTGCTTTCCGGTCTGATGAGTCCGTGTTGC
TGATACCAGCATCGACATACCAGCATCGTCTTGATGCCTATGGCAGGTTCTTGATGCCC
TTGGCAGCGTGGACGAGGACGAAACAGC*AAAAAGAAAAATAAAAA*CTCGAG theo-theo-Off6M1
5'CCTAGG*AAACAAACAAA*GCTGTCACCGGATGTGCTTTCCGGTCTGATGAGTCCGTGTTAT
GAACCCAGCATCGGCATACCAGCATCGTCTTGATGCCCTTGGCAGGTTCTTGATGCCTA
TGGCAGCAGGACGAGGACGAAACAGC*AAAAAGAAAAATAAAAA*CTCGAG theo-theo-Off6M2

FIG. 27H

5'CCTAGG*AAACAAACAAA*GCTGTCACCGGATGTGCTTTCCGTCTGATGAGTCCGTGTTAT
GATACCAGCATCGGCATACCAGCATCGTCTTGATGCCTATGGCAGGTTCTTGATGCCCT
TGGCAGCAGGACGAGGACGAAACAGC*AAAAAGAAAAATAAAAA*CTCGAG

HIGHER-ORDER CELLULAR INFORMATION PROCESSING DEVICES

CROSS-REFERENCE TO RELATED APPLICATIONS

This application claims the benefit of the filing date under 35 U.S.C. §119(e) to U.S. Provisional Application No. 60/993,659, filed on Sep. 12, 2007, the entire content of the above referenced application (including the specification and drawings) is incorporated herein by reference.

STATEMENT REGARDING FEDERAL FUNDING

Work described herein was funded, in whole or in part, by Grant No. NIH-R21 GM074767-01A1 awarded by the National Institute of Health (NIH), and Grant No. BES0545987 awarded by the National Science Foundation (NSF). The United States Government has certain rights in this invention.

BACKGROUND OF THE INVENTION

Basic and applied biological research and biotechnology are limited by the ability to get information into and from living systems and to act on information inside living systems. For example, there are only a small number of inducible promoter systems available to provide control over gene expression in response to exogenous molecules. Many of the molecular inputs to these systems are not ideal for broad implementation, because they can be expensive and introduce undesired pleiotropic effects. In addition, broadly applicable methods for getting information from cells noninvasively have been limited to strategies that rely on protein and promoter fusions to fluorescent proteins, which enable researchers to monitor protein levels and localization and transcriptional outputs of networks, leaving a significant amount of the cellular information content currently inaccessible.

Moreover, monitoring the status of a complex biological system usually entails simultaneous tracking and responding to a plurality of input signals, such as the presence/absence/concentration of specific molecules or metabolites. The ability to detect and respond to status change of the individual signals is desirable for any complex biological system.

SUMMARY OF THE INVENTION

One aspect of the invention provides a signal processing device for modulating the expression of a gene product depending on the presence or absence of ligands, the device comprising an RNA comprising: (1) a coding sequence for the gene product; (2) two or more aptamer domains and one or more actuator domain(s), wherein each of the aptamer domains binds one ligand, and each of the actuator domain(s) has a functional activity that affects the expression of the gene product, the stability of the RNA, and/or the extent of translation of the RNA, wherein binding of the aptamer domains by their respective ligands favors a conformation change in the actuator domain through a strand-displacement mechanism; and, wherein the conformation change modulates the functional activity, thereby affecting the expression of the gene product.

In one embodiment, the gene product of the signal processing device is a protein, such as a transcription factor (repressor or activator, etc.). In certain embodiments, the gene product is an enzyme, and the product of the enzyme (e.g., metabolite) is an input signal to another signal processing device.

In other embodiment, the gene product is a non-coding RNA, such as an antisense RNA, or a precursor for a small RNA (siRNA, miRNA, etc.) that may antagonize the function of a target gene.

Any actuator domains may be used in the subject signal processing device. In one embodiment, the signal processing device has at least one actuator domain(s) that is not a hammerhead ribozyme.

In certain embodiments, the RNA may comprise two or more aptamer-regulated polynucleotides in tandem, each aptamer-regulated polynucleotide comprising an aptamer domain and an actuator domain. In certain embodiments, the two or more aptamer-regulated polynucleotides are 3' to the coding sequence for the gene product.

In certain embodiments, the actuator domain for one of the aptamer-regulated polynucleotides is a ribozyme, such as a hammerhead ribozyme, which self-cleavage activity can be activated or inactivated upon ligand binding to the linked aptamer.

In certain embodiments, the actuator domain for one of the aptamer-regulated polynucleotides is a target sequence for siRNA or miRNA. For example, ligand binding may expose (or occupy by hybridization) the target sequence, which may serve as a target for siRNA or miRNA. The siRNA/miRNA may be produced from a different construct.

In certain embodiments, the actuator domain for one of the aptamer-regulated polynucleotides is an siRNA/miRNA precursor or RNase III substrate. For example, ligand binding may favor a conformation change in the actuator domain that allows or prevents the precursor or substrate to be processed/cut by Dicer to generate siRNA/miRNA against the coding sequence.

In certain embodiments, the actuator domain for one of the aptamer-regulated polynucleotides is an antisense sequence, an alternative splicing element, or an antisense targeting sequence.

In certain embodiments, at least one of the aptamer-regulated polynucleotides further comprises: (3) an information transmission domain (ITD) between the aptamer domain and the actuator domain, the information transmission domain comprising: (a) a general transmission region, (b) a switching strand, (c) a competing strand, wherein the switching strand and the competing strand compete to bind to the general transmission region through hybridization interactions. In certain embodiments, the switching strand and the competing strand are in a continuous sequence, such that there is no free-floating end, which may result in an improved switching mechanism. In certain embodiments, the switching strand and the competing strand substantially do not overlap. In certain embodiments, the switching strand and the competing strand have substantially the same sequence. In certain embodiments, the switching strand and the competing strand are in tandem.

In certain embodiments, at least two of the aptamer-regulated polynucleotides bind to the same ligand or bind to different ligands.

In certain embodiments, for each of the aptamer-regulated polynucleotides, independently, binding of its aptamer domain by a ligand favors a conformational change that leads to increased or decreased activity in its actuator domain.

In certain embodiments, each of the aptamer-regulated polynucleotides function independently from the other aptamer-regulated polynucleotides.

In certain embodiments, the aptamer domain for each of the aptamer-regulated polynucleotides independently binds a ligand selected from the group consisting of: a small peptide, a nucleic acid, a carbohydrate, a fatty acid or lipid, a non-peptide hormone (such as steroid), an amino acid or precursor thereof, a nucleotide or precursor thereof, a vitamin, a metal ion, a metabolite, a post-translationally modified protein, a signal transduction second messenger, an enzyme co-factor, an enzyme substrate, a product of an enzyme-mediated reaction, or a metabolic precursor or product thereof. In certain embodiments, the ligand is theophylline or tetracycline.

In certain embodiments, the expression of the protein is the highest or lowest when all of the aptamer-regulated polynucleotides bind their respective ligands. In certain embodiments, the expression of the protein is the highest or lowest when none of the aptamer-regulated polynucleotides bind their respective ligands.

In certain embodiments, the expression of the gene product is present only within a concentration range of a ligand.

In certain embodiments, the two or more aptamer domains are linked to a single actuator domain.

In certain embodiments, the actuator domain is a cis-acting hammerhead ribozyme comprising a catalytic core and stem I, stem II and stem III duplex regions extending therefrom, the stem I having a loop I single-stranded loop region opposite to the catalytic core, and the stem II having a loop II single-stranded loop region opposite to the catalytic core; the signal processing device further comprising two information transmission domains (ITDs), each having a first and second end and being directly coupled to the loop I or loop II through the first end; wherein each of the two or more aptamers are coupled to one of the information transmission domains through the second end, each of the aptamers binds a ligand, wherein, binding of the ligand to the aptamer favors a conformation change in the ITD and/or a change in the interaction of the information transmission domain with one or more of the loop, the stem, or the catalytic core sequences, such that the ribozyme undergoes self-cleavage of a backbone phosphodiester bond at a rate dependent upon the presence or absence of the ligand.

In certain embodiments, the actuator domain is a target sequence for an antisense sequence, an siRNA, or an miRNA.

In certain embodiments, the actuator domain is an antisense sequence, an siRNA or precursor thereof, an miRNA or precursor thereof, an shRNA or precursor thereof, an RNase III substrate, or an alternative splicing element.

In certain embodiments, the two or more aptamer domains bind to the same ligand or bind to different ligands.

In certain embodiments, the two or more aptamer domains are 3' to the coding sequence for the protein.

In certain embodiments, the signal processing device further comprises: (3) one or more information transmission domain(s) between the aptamer domains and the actuator domain, each of the information transmission domain(s) comprising: (a) a general transmission region, (b) a switching strand, (c) a competing strand, wherein the switching strand and the competing strand compete to bind to the general transmission region through hybridization interactions. In certain embodiments, the switching strand and the competing strand are in a continuous sequence.

In certain embodiments, each of the aptamer domains independently binds a ligand selected from the group consisting of: a small peptide, a nucleic acid, a carbohydrate, a fatty acid or lipid, a non-peptide hormone (such as steroid), an amino acid or precursor thereof, a nucleotide or precursor thereof, a vitamin, a metal ion, a metabolite, a post-translationally modified protein, a signal transduction second messenger, an enzyme co-factor, an enzyme substrate, a product of an enzyme-mediated reaction, or a metabolic precursor or product thereof.

In certain embodiments, the ligand is theophylline or tetracycline.

In certain embodiments, the expression of the gene product is the highest or lowest when all of the aptamers bind their respective ligands.

In certain embodiments, the expression of the gene product is the highest or lowest when none of the aptamers bind their respective ligands.

In certain embodiments, the expression of the gene product is present only within a concentration range of a ligand.

In certain embodiments, at least two of the aptamer domains are in tandem, such that one aptamer domain is linked to a single actuator domain.

In certain embodiments, the aptamer domains in tandem act cooperatively, such that binding of a first ligand by one aptamer domain facilitates the binding of a second ligand by another aptamer domain. In certain embodiments, the first ligand and the second ligand are the same or different. In certain embodiments, the aptamer domains in tandem act antagonistically, such that binding of a first ligand by one aptamer domain inhibits the binding of a second ligand by another aptamer domain.

In certain embodiments, the actuator domain is a ribozyme.

In certain embodiments, the actuator domain is an antisense sequence, an siRNA or precursor thereof, an miRNA or precursor thereof, an shRNA or precursor thereof, an RNase III substrate, an alternative splicing element, an antisense targeting sequence, or an RNAi targeting sequence.

In certain embodiments, the expression of the gene product is the highest or the lowest when all of the aptamer domains bind their respective ligands.

In certain embodiments, the expression of the gene product is the highest or the lowest when none of the aptamer domains bind their respective ligands.

In certain embodiments, the expression of the gene product is present only within a concentration range of a ligand.

In certain embodiments, the RNA is a transcription product.

In certain embodiments, the RNA comprises one or more modified nucleotides or nucleotide analogs. In certain embodiments, the modified nucleotides or nucleotide analogs are within the aptamer domains and/or the actuator domain(s).

In certain embodiments, the RNA is single-stranded. In certain embodiments, the device is functional in vivo. In certain embodiments, each of the aptamer domains binds the ligand specifically. For example, the binding affinity between the ligand and the aptamer (as measured by dissociation constant $K_d$) is at least 5-, 10-, 20-, 50, 100-, 200-, 500-, 1000-, 5000-, 10,000-times smaller than that for another ligand. In certain embodiments, the ligand has a molecular weight of no more than about 2000 Da, 1000 Da, 500 Da, 300 Da, 200 Da, 100 Da, or 50 Da. In certain embodiments, the ligand is a small peptide, a nucleic acid, a carbohydrate, a fatty acid or lipid, a non-peptide hormone (such as steroid), an amino acid or precursor thereof, a nucleotide or precursor thereof, a vitamin, a metal ion, a metabolite, a post-translationally modified protein, a signal transduction second messenger, an enzyme co-factor, an enzyme substrate, a product of an enzyme-mediated reaction, or a metabolic precursor or product thereof.

In certain embodiments, the extent of the conformation change in response to identical molecule concentration/status change is amenable to (rationally) adjustment/tuning. In certain embodiments, the adjustment/tuning of the device is achieved through rational sequence modification in the information transmission domain. In certain embodiments, the adjustment/tuning of the device is effected by modifying base-pairing interactions among the general transmission region, the switching strand, and/or the competing strand. In certain embodiments, the adjustment/tuning of the device is effected by changing the length of the pairing base-pairs at one or both ends of the duplex formed between the general transmission region and the switching strand, and/or the duplex formed between the general transmission region and the competing strand. In certain embodiments, the adjustment/tuning of the device is effected by changing base-pairing complementarity. In certain embodiments, the adjustment/tuning of the device is effected by changing the binding affinity between the modular sensor domain and the molecule without changing the size of the modular sensor domain. In certain embodiments, the adjustment/tuning of the device is effected by changing the size of the modular sensor domain. In some embodiments of the signal processing device, the extent of the conformation change in response to identical molecule concentration/status change is amenable to rational adjustment/tuning effected by any one or more of the embodiments described above. In certain embodiments, the modular actuator domain can be reliably or predictably exchanged for a different modular actuator domain without substantially affecting the function of the modular sensor domain and the information transmission domain. Similarly, in certain embodiments, the modular sensor domain and the modular information transmission domain can be reliably or predictably exchanged for a different modular sensor domain and a different modular information transmission domain, respectively, without substantially affecting the function of the other modular domains.

Another aspect of the invention is a vector or expression construct encoding the signal processing device described above.

In certain embodiments, the vector or expression construct further comprises one or more transcriptional regulatory sequences that regulate transcription from the vector or expression construct in a cell containing the vector or expression construct. For example, the cell is a mammalian cell, a human cell, a rodent cell, a fungus cell, a yeast cell, an insect cell, a worm cell, or a bacterium, or a plant cell. The subject devices may also be introduced directly into these cells, and the subject methods using the devices may also be used in these cells.

A related aspect of the invention relates to a cell engineered to include the signal processing device described above, or the vector or expression construct also described above.

Another aspect of the invention provides a method for regulating expression of a target gene, comprising: (i) providing a cell of the invention, wherein the gene product is a transcription activator or repressor of the target gene, or a non-coding RNA inhibitor of the target gene (antisense, siRNA/miRNA precursor, etc.), (ii) contacting the cell with one or more ligands that bind the two or more aptamer domains, thereby affecting the expression of the gene product and the expression of the target gene.

An additional aspect of the invention is a method for processing and integrating two or more biological inputs into a processed output, the method comprising: (1) providing a subject signal processing device, wherein each of the aptamer domains binds one ligand, and each of the biological inputs is represented by the presence or absence of a ligand; (2) monitoring the expression level and/or activity of the gene product as the processed output.

In certain embodiments, at least two of the aptamer domains bind the same ligand or bind different ligands.

In certain embodiments, the gene product is a reporter protein. In certain embodiments, the gene product is a transcription activator or repressor of a reporter gene. In other embodiments, the gene product is a fluorescent protein or an enzyme. In other embodiments, the gene product is a non-coding RNA, such as an antisense sequence or an siRNA/miRNA precursor that can be processed to yield siRNA/miRNA.

Another aspect of the invention is a method for rendering expression of a target gene in a cell dependent on the presence or absence of two or more ligands, comprising introducing into the cell a signal processing device as described herein, wherein each ligand is bound by at least one of the aptamer domains, and wherein the gene product modulates the expression of the target gene.

In certain embodiments, the gene product is a transcriptional repressor that inhibits the expression of the target gene. In certain embodiments, the transcriptional repressor specifically inhibits the expression of the target gene. In certain embodiments, the gene product is a transcriptional activator that increases the expression of the target gene. In certain embodiments, the transcriptional activator specifically increases the expression of the target gene.

In certain embodiments, the ligands are produced by the cell. In certain embodiments, the ligands are cell permeable agents that are contacted with the cell. In certain embodiments, the ligands are a mixture of ligands. For example, the ligands may include at least one ligand that is produced by the cell, and at least one ligand that is added to the cell or is caused to contact the cell.

Another aspect of the invention is a method for causing phenotypic regulation of cell growth, differentiation or viability in cells of a patient, comprising introducing into cells in the patient a signal processing device as described herein, where the aptamer domains bind to one or more ligands, the concentrations of which ligands are dependent on cellular phenotype, wherein binding of the ligands to the aptamer domains modulates expression of the gene product which inhibits or activates a target gene essential for altering the regulation of cell growth, differentiation or viability in the cells.

In certain embodiments, the method is used to induce or prevent cell death, to induce or prevent differentiation, to prevent the growth of hyperplastic or tumor cells, to reduce fat cells in the patient, to regulate growth and differentiation of stem cells, or to regulate activation of an immune response, in a manner dependent on the presence of the ligands.

In certain embodiments, the signal processing device, or an expression construct for transcribing the signal processing device, are introduced ex vivo into cells which are transplanted into the patient. This may be useful for ex vivo cellular therapeutic applications, where cells, such as stem cells or immune cells, are engineered ex vivo with the subject devices and/or transgenic constructs in order to regulate cellular phenotypes, such as differentiated states, proliferation, activation, immune response, etc.

An additional aspect of the invention is a pharmaceutical preparation that comprises the signal processing device described herein, or an expression construct, which, when transcribed, produces the signal processing device, and a pharmaceutically acceptable carrier suitable for use administration to a human or non-human patient.

Another aspect of the invention is a signal processing device for regulating the expression of a nucleic acid, depending on the presence or absence of two or more ligands, the device comprising: (1) two or more aptamer domains, each binding to a ligand, wherein each of the two or more ligands are bound by the aptamer domains, and (2) one or more actuator domains, each modulating in trans the expression of a transcriptional repressor or activator, or a non-coding RNA, the transcriptional repressor/activator/non-coding RNA regulates the expression of the nucleic acid; wherein binding of the aptamer domains by their respective ligands favors a conformation change in the actuator domains through a strand-displacement mechanism; and, wherein the conformation change affects the activity of the actuator domain to modulate the expression of the transcriptional repressor/activator/non-coding RNA.

In certain embodiments, the nucleic acid is a reporter gene.

In certain embodiments, the device is inside a cell, and the transcriptional repressor/activator/non-coding RNA is endogenous or exogenous to the cell.

In certain embodiments, the subject device includes a polyadenylate tail, or in the case of the expression constructs, a coding sequence that when transcribed, produces a poly-A tail on the transcript. It will be appreciated by those skilled in the art that the subject constructs can be derived from various nucleotides and nucleotide analogs, as well as utilizing various linkage chemistries, such as may be adapted for use in the present invention from the art of antisense and siRNA constructs. To further illustrate, the subject device can include one or more non-naturally occurring nucleoside analogs and/or one or more non-naturally occurring backbone linkers between nucleoside residues. Such analogs and linkers can be used to alter the stability, nuclease susceptibility (or resistance) and/or bioavailability (such as cell permeability) relative to a corresponding nucleic acid of naturally occurring nucleosides and phosphate backbone linkers.

Certain embodiments provide tissue- or cell type-specific modulation of the concentration and/or activity of a ligand or the expression of a target gene. Such regulation may be used to effect cell- or tissue-specific regulation of phenotypes such as viability, proliferation, etc. The tissue- or cell type-specific modulation may be achieved by the tissue- or cell type-specific presence of the ligand. For example, the aptamer domain of a signal processing device may be responsive to a tissue or cell type-specific ligand and the effector domain targets a ligand to modulate the concentration and/or activity of the ligand. In another aspect, the aptamer domain of a signal processing device is responsive to a tissue or cell type-specific ligand and the actuator domain targets a target gene to modulate the expression of the target gene.

The embodiments and practices of the present invention, other embodiments, and their features and characteristics, will be apparent from the description, figures and claims that follow, with all of the claims hereby being incorporated by this reference into this Summary.

It is contemplated that any embodiments described herein, including those only described under one of the many aspects of the invention, can be combined with any other embodiments described under any aspects of the invention whenever appropriate.

BRIEF DESCRIPTION OF THE DRAWINGS

FIGS. 27A-27H show the functions and sequences of several representative devices used in Examples (SEQ ID NOs: 10-63, respectively, in order of appearance). Formatting schemes in the sequences correspond to those in the schematic device diagrams: black box, catalytic core of the ribozyme or actuator component; gray box, loop regions of the actuator component; outlined, aptamer or sensor component; bold text and dashed underline, strands within the transmitter component that participate in the competitive hybridization event, respectively; gray text, strands within the transmitter component that participate in a helix slipping event; italicized, spacer sequences; double underlined, restriction sites.

Figure 1:
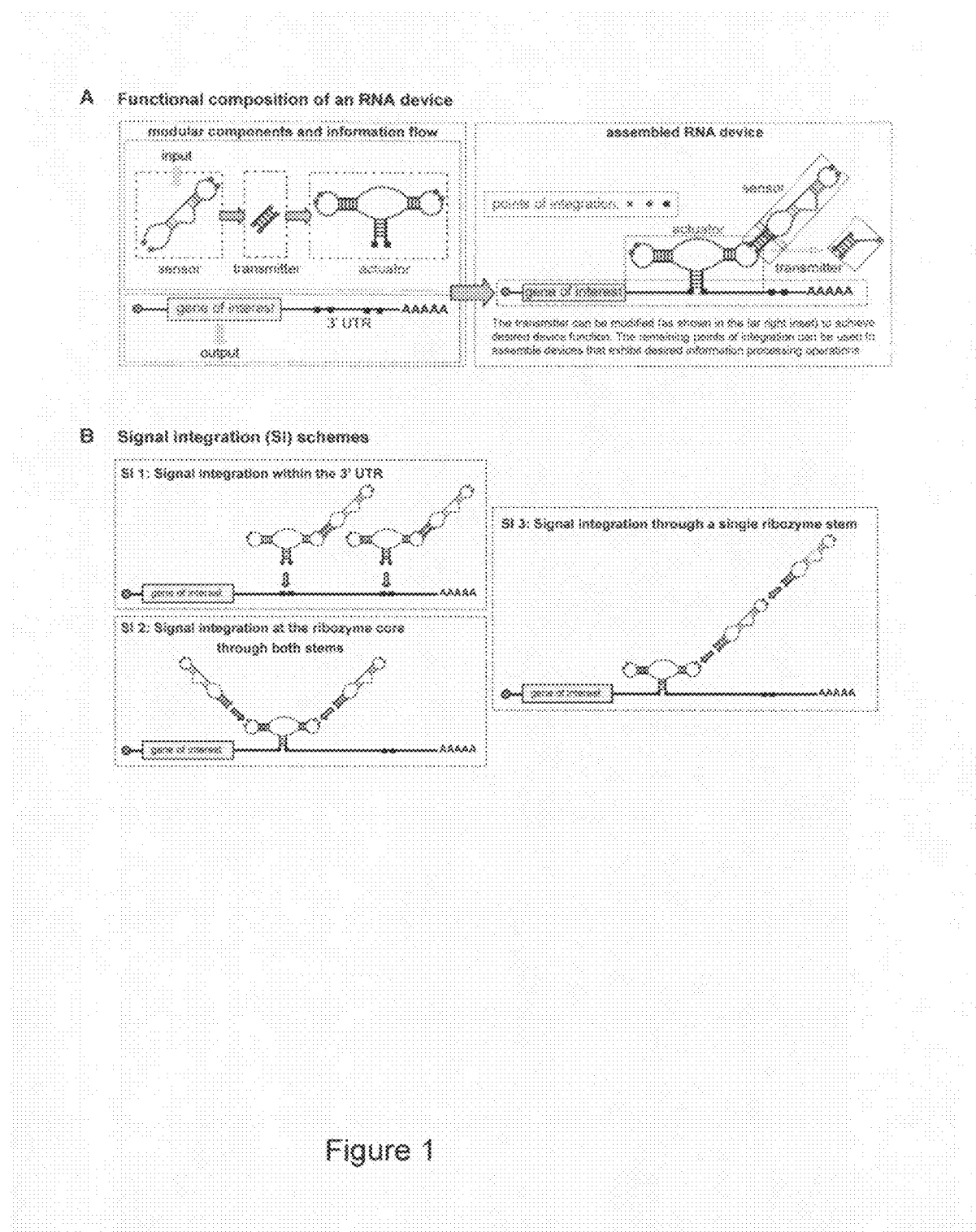
FIG. 1 shows an exemplary functional RNA device composition framework. Shown in the figures are the following functional domains: aptamer or sensor domain/component; catalytic core of the ribozyme or actuator domain/component; loop regions of the actuator domain/component; strands within the transmitter domain/component that participate in the competitive hybridization event (e.g., competing strand and switching strand). (A) A functional composition framework for assembling RNA devices from modular domains/components. Information in the form of a molecular input is received by the sensor and transmitted by the transmitter to a regulated activity of the actuator, which in turn controls the translation of a target transcript as an output. (B) Three signal processing/integration schemes represent different domain/component assembly strategies to build higher-order RNA devices. The RNA device in SI 1 involves multiple actuator domains/components controlled by single sensor-transmitter domains/components, whereas those in SI 2 and 3 involve multiple sensor-transmitter domains/components controlling a single actuator domain/component.

Table 1 shows the basal output signals and device signals of the RNA devices studied over the full transcriptional range of the employed promoter. The predicted basal output signals of coupled devices based on the appropriate single-input gate response(s) and independent function are also reported. Predicted signals that do not match the measured output signals are indicated in italics.

Table 2 lists the free energy changes associated with RNA devices composed of internal Buffer and Inverter gates and associated Hill coefficients. Free energy changes between RNA device states are predicted from a standard RNA folding program, RNAStructure4.2.

DETAILED DESCRIPTION OF THE INVENTION

1. Overview

The invention provides a general approach for engineering RNA devices that can execute higher-order cellular information processing operations, and certain RNA devices constructed based on the approach.

Higher-order information processing represents a significant advance from single-input RNA devices, in which a molecule such as a riboswitch (e.g., a ribozyme-based aptamer-regulated nucleic acid) controls gene expression in response to specific ligand concentrations. Single-input devices function by coupling a distinct sensor domain that binds to a specific ligand (or related ligands) with a separate actuator domain that performs the gene regulatory tasks. In these devices, ligand binding favors a conformation change of the sensor domains, which in turn determines whether the actuation domain will be in a more active or a less active/inactive state.

In contrast, higher-order integrated RNA devices achieve more sophisticated signal processing schemes that integrate more inputs and mediate complex interactions of inputs. Such integrated RNA devices may sense the status of several biological inputs in a complicated system, and produce an output either to indicate the detected status of the inputs, or to affect one or more related or unrelated biological activities. For example, based on the status of the various input signals, the subject signal processing/integration devices may affect the status of one or more inputs themselves to generate a feedback control.

More specifically, the subject integrated RNA devices can be engineered to combine a variety of molecular signals, such as the presence/absence or concentration of specific ligands, to direct ON (e.g., a more active or more functional state) or OFF (e.g., a less active or less functional state) activity to certain gene targets. Due to the flexibility of the subject devices, numerous possible regulations can be achieved based on the specific configuration of a particular device. For instance, in some embodiments, a subject higher-order integrated RNA device might exhibit a switch behavior in which binding of one type of ligand would not be sufficient to direct ON activity of the device, but binding of two or more types of ligands would be required to direct ON activity. Conversely, in other embodiments, binding of one type of ligand could direct OFF activity of the RNA device, while binding of two types of ligand would not. Based on the specific configurations, the devices of the invention may be engineered to generate the output signal only when certain input conditions are met (such as requiring the presence of certain ligands, the absence of certain other ligands, and/or a specific concentration range of yet another type of ligand, etc.).

This type of integrated behavior, in which more than one signal is combined to give a single output or multiple outputs, may sometimes be described as various logic gates. A logic gate performs a logical operation on one or more inputs and produces a single output or multiple outputs. The output functions performed by a particular logic gate may identify the logic gate as AND, NOT, NAND, OR, NOR, XOR, or XNOR, etc (see more details below). Depending on their binding properties, higher-order integrated RNA devices can act as various logic gates for a set of molecular inputs.

Several of such higher-order devices may be used in the same system. In some embodiments, each one may have the same construction except for the actuator domain. This allows, for example, one such device to generate a status indicator (e.g., a reporter gene), another such device to use a feedback mechanism to affect one input, yet another such device to affect a second input, etc.

In certain embodiments, integrated RNA devices can also be engineered to act as signal filters. Given inputs from multiple signals, the RNA device can enhance signaling from a desired input and decrease signaling in response to an unwanted signal.

The multiple input signals (e.g., different or identical ligands) may be integrated relatively independent of one another (for example, by binding to different aptamers in an SI 2 type device described below), or may be integrated relatively cooperatively (for example, binding of one ligand to the device changes the affinity of the device for other ligands).

The input signals may be integrated through various signal processing/integration mechanisms. For example, signal integration (SI) can be categorized into at least three schemes, termed signal integration SI 1, SI 2, and SI 3 herein (infra). Within each scheme, various logic operations can be achieved by altering the function or input responsiveness of the components in each device.

More specifically, in certain embodiments, signals may be processed/integrated using multiple single-input devices, which can be incorporated into the 3' UTR of a coding sequence (such as a target gene), such that the RNA device modulates the coding sequence/target gene expression in a cis-acting mechanism. By "cis-acting," it is meant that the devices of the present invention exert their activity on themselves, or on an otherwise heterologous molecule that is covalently linked to the device. Alternatively, in other embodiments, multiple single-input devices may all act in trans to affect a target gene, such as a target gene that offers the system layered architectures. Exemplary target genes may include, without limitation, transcriptional activators or repressors, non-coding RNAs (such as siRNA, miRNA, antisense sequences, etc.), or enzymes whose products (such as metabolites) can serve as an input for other subject devices.

In certain other embodiments, signals may be integrated through the use of multiple modular sensor domains acting on the same modular actuator domains. These multiple modular sensor domains may be acting relatively independent of one another (such as in an SI 2 type device), or may be acting together (such as in an SI 3 type device).

Regardless of the specific integration mechanism used, the subject RNA device can either act in cis (for example, within the 3' UTR of a target gene), or in trans to mediate the device output on a molecule that is not covalently linked to the device. By "trans-acting," it is meant that the devices of the present invention exert their ligand-dependent activity on another molecule (e.g., a nucleic acid) that is different from the device, and not linked through a phosphodiester (or equivalent) backbone linker. Preferably, a trans-acting device is not linked to a target gene at all.

The following descriptions include certain illustrative examples utilizing specific actuator domains in each signal processing/integration mechanism. It should be noted that these different integration mechanisms are not mutually exclusive, and they can be combined with one another to achieve more design flexibility. Further, the described specific device configurations are provided merely for illustration purpose only, but do not encompass all possibilities enabled by the present application. Numerous other embodiments can be readily generated based on the specific needs and the general principles of the invention.

2. Definitions

"Actuator domain" refers to a switch domain that encodes the system control function. In certain embodiments, the actuator domain encodes the gene-regulatory function, and does not include a ribozyme, such as a hammerhead ribozyme.

As used herein, a "bulge" is a sequence of nucleotides that is not paired with another strand and is flanked on both sides by double-stranded nucleic acid sequences. In certain embodiments, a bulge is located within a stem. When a bulge is located within a stem, the nucleotides of the bulge are considered to be part of the stem. In certain embodiments, a stem may comprise more than one bulge. In certain embodiments, one or both strands of the stem contain a bulge.

"Communication module" refers to a sequence element that typically forms an imperfectly paired double-stranded stem that can adopt different base pairs between nucleotides through a "slip-structure" mechanism. A communication module may be a type of information transmission domain that transmits the binding state of the aptamer domain to the adjacent actuator domain through a helix-slipping mechanism. A communication module does not act in a modular fashion with other switch domains.

"Competing strand" refers to the nucleic acid sequence within a strand-displacement domain that is bound to the general transmission region of the switch when the sensor domain is in one conformation, such as the restored conformation (i.e., in the presence of ligand in this hypothetical situation). The competing strand competes for binding with the switching strand, which is initially bound to this transmission region (for example, in the absence of ligand).

"Complementary" refers to a nucleotide or nucleotide sequence that hybridizes to a given nucleotide or nucleotide sequence. For instance, for DNA, the nucleotide A is complementary to T, and vice versa, and the nucleotide C is complementary to G, and vice versa. For instance, in RNA, the nucleotide A is complementary to the nucleotide U, and vice versa, and the nucleotide C is complementary to the nucleotide G, and vice versa. Complementary nucleotides include those that undergo Watson and Crick base pairing and those that base pair in alternative modes. For instance, as used herein for RNA, the nucleotide G is complementary to the nucleotide U and vice versa, and the nucleotide A is complementary to the nucleotide G and vice versa. Therefore, in an RNA molecule, the complementary base pairs are A and U, G and C, G and U, and A and G. Other combinations, e.g., A and C or C and U, are considered to be non-complementary base pairs.

Due to the binding energy differences between different base pairs, the "quality of complementarily" also varies, and may be explored to fine tune the free energy differences between different conformations of the subject regulated polynucleotides. For example, the G-C base pair exhibits the highest binding affinity, and thus is expected to have a higher quality of binding than that of an A-T pair, or a G-U pair, etc. Depending on specific needs, a Watson-Crick base pair may be replace by another (stronger or weaker) Watson-Crick base pair, or a wobble base pair to alter the quality of complementarity of any region in the subject regulated nucleic acid.

A "complementary sequence" is composed of individual nucleotides that are complementary to the individual nucleotides of a given sequence, where the complementary nucleotides are ordered such that they will pair sequentially with the nucleotides of the given sequence. Such a complementary sequence is said to be the "complement" of the given sequence. For example, complements of the given sequence, 5'-ACUAGUC-3', include 3'-UGAUCAG-5' and 3'-UGGACGG-3', among others. In the latter sequence, the third and sixth base pairs are both non-Watson and Crick G/U complementary base pairs.

"Component" and "domain" are used interchangeably to refer to a part of a system that encodes a distinct activity or function.

"Composability" refers to a property of a system that indicates its ability to be composed of components that can be selected and assembled in a modular fashion to achieve a desired system performance. For example, in certain embodiments, composability refers to the ability of the individual domains of the control system to be modularly linked without disrupting their activities.

"Do/does not bind" as used herein to describe aptamer-ligand binding, does not mean that there is absolutely no binding at all. Compared to an aptamer that does bind the ligand (a "binding aptamer"), the $K_{Apt}$ (association constant for binding between ligand and aptamer) for the aptamer that "does not bind" the ligand is at least about 10-fold, 100-fold, 1000-fold or more larger than that of the binding aptamer, and thus its binding affinity for the ligand is at least about 10-fold, 100-fold, 1000-fold or more weaker than that of the binding aptamer.

"Engineering design principle" refers to a required property of a constructed system that enables use by others.

"Framework" refers to a basic conceptual structure that is used to solve a complex product design issue. As used here, the framework is used to reliably design and construct specific instances of RNA switches. The conceptual structure of the subject framework comprises specified engineering design principles and design strategies that enable extensible and reusable system design.

"Helix-slipping domain" refers to a subset of information transmission domains that act through a helix-slipping mechanism. The helix-slipping domain is also referred to as the communication module.

"Helix-slipping mechanism" refers to an information transmission mechanism that is based on an information transmission domain that functions through a helix-slipping event and does not allow for rational design. Such a helix-slipping event uses a communication module (or helix-slipping domain) within the general transmission region of the switch (e.g., the base stem of the aptamer) to result in disruption or restoration of the actuator domain in response to restoration of the sensor domain.

"Information transmission domain" refers to a switch domain that encodes the function of transmitting information between the sensor domain and the actuator domain.

"Information transmission mechanism" refers to a general mechanism for transmitting information between the sensor domain and the actuator domain of a switch. In certain embodiments, this mechanism regulates the activity of the actuator domain in response to the binding state of the sensor domain.

"Loop" refers to a sequence of nucleotides that is not paired with another strand. In certain embodiments, a loop is between 1 to 20 nucleotides long, 2-10 nucleotides long, or 3-8 nucleotides long.

"Modular" refers to a property of a system composed of modules that indicates whether the modules can by interchanged as parts without changing the interface between modules or the modules themselves.

"Module" refers to a self-contained system component that has a well defined interface with other system components.

"Nucleotide" refers to naturally- and non-naturally-occurring nucleotides and nucleotide analogs. Nucleotides include, but are not limited to, adenosine, cytosine, guanosine, thymidine, uracil, 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine.

"Nucleic acid," "nucleic acid sequence," "nucleic acid molecule," and "polynucleotide" refer to a DNA sequence or analog thereof, or an RNA sequence or analog thereof. Nucleic acids are formed from nucleotides, including, but not limited to, the nucleotides listed above.

"Platform" refers to a general framework on which specific applications can be implemented. In certain embodiments, the platform enables specific instances of switches to be built in a standardized manner.

"Portability" refers to a property of a system that indicates its ability to be implemented in environments different from that in which it was originally designed. In certain embodiments, portability refers to the ability of the control system to be implemented in different organisms.

"Reliability" refers to a property of a system that indicates its ability to perform and maintain its functions under a set of specified conditions. In certain embodiments, reliability refers to the ability of the information transmission domain to standardize the transmission of information between the sensor and actuator domains.

"Scalability" refers to a property of a system that indicates its ability to handle increasing work. In certain embodiments, scalability refers to the ability of the control system to be implemented across broad application space by being able to forward design its response to different molecular information.

A "stem" is a double-stranded nucleic acid motif formed by inter- or intra-molecular base pairing, which may or may not include mismatched base pairs or "bulges." In certain embodiments, a stem comprises 2 to about 40, or 2 to about 20 complementary base pairs. In certain embodiments, a stem comprises 3, 4, 5, 6, 7, 8, 9, 10, 11, 12, 13, 14, 15, 16, 17, 18, 19, 20, or 21 complementary base pairs.

In certain embodiments, at least 30% of the nucleotides in a stem are part of a complementary base pair. The remaining base pairs may be mismatched, non-complementary base pairs, or may be part of a bulge. In certain embodiments, at least 40%, 50%, 60%, 70%, 80%, 90%, 95%, 99%, or 100% of the nucleotides in the stem are part of a complementary base pair.

"Switch" refers to a molecule that can adopt at least two different conformational states, where each state is associated with a different activity of the molecule. Often a ligand can bind to one or more conformations of the switch, such that the presence of the ligand shifts the equilibrium distribution across the adoptable conformations and therefore regulates the activity of the switch molecule. In certain embodiments, switch refers to an RNA molecule that can adopt different structures that correspond to different gene regulatory activities. An RNA switch is an exemplary embodiment of the subject ligand-controlled gene-regulatory system.

"Switch domain" refers to a component of a switch that encodes a distinct activity or function.

"Switching strand" refers to the nucleic acid sequence within a strand-displacement domain that is bound to the general transmission region of the switch when the sensor domain is, for example, in the disrupted conformation (i.e., in the absence of ligand in this hypothetical situation). The switching strand is displaced by the competing strand in, for example, the presence of ligand (in this hypothetical situation).

"Sensor domain" refers to a switch domain that encodes a ligand-binding function. In certain embodiments, the sensor domain comprises an RNA aptamer sequence.

"Strand-displacement domain" refers to a subset of information transmission domains that act through a strand-displacement mechanism.

"Strand-displacement mechanism" refers to an information transmission mechanism that is based on the rational design of an information transmission domain that functions through a strand-displacement event. Such a strand-displacement event uses competitive binding of two nucleic acid sequences (e.g., the competing strand and the switching strand) to a general transmission region of the switch (e.g., the base stem of the aptamer) to result in disruption or restoration of the actuator domain in response to restoration of the sensor domain.

"Universal" refers to a system property that indicates its ability to maintain function across different applications, environments, and component interfaces. In certain embodiments, a universal system is composed of the five engineering design principles (scalability, portability, utility, composability, and reliability) and results in the specified extensible platform for RNA switch construction.

"Utility" refers to a property of a system that indicates its ability to be of practical use. In certain embodiments, utility refers to the ability of the control system to interface with different functional level components to enable forward design of the function that is being controlled by the system.

Other terms used herein and in the claims adopt their plain meanings as would have been understood by one of skill in the relevant art, that are not inconsistent with the usages in the instant specification.

3. Signal Integration (SI) Schemes

The invention provides a composition framework for constructing integrated RNA devices. Like their single-input counterparts, these RNA devices are based on the assembly of various functional components comprising modular domains.

A simple single-input device may comprise: (1) a sensor domain, such as an RNA-based aptamer, (2) an actuator domain, and (3) an information transmission domain (ITD) that functionally couples the modular aptamer and actuator domains. In such a device, a molecular input can be converted to increased or decreased gene expression output.

The subject integrated RNA devices, meanwhile, can be constructed from multiple functional components in combination, such as including two or more aptamer domains and one or more actuator domain(s). For example, in some embodiments, several single-input RNA devices can be directly combined. Alternately, information transmission-sensor components may be coupled to one another, or coupled to different regions of the actuator domain.

To illustrate the points, the following sub-sections provide details about three different signal integration mechanisms, each using specific examples of the various actuator domains.

Signal Integration Scheme 1 (SI 1)

According to SI 1, the subject integrated RNA devices are assembled from two or more independent single-input devices, each of which acts as an input gate within the integrated device. Each individual input gate is preferably designed such that it can adopt at least two conformations. In one conformation, the aptamer domain is capable of binding to a ligand, and the actuator domain may resume one activity state (e.g., more active state or less active state). In the other conformation, the aptamer domain is incapable of binding to the ligand, and the actuator domain may resume another activity state. The conformation change of the aptamer domain may be transmitted through the information transmission domain (ITD) to the coupled actuator domain, so that the actuator domain adopts one of the two activity states depending on whether the aptamer domain does or does not bind to the ligand.

When individual input gates are combined into an integrated RNA device, the integrated device performs functions that reflect the properties of the component pieces. According to the SI 1 scheme, an RNA device could consist of two or more input gates, such as two or more single-input gates, that are aligned in tandem, and covalently linked to the 3' UTR of a target gene. Such a configuration provides a regulation to the target gene linked in cis.

Alternatively, also according to the SI 1 scheme, an RNA device could consist of two or more input gates, such as two or more single-input gates, each affects the function of a target gene in trans. Preferably, the target gene of the trans embodiment offers the system layered architectures. Exemplary target genes may include, without limitation, transcriptional activators or repressors, non-coding RNAs (such as siRNA, miRNA, antisense sequences, etc.), or enzymes whose products (such as metabolites) can serve as an input for other subject devices.

In both cases, only the integration of signals from each of the input gates directs the activity of the RNA device and, in turn, determines the output of the device (e.g., as measured by expression levels of the target gene).

In an illustrative example, the input gates of an RNA device all adopt a conformation in which ligand binding to two or more aptamer domains causes the actuator domains to become inactive. When inactive, the exemplary actuator domains do not function to repress expression of the target gene. If the aptamer domains of each input gate all bind to the same ligand, then the concentration of ligand determines the output of the device. If the aptamer domains bind to different ligands, however, then the presence of only one type of ligand alone would not result in sufficient inactivation of all actuator domains in the device. The output, measured as gene expression, would remain low. Only when all types of ligand for which the aptamer domains bind are present would the RNA device show sufficient inactivation of the actuator domains, and a correspondingly strong output of high gene expression. This example illustrates how the RNA device must bind to two independent ligands and undergo conformational changes in both actuator domains before the overall output of the device can be affected.

Figure 2:
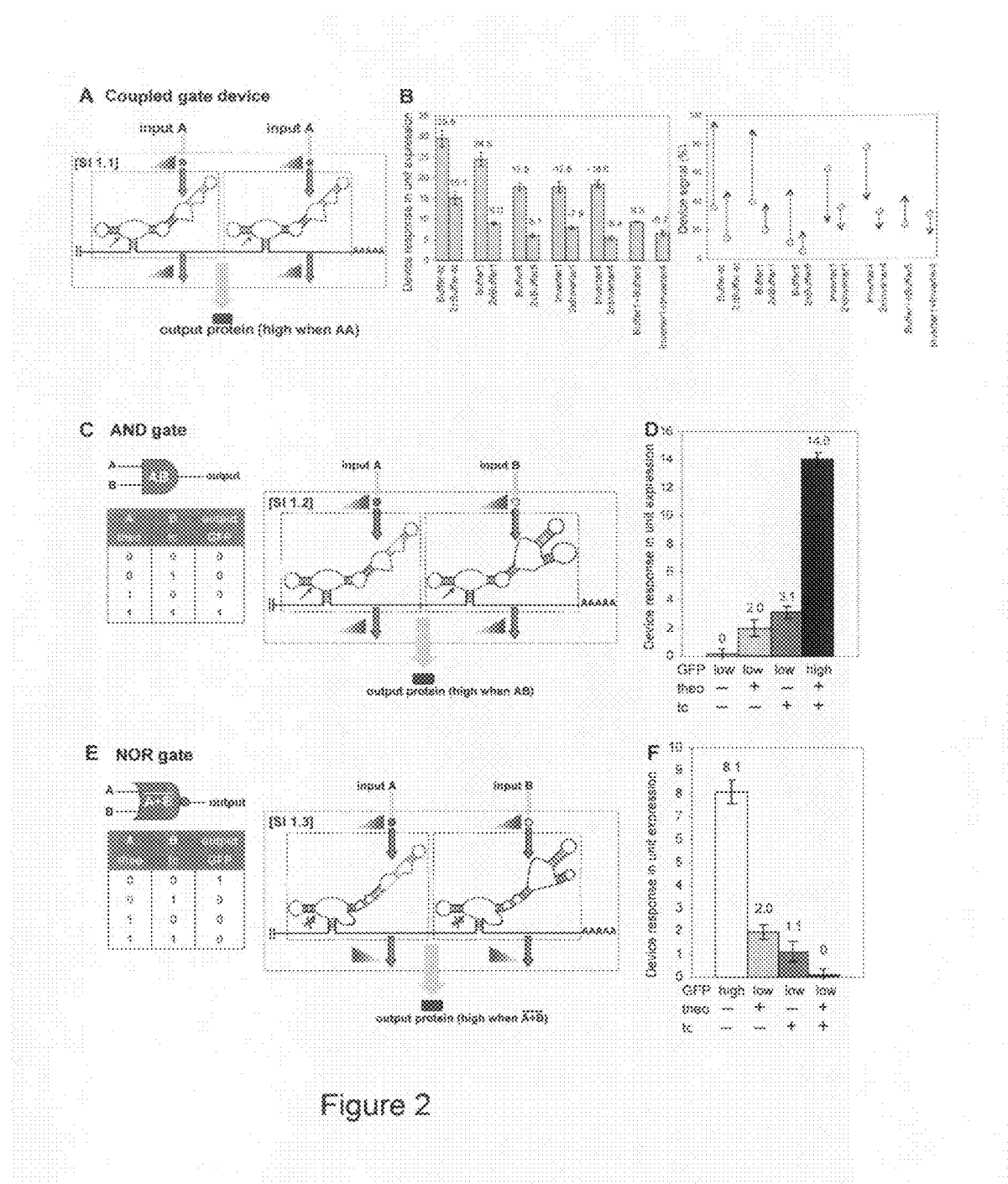
FIG. 2 shows RNA devices based on signal processing/integration within the 3' UTR (SI 1). Single-input gates are indicated in dashed boxes, and triangles indicate relationships between associated gate inputs and outputs. (A) An RNA device composed of two Buffer gates responsive to the same input functions to shift the device response lower than that of the single-input gate. (B) The device output of RNA devices composed of two single-input gates and their single-input gate counterparts. Device response (bars) is reported as the difference between gene expression activities in the absence and presence of the appropriate inputs (10 mM theophylline or 1 mM tetracycline). Device signal (arrows) is reported over the full transcriptional range of the employed promoter system as a percentage of the expression activity relative to that of an inactive ribozyme control, where circles and arrowheads indicate device signals in the absence and presence of input, respectively. The negative sign indicates the down-regulation of target gene expression by the Inverter gates. (C) An RNA device that performs an AND operation by coupling two Buffer gates responsive to different inputs and the associated truth table. (D) The device response of an AND gate (L2bulge1+L2bulge1tc). Device response under different input conditions (theo or tc (−), 0 mM; theo (+), 5 mM; tc (+), 0.25 mM) is reported as the difference between expression activity in the absence of both inputs and that at the indicated input conditions. (E) An RNA device that performs a NOR operation by coupling two Inverter gates responsive to different inputs and the associated truth table. (F) The device response of a NOR gate (L2bulgeOff1+L2bulgeOff1tc). Device response under different input conditions (theo or tc (−), 0 mM; theo (+), 10 mM; tc (+), 0.5 mM) is reported as the difference between expression activity in the presence of both inputs and that at the indicated input conditions.

A schematic drawing showing a representative cis SI 1 device is depicted in FIG. 1B. More specifically, in FIG. 1B, two input gates are arranged in tandem, and signal integration takes place in the 3' UTR of a target gene transcript. Depending on the specific actuator domains in each single-input device and the presence or absence of specific ligand(s), the gene transcript may be stable (or unstable), and the transcription of the gene of interest may be present or absent. For example, as shown in FIG. 2C, two ribozyme-based single-input devices ("riboswitch") are arranged in tandem in the 3' UTR of a gene of interest (such as a reporter gene, or an enzyme, etc.). In the absence of ligands, both riboswitches are active, resulting in the self-cleavage of the 3' UTR sequence and degradation of the gene transcript. Only when both ligands are present will the self-cleavage activities of the two riboswitches be abolished, resulting in a stable gene transcript that can express an encoded product. Thus, the device functions as an AND logic gate (e.g., one that generates an "ON" signal only when both input signals are present).

In certain embodiments, more than two single-input devices may be used, such that the device can sense 3, 4, 5, 6, 7, 8, 9, 10, or more input signals.

The ligand-binding/aptamer domains of the single-input devices may be the same or different. For example, the aptamers may bind different ligands, or bind the same ligand with different affinity.

The actuator domains of the single-input devices may be of the same type or different types, and/or may be the same or different from one another. In certain embodiments, all the actuator domains are of the same type (e.g., all ribozyme-based, all siRNA target-based, etc.). In certain embodiments, all actuator domains are the same. In certain embodiments, at least two of the single-input devices have different types of actuator domains (e.g., two ribozyme-based actuators and one siRNA target sequence, etc.).

Any type of actuator domains may be used in the subject invention. Exemplary actuator domains for the input gates include ribozymes, target sequences for siRNA or miRNA, precursors for siRNA or miRNA, RNAse substrates, antisense sequences for target genes, alternative splicing elements or antisense targeting sequences, or coding sequence for any other molecule whose functional activity affects the expression of target gene products. Similarly, each single-input gate could contain aptamer domains that bind to only one ligand, or each input gate could contain aptamer domains that each bind to different ligands.

For example, a hammerhead ribozyme may be the actuator domain, wherein ligand binding to an aptamer linked through loop 1, loop 2, or stem 3 of the hammerhead ribozyme may favor a conformation change to either disrupt or restore the catalytic core of the hammerhead ribozyme. The hammerhead ribozyme may have self-cleavage activity for the cis-regulatory embodiments of the invention, and may cleave a different nucleic acid in trans for the trans-regulatory embodiment of the invention.

Similarly, a target sequence for an siRNA/miRNA/antisense may be used as the actuator domain of the subject invention. For example, for each single-input device, ligand binding may favor a conformation change that exposes (or hides via alternative intramolecular competing hybridization) an siRNA/miRNA/antisense target sequence. Each of the target sequences for siRNA/miRNA/antisense may be cleaved by an siRNA/miRNA constitutively present, or may be targeted by an antisense sequence that is constitutively present. This in turn modulates the expression of the gene of interest linked in cis.

In other embodiments, the actuator domain may be an siRNA/miRNA precursor or RNase III substrate. For example, for each single-input device, ligand binding may favor a conformation change that exposes (or hides via alternative intramolecular competing hybridization) the siRNA/miRNA precursor sequence or RNase III substrate sequence. Each siRNA/miRNA precursor sequence or RNase III substrate sequence can be cleaved by Dicer and/or Drosha to produce siRNA/miRNA. Such siRNA/miRNA may target any gene transcript, including the gene of interest linked in cis or the gene of interest in trans.

Similarly, any of the other suitable actuator domains, including antisense sequences, alternative splicing elements, or antisense targeting sequences may also be used in the present invention.

Devices designed based on the SI 1 scheme may perform numerous logic operations, such as AND (e.g., a positive output signal is present only when all input signals are present) or NOR (e.g., a positive output signal is present only when all input signals are absent) logic operations. Such devices may also process layers of outputs to obtain NAND (e.g., a positive output signal is always present except when all input signals are present) and OR (e.g., a positive output signal is always present except when all input signals are absent) logic operations, and act as signal and bandpass filters (e.g., a positive output signal is present only when the input signal is within a certain concentration range).

Figure 8:
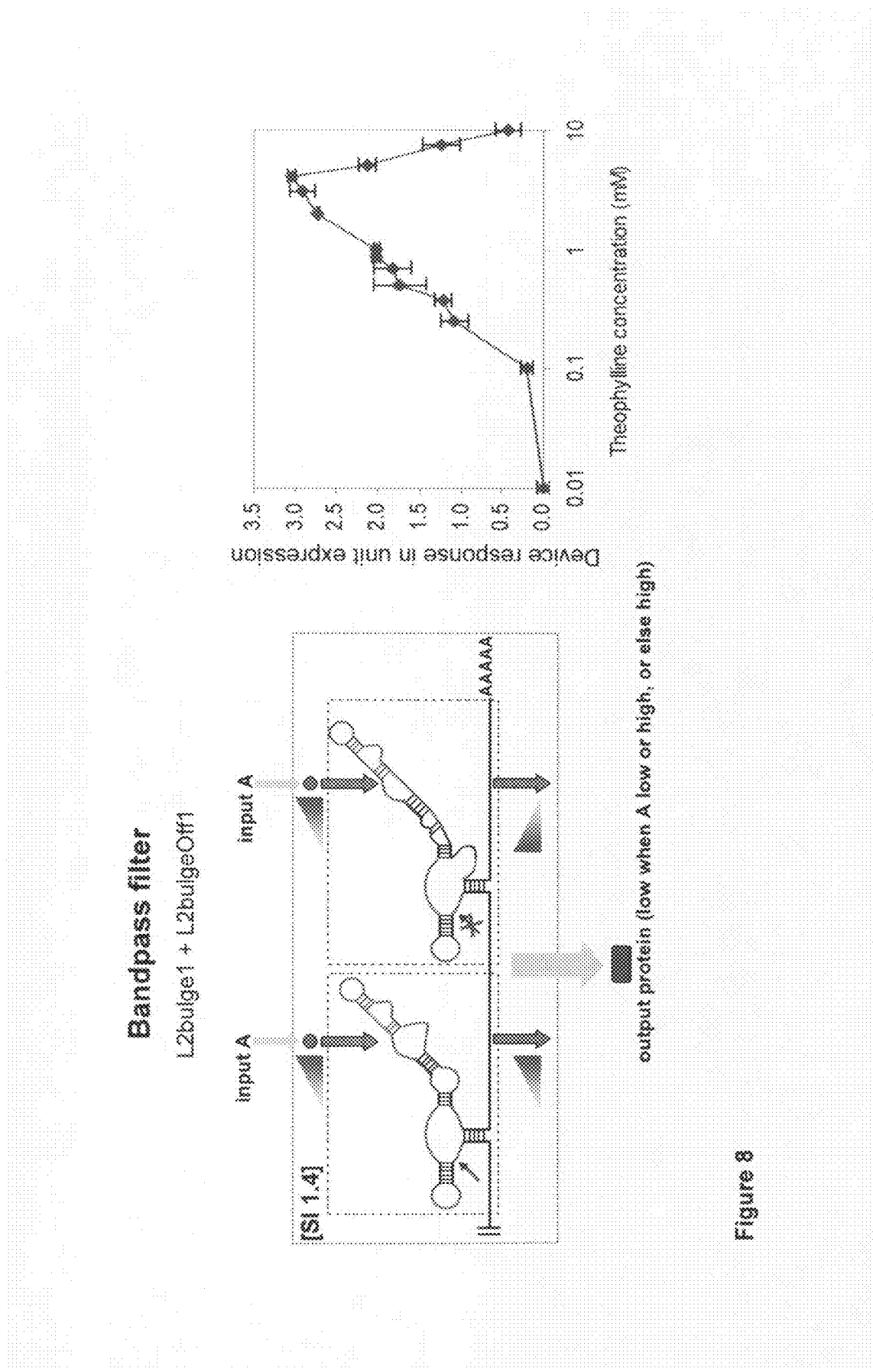
FIG. 8 is a schematic representation and device response of a bandpass filter (L2bulge1+L2bulgeOff1) based on SI 1.4. Single-input gates are indicated in dashed boxes, and triangles indicate relationships between associated gate inputs and outputs. The RNA device is constructed by coupling a theophylline-responsive Buffer gate (L2bulge1) and a theophylline-responsive Inverter gate (L2bulgeOff1) in the 3' UTR of a target transcript. Device response is reported as the difference between expression activities in the absence and presence of theophylline.

For example, FIG. 8 provides an exemplary bandpass filter design, wherein two different ribozyme-based single-input devices are arranged in tandem in the 3' UTR of a gene of interest. In this specific design, both aptamers bind the same ligand/input A (such as theophylline), although different ligands may be used as well, and the two aptamers do not necessarily have the same binding affinity for the same ligand. One of the single-input devices is a so-called Buffer gate where ligand binding favors inactivation of the ribozyme self-cleavage. The other single-input device is a so-called Inverter gate where ligand binding favors activation of the ribozyme self-cleavage. Therefore, when the ligand concentration is very low or very high, one of the single-input devices has a fully active ribozyme actuator domain, resulting in the self-cleavage of the transcript in cis. Only when the ligand concentration is within a certain range will both single-input devices have relatively inactive ribozyme actuator domains, resulting in a certain level of transcription of the gene product.

In another illustrative example, the RNA device of SI 1 could be engineered to function as a NOR device (see, for example, FIG. 2E). In this specific case, the aptamer domains of the input gates would adopt a conformation in which the absence of all ligands causes the actuator domains (both self-cleavage ribozymes) to become inactive (which leads to a positive output signal, such as gene expression). If each aptamer domain in the device binds different ligands, then the presence of only one of the ligands will activate one of the actuator domains in the device, and the output of the system will reflect actuator domains in the active conformation. As a result, gene expression levels would be low. In the presence of both ligands, both actuator domains will be active, and the output of the system will remain low. In order to achieve high levels of target gene expression, all actuator domains would have to adopt the inactive conformation, which requires that all aptamer domains remain unbound to their respective ligands.

Additional devices that demonstrate diverse information processing operations can be assembled through SI 1. Operations such as NAND and OR can be generated if the output of an AND or NOR device is expression of a so-called inverter. The output of an exemplary inverter device would be a repressor protein or an inhibitory non-coding RNA (siRNA/miRNA precursor or RNase III substrate, antisense sequence, etc.). The repressor or inhibitor would act in trans, on a separately encoded gene product. This process is illustrated in a device similar to that described above, where the binding of all ligands to the aptamers directs the actuator domains to the inactive conformation, thus permitting the output activity, or expression of the target gene, to remain high. If the target gene encoded a repressor protein specific to a separately encoded gene product, then the overall effect would be repression of the gene product. With reference to the separately encoded gene product, the device performs a NAND operation, because the presence of all, but not just one, of the ligands led to a repression of the gene product (see, for example, FIG. 24). Conversely, a device could perform an OR operation through repression of a separately encoded gene product. In this case, the absence of all ligand would direct all of the actuator domains to their inactive conformations, while the presence of any one ligand would direct at least one actuator domain to the active conformation. If the active conformation prevented expression of the target gene, and the target gene encoded the repressor of a separately encoded gene product, then the repression of the gene product would not occur. Thus, the presence of one ligand or additional ligands means that the actuator domains adopt an active conformation, the device output remains low, and expression of the separately encoded gene product is high. Such a device would perform an OR logic operation. Both NAND and OR devices generated according to this scheme are examples of layered architecture, in which AND and NOR operations within a device have been inverted with respect to a separately encoded gene product.

In certain embodiments, each input gate may also be designed such that the actuator and aptamer domains are coupled by an information transmission domain (ITD) that uses a strand-displacement mechanism. Such a mechanism uses competitive binding of two nucleic acid sequences to a general transmission region of the switch to result in disruption or restoration of the actuator domain in response to restoration of the aptamer domain. Moreover, a further feature of a specific embodiment of the ITD is that the switching strand and competing strand of the ITD are linked as a contiguous sequence in a subject device (e.g., the switching strand may be within a loop structure in at least one conformation of the sensor domain-regulated nucleic acid, and does not have a free 5'-OH or 3'-OH group; or the switching strand and competing strand of the ITD are linked to both the aptamer domain and actuator domain, etc.). This design feature eliminates any free-floating ends of the switching strand, thereby improving the kinetics of strand-displacement.

Signal Integration Scheme SI 2

According to SI 2, the subject integrated RNA devices are assembled to integrate two or more signals/ligand binding to a single actuator domain. Such integration may be achieved through the use of ITDs that modularly couple two or more aptamer domains to the actuator domain.

A schematic drawing showing a representative cis SI 2 device is depicted in FIG. 1B. More specifically, in FIG. 1B, one aptamer domain is modularly coupled to loop 1 of a hammerhead ribozyme, and a second aptamer domain is modularly coupled to loop 2 of the hammerhead ribozyme. This aptamer-regulated ribozyme is integrated to the 3' UTR of a target gene transcript (cis embodiment). Depending on the specific design of the ITD, and the presence or absence of specific ligand(s) that can be bound by the aptamers, the gene transcript may be stable (or unstable), and the transcription of the gene of interest may be present or absent.

The same structure can be adapted for use with a target gene transcript in trans.

Figure 25:
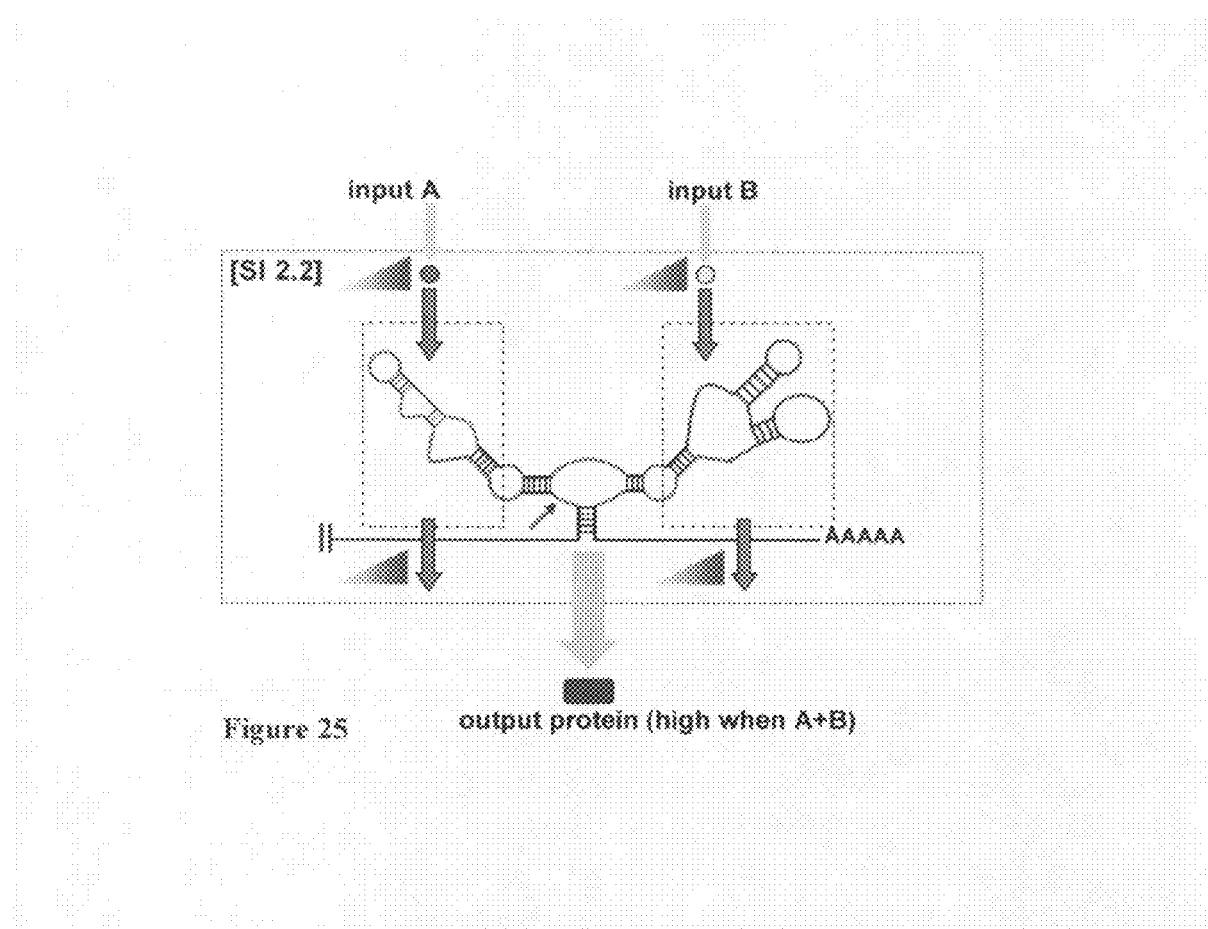
FIG. 25 is a schematic representation of an RNA device based on SI 2 that functions as an OR gate.

For example, for a ribozyme-based cis SI 2 type device as shown in FIG. 25, the device can be configured such that in the absence of both ligands, the riboswitch is active, resulting in the self-cleavage of the 3' UTR sequence and degradation of the gene transcript. When at least one of the ligands is present, however, the catalytic core of the ribozyme is disrupted, resulting in stabilization of the gene transcript and the expression of the gene product. Thus, the presence of either ligand is sufficient to disrupt actuator domain function, resulting in expression of the gene in cis. Only when both ligands are absent will the self-cleavage activities of the riboswitch be restored, resulting in a degradation of the gene transcript that can express an encoded product. In that configuration, the device functions as an OR logic gate (e.g., one that generates an "ON" or a positive signal when either or both input signals are present).

In certain embodiments, more than two aptamers may be used in the SI 2 type device. For example, for a ribozyme-based actuator domain, two or more aptamers may be linked in tandem, and only the most proximal aptamer is directly coupled to loop 1, loop 2, or stem 3 (see SI 3). Thus, in certain embodiments, the device can sense 3, 4, 5, 6, 7, 8, 9, 10, or more input signals.

In certain embodiments, two or more SI 2 type devices may be arranged in tandem in the 3' UTR of the gene transcript, similar to that of a cis SI 1 type device. In this arrangement, the actuator domains of the SI 2 type devices may be of the same type or different types, and/or may be the same or different from one another. In certain embodiments, all the actuator domains are of the same type (e.g., all ribozyme-based, all siRNA target-based, etc.). In certain embodiments, all actuator domains are the same. In certain embodiments, at least two of the SI 2 type devices have different types of actuator domains (e.g., two ribozyme-based actuators and one siRNA target sequence, etc.).

The ligand-binding/aptamer domains of the SI 2 type devices may be the same or different. For example, the aptamers may bind different ligands, or bind the same ligand with different affinity.

Many types of actuator domains may be used in the subject invention. Exemplary actuator domains for the input gates include ribozymes, target sequences for siRNA or miRNA, precursors for siRNA or miRNA, RNase substrates, antisense sequences for target genes, alternative splicing elements or antisense targeting sequences, or coding sequence for any other molecule whose functional activity affects the expression of target gene products.

Similarly, the aptamer domains in the SI 2 type device may bind specifically to only one ligand, or bind related but different ligands (with different affinities).

For example, a hammerhead ribozyme may be the actuator domain, wherein ligand binding to an aptamer linked through loop 1, loop 2, or stem 3 of the hammerhead ribozyme may favor a conformation change to either disrupt or restore the catalytic core of the hammerhead ribozyme. The ribozyme may have self-cleavage activity useful for in cis regulation, or may cleave a target gene transcript in trans.

Similarly, a target sequence for siRNA/miRNA/antisense may be used as an actuator domain of the subject SI 2 type device. For example, for each half of a subject SI 2 type device, ligand binding may favor a conformation change that exposes (or hides via alternative intramolecular competing hybridization) an siRNA/miRNA/antisense target sequence. Two such half devices may be arranged in tail-to-tail fashion, such that when both target sequences are exposed, a continuous target sequence results, which may be cleaved by an siRNA/miRNA constitutively present, or may be targeted by an antisense sequence that is constitutively present. This in turn modulates the expression of the gene of interest linked in cis.

In other embodiments, the actuator domain may be an siRNA/miRNA precursor or RNase III substrate. For example, for each half of a subject SI 2 type device, ligand binding may favor a conformation change that exposes (or hides via alternative intramolecular competing hybridization) part of the siRNA/miRNA precursor sequence or RNase III substrate sequence. Two such half devices may be arranged in tail-to-tail fashion, such that when both sequences are exposed, an intramolecular hybridization between these two sequences occurs, forming an siRNA/miRNA precursor sequence or RNase III substrate sequence, which can be cleaved by Dicer to produce siRNA/miRNA. Such siRNA/miRNA may target any gene transcript, including the gene of interest linked in cis or the gene of interest in trans.

Similarly, any of the other suitable actuator domains, including antisense sequences, alternative splicing elements, or antisense targeting sequences may also be used in the present invention.

Devices designed based on the SI 2 scheme may also perform numerous logic operations, such as NAND (supra) or OR (supra) logic operations. Such devices may also process layers of outputs to obtain AND (supra) and NOR (supra) logic operations.

For example, in certain embodiments, the subject SI 2 type devices can perform NAND and OR logic operations through an assembly scheme that does not rely on the use of an inverter. The information transmission-sensor components, also called internal gates, may fall into one of two categories: interval Inverter gates and internal Buffer gates, based on their activity in the presence of input. Input, such as the presence of a ligand, causes Inverter gates to activate components that are coupled to it, while Buffer gates inactivate coupled components in the presence of ligands. Integration and activation through all of the internal gates in an RNA device of SI 2 controls the output of the assembled device.

In one embodiment of an SI 2 type RNA device, internal gates act independently of one another, such that their messages must be integrated and computed within the single actuator domain to which they are both linked. The actuator domain, in turn, controls activity of a target gene to which the RNA device is covalently linked. Thus, activity of the target gene depends on the state of the internal gates and the integration by the actuator domain. In this configuration, the single actuator domain is only in the active state, corresponding to low device output, when all internal gates are in states that activate the actuator.

In one illustrative example, two or more aptamer domains are each linked through internal Buffer gates to one actuator domain. Because the Buffer gates inactivate coupled components in the presence of their respective inputs, the actuator domain adopts the inactive conformation when all of the aptamer domains have bound to their respective ligands, and adopts the active conformation only when none of the aptamer domains have bound to ligand. If the active form of the actuator domain inhibits the expression of a target gene, then the output of the RNA device will be low, corresponding to low expression of the target gene, only when the actuator domain is active. If at least one ligand is present, then the actuator domain will be inactive, and the output of the device will be high. Low output of the device requires that none of the ligands are present and bound to the aptamer domains. Thus, this exemplary device performs an OR logic operation.

Similarly, a NAND logic operation can also be performed by RNA devices in SI 2. For example, two or more aptamer domains can be linked through internal Inverter gates to one actuator domain. The Inverter gates activate coupled components, so the actuator domain adopts the active conformation once the aptamer domains have all bound to their respective ligands. If the active form of the actuator domain in this example, as above, inhibits the expression of a target gene, then the output of the RNA device will be low only when the actuator domain is active. If not all ligands are bound, then the actuator domain remains inactive, and the output of the device as measured by expression of the target gene, remains high. High output is thus observed in the presence of not all ligands, and low output is observed only when all ligands are present. A device with these properties performs a NAND logic operation.

Signal Integration Scheme SI 3

According to SI 3, the RNA devices may comprise multiple aptamer domains linked in tandem, and only the most proximal aptamer is directly linked to the actuator domain, such as through stem-loop 1 or 2, or stem 3 in a hammerhead ribozyme. Each of the information transmission-sensor domains acts as an internal gate (buffer or inverter) within the integrated device. In operation, the most distal aptamer (e.g., the 1st aptamer) may bind its ligand (e.g., ligand 1) and thus favors one conformation over another. This in turn allows or promotes the aptamer directly linked to it (e.g., aptamer 2) to adopt a conformation more amenable to binding its own ligand (ligand 2). Ligand 2 binding to aptamer 2 similarly triggers a change in the ability of the directly linked aptamer 3 to bind ligand 3, etc., until the most proximal aptamer is promoted to bind its own ligand to affect the actuator domain. The conformation changes of the aptamer domains may be transmitted through the information transmission domains (ITDs).

A schematic drawing showing a representative cis SI 3 device is depicted in FIG. 1B. More specifically, in FIG. 1B, two input gates are arranged in tandem, and the signals are integrated through a single ribozyme stem, wherein the ribozyme is incorporated into the 3' UTR of a target gene transcript. Depending on the presence or absence of specific ligand(s), the gene transcript may be stable (or unstable), and the transcription of the gene of interest may be present or absent. Similarly, a trans SI 3 type device comprises an actuator domain that regulates the function of a target gene in trans, such as a target gene that provides layered architect to the system (supra).

Figure 26:
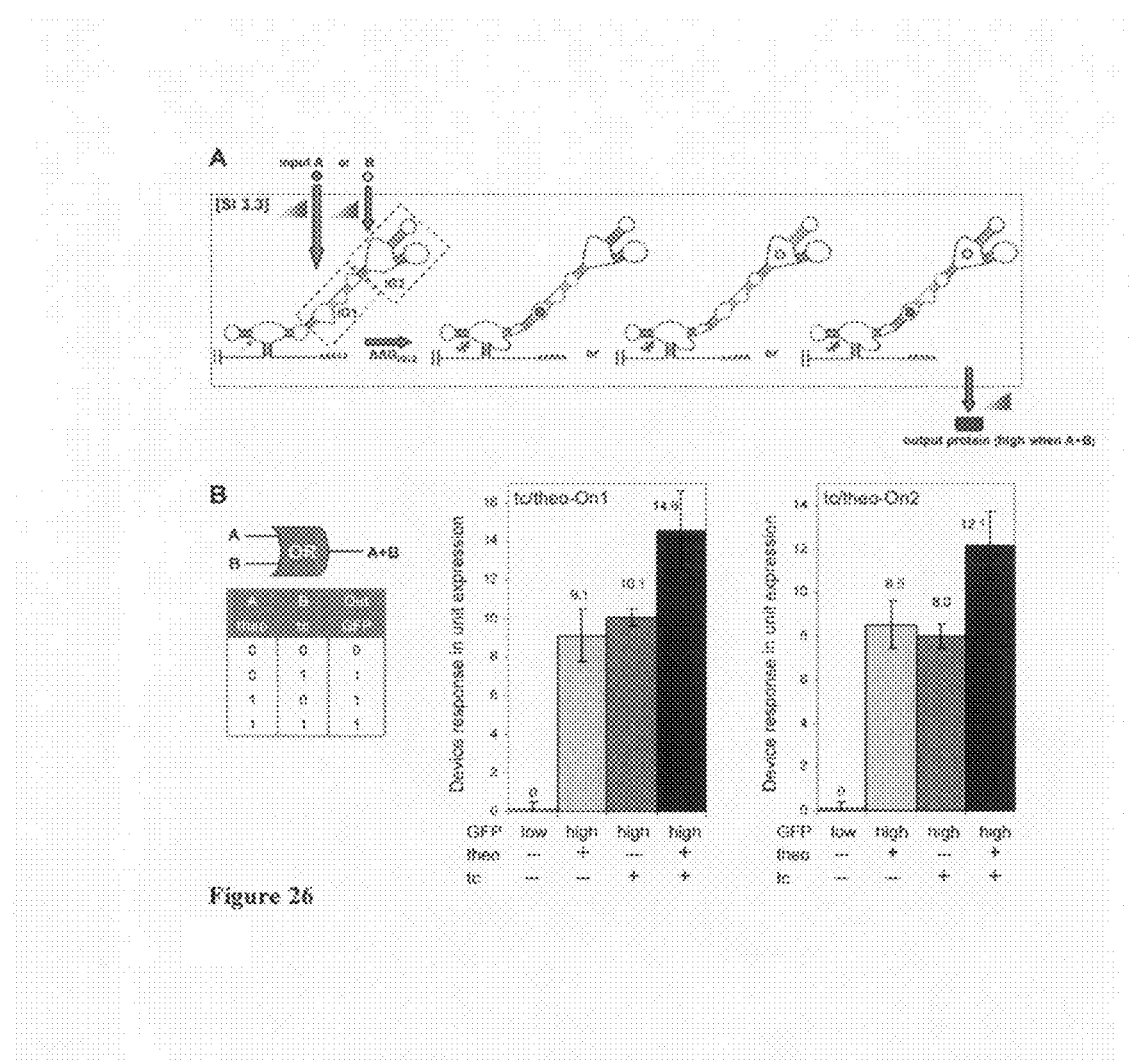
FIG. 26 shows OR gate devices based on SI 3. (A) Schematic representation of an RNA device that performs an OR operation by coupling internal Buffer (IG1) and Inverter (IG2) gates responsive to different input molecules to a single ribozyme stem. (B) The device response and truth table of OR gates (tc/theo-On1 and tc/theo-On2) based on SI 3.3. Device response under different input conditions (theo or tc (−), 0 mM; theo (+), 10 mM; tc (+), 0.25 mM) is reported as the difference between expression activity in the absence of both inputs and that at the indicated input conditions.

For example, a cis SI 3 type device as shown in FIG. 26 may be configured to create an OR gate. Specifically, two aptamers are arranged in tandem in one stem of a ribozyme actuator domain, in which the ribozyme is within the 3' UTR of a gene of interest (such as a reporter gene, or an enzyme, etc.). For this specific OR gate, in the absence of any ligands, the catalytic domain of the ribozyme is active, resulting in the self-cleavage of the 3' UTR sequence and degradation of the gene transcript. Ligand binding to one or both aptamers favors a conformation change in the ribozyme actuator domain, and at least partially destroys its self-cleavage catalytic activity. Thus, the entire transcript becomes stabilized, and can thus express an encoded product.

In certain embodiments, more than two aptamers may be arranged in tandem in a similar fashion, such that the device can sense 3, 4, 5, 6, 7, 8, 9, 10, or more input signals.

The ligand-binding/aptamer domains of a subject SI 3 type device may be the same or different. For example, the aptamers may bind different ligands, or bind the same ligand with different affinity.

Two or more SI 3 type devices may be arranged in tandem like an SI 1 type device. In that case, the actuator domains of each SI 3 type device may be of the same type or different types, and/or may be the same or different from one another. In certain embodiments, all the actuator domains are of the same type (e.g., all ribozyme-based, all siRNA target-based, etc.). In certain embodiments, all actuator domains are the same. In certain embodiments, at least two of the SI 3 type devices have different types of actuator domains (e.g., two ribozyme-based actuators and one siRNA target sequence, etc.).

For any of the SI 3 type devices, an SI 2 type arrangement can also be made to integrate multiple signals. For example, if the actuator domain is a hammerhead ribozyme (see, for example, FIG. 1B), for each of the two stem-loop structures, two or more aptamers may be connected in tandem as in an SI 3 type device. Two or more aptamers may also be similarly connected in tandem such that the signal may be integrated through stem three of a ribozyme-based switch.

Any type of actuator domains may be used in the subject SI 3 type devices. Exemplary actuator domains include ribozymes, target sequences for siRNA or miRNA, precursors for siRNA or miRNA, RNase substrates, antisense sequences for target genes, alternative splicing elements or antisense targeting sequences, etc (supra).

For example, a hammerhead ribozyme may be the actuator domain, wherein ligand binding to aptamers linked through either loop 1 or 2 or stem 3 of the hammerhead ribozyme may favor a conformation change to either disrupt or restore the catalytic core of the hammerhead ribozyme. The ribozyme may in turn affect the function of a target gene in cis or in trans.

Similarly, a target sequence for siRNA/miRNA/antisense may be used as actuator domain of the subject invention. For example, several aptamers may be arranged in tandem in an SI 3 type device, and the most proximal aptamer is directly integrated to the actuator domain. Ligand binding may favor a conformation change that exposes (or hides via alternative intramolecular competing hybridization) an siRNA/miRNA/antisense target sequence, which may be cleaved by an siRNA/miRNA constitutively present, or may be targeted by an antisense sequence that is constitutively present. This in turn modulates the expression of the gene of interest linked in cis.

In other embodiments, the actuator domain may be an siRNA/miRNA precursor or RNase III substrate. For example, several aptamers may be arranged in tandem in an SI 3 type device, and the most proximal aptamer is directly integrated to the actuator domain. Ligand binding may favor a conformation change that exposes (or hides via alternative intramolecular competing hybridization) the siRNA/miRNA precursor sequence or RNase III substrate sequence, which can be cleaved by Dicer to produce an siRNA/miRNA. Such siRNA/miRNA may target any gene transcript, including the gene of interest linked in cis or in trans.

Similarly, any of the other suitable actuator domains, including antisense sequences, alternative splicing elements, or antisense targeting sequences may also be used in the present invention.

Devices designed based on the SI 3 scheme may also perform numerous logic operations, such as AND (supra) or OR (supra) logic operations. Such devices may also process layers of outputs to obtain NAND (supra) and NOR (supra) logic operations.

In certain embodiments, the SI 3 type device may be designed such that any two linked aptamer domains are coupled by an information transmission domain (ITD) that uses a strand-displacement mechanism. Such a mechanism uses competitive binding of two nucleic acid sequences to a general transmission region of the switch to result in disruption or restoration of the coupled components or internal gates, such that it results in activation or inactivation of the coupled components. Moreover, a further feature of a specific embodiment of the ITD is that the switching strand and competing strand of the ITD may be linked together to form a continuous strand. This design feature eliminates any free-floating ends of the switching strand, thereby improving the kinetics of strand-displacement.

Figure 4:
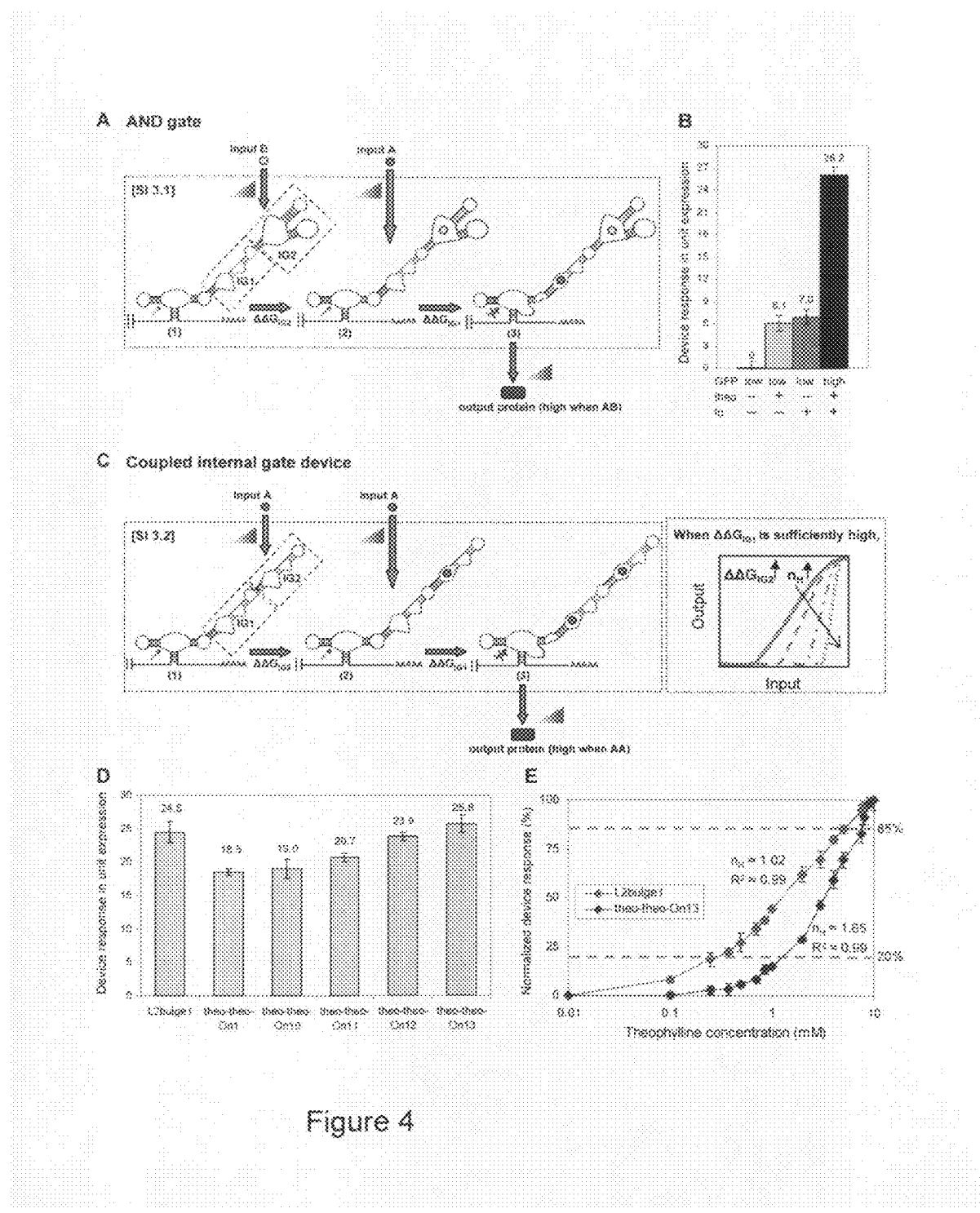
FIG. 4 shows RNA devices based on signal processing/integration at a single ribozyme stem (SI 3). Internal gates (IGn) are indicated in dashed boxes, and triangles indicate relationships between associated internal gate inputs and the device output. (A) An RNA device that performs an AND operation by coupling internal Buffer (IG1) and Inverter (IG2) gates responsive to different inputs to a single ribozyme stem. (B) The device response of an AND gate (tc-theo-On1). Device response under different input conditions (theo or tc (−), 0 mM; theo (+), 2.5 mM; tc (+), 0.5 mM) is reported as in FIG. 2D. (C) An RNA device composed of internal Buffer (IG1) and Inverter (IG2) gates responsive to the same input coupled to a single ribozyme stem. (D) The device response of RNA devices composed of internal Buffer and Inverter gates and their single-internal gate device counterpart (L2bulge1). Device response is reported as in FIG. 2B. Theo-theo-On10-13 exhibit varying degrees of cooperativity, as quantified by Hill coefficients ($n_H$) greater than one (26). (E) The device output response of theo-theo-On13 shows a high degree of programmed cooperativity. The device response is normalized to the response at 10 mM theophylline (21).

In certain embodiments, the linked information transmission-sensor domains in the subject SI 3 type devices function in a cooperative manner, such that binding of ligand I to aptamer 1 facilitates (or antagonizes) binding of ligand 2 to aptamer 2. For example, binding of ligand 1 to aptamer 1 may favor a certain conformation of the linked aptamer 2, which is amenable to binding to ligand 2 (see, for example, FIG. 4E, where the $n_H$ for the cooperative device theo-theo-On13 is 1.65). Cooperativity in biological molecules is often a result of multiple binding sites that transit from a low-affinity state to a high-affinity state as more ligands occupy the available binding sites.

For example, in an SI 3 type RNA device with two internal gates (IG1 and IG2) to the same input (ligand 1 and ligand 2 for binding to IG1 and IG2, respectively), although the sensor components (aptamers) exhibit similar input binding affinities ($K_{apt}$), their effective affinities are a combined effect of the sensor affinity ($K_{apt}$) and the energetic requirements for the device to switch between two states ($K_{IG}$), the latter of which can be programmed into the transmitter component ($\Delta\Delta G_{IG}$) by, for example, altering the base-pairing quality differences between the alternative conformations. Thus, the difference in free energies between state 1 (no ligand binding) and state 3 (both ligands bound), ($\Delta\Delta G_{IG2}+\Delta\Delta G_{IG1}$), represents an energetic contribution which lowers the effective binding affinity of IG1 to its input. The difference in free energies between state 1 and state 2 (only ligand 2 is bound), ($\Delta\Delta G_{IG2}$), represents a lower energetic contribution to the effective binding affinity of IG2 to its input, such that the effective binding affinity of IG2 is higher than that of IG1. However, binding of input to IG2 lowers the energetic contribution to IG1 to the difference in free energies between states 2 and 3 ($\Delta\Delta G_{IG1}$), resulting in an increase in the effective binding affinity of the device as a result of input binding to IG2. The RNA device design is expected to result in a larger change in the device response as input concentrations increase and IG1 transits from a lower affinity state to a higher affinity state. By programming the energetic differences between the different conformational states ($\Delta\Delta G_{IG2}$ and $\Delta\Delta G_{IG1}$), one can program the degree of cooperativity exhibited by the device.

Figure 11:
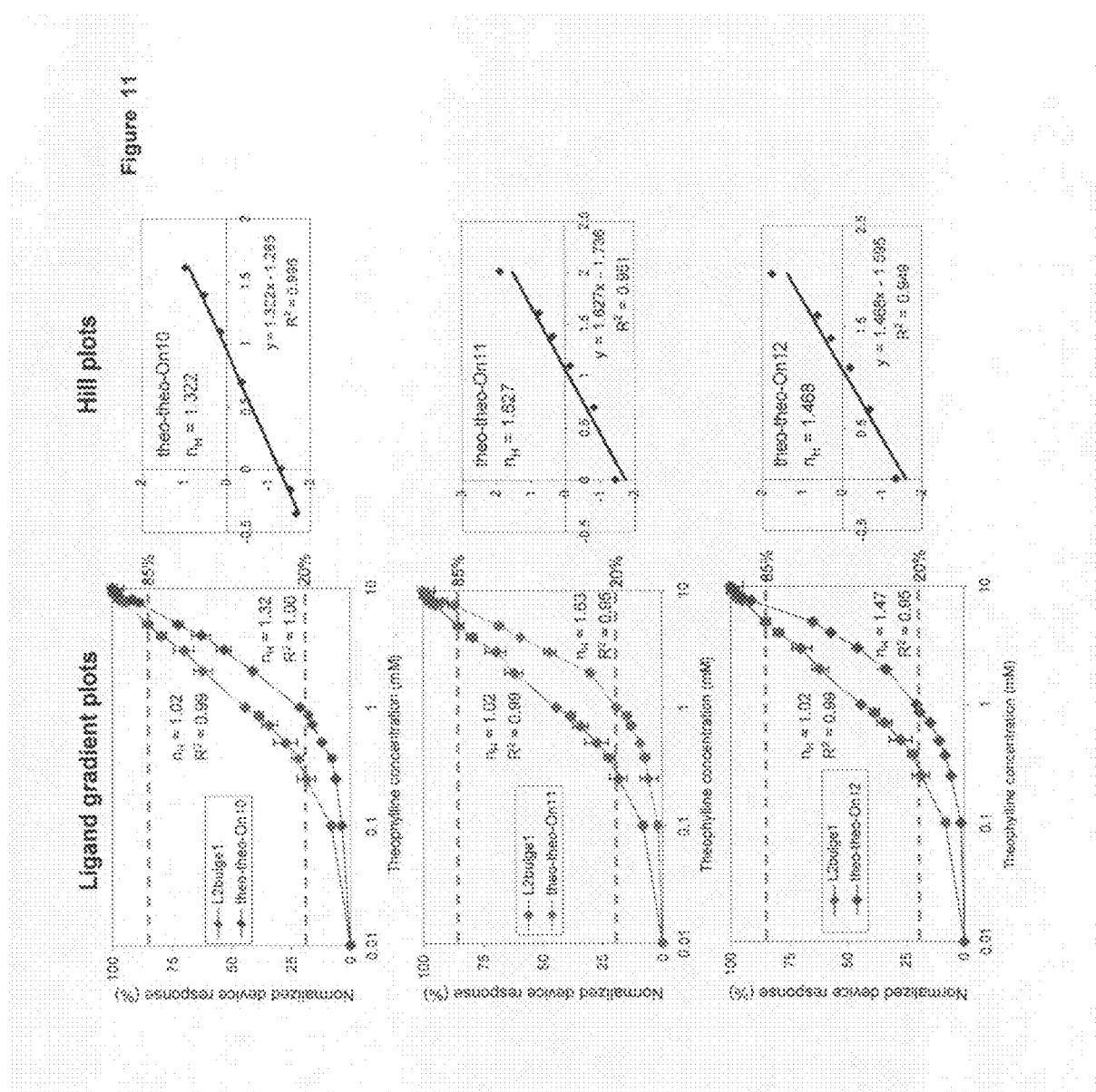
FIG. 11 shows that the device response over varying theophylline concentrations of RNA devices composed of internal Buffer and Inverter gates (theo-theo-On10-12) and their single-internal gate device counterpart (L2bulge1) demonstrates programmed cooperativity. The device response is normalized to the response at 10 mM theophylline. Corresponding Hill plots are constructed for 20-85% of each normalized device response by plotting log expressed/(1−fraction expressed)] against log [input concentration], where the slope represents the Hill coefficient ($n_H$).

For example, in Table 2, nine SI 3 type devices (theo-theo-On1 to -On9) were constructed by coupling theophylline-responsive internal Buffer (IG1) and Inverter (IG2) gates to stem II of a ribozyme. Device response is reported as the difference between expression activities in the absence and presence of 10 mM theophylline. While all nine devices performed Buffer operations like their single-internal gate device counterpart (L2bulge1), none of them exhibited programmed cooperativity where $\Delta\Delta G_{IG1}=0.3$ kcal/mol was used. In contrast, when $\Delta\Delta G_{IG1}$ was increased to 1 kcal/mol, the devices exhibited substantial degrees of cooperativity (see FIG. 4E and FIG. 11, for theo-theo-On10 to -On13). The data indicates that $\Delta\Delta G_{IG1}$ was important to the observed cooperative response, in that increasing the free energy difference between the two states corresponding to the proximal aptamer can increase the degree of cooperativity (as measured by Hill coefficient $n_H$). Conversely, decreasing the free energy difference between the two states corresponding to the proximal aptamer can decrease or eliminate the degree of cooperativity (as measured by Hill coefficient $n_H$).

The same design principle also applies to SI 3 type devices with more than 2 input gates, and SI 3 type devices that bind different inputs/ligands. Free energy changes between RNA device states can be predicted using any art-recognized methods, such as a standard RNA folding program like RNAStructure 4.6 (see rna.urmc.rochester dot edu/rnastructure.html), Mfold, Vienna package, or Sfold, etc.

4. Sensor/Aptamer-Regulated Nucleic Acids

The signal processing/integration devices of the invention are based on the same modular components used to construct single-input sensor/aptamer-regulated nucleic acids. This section provides a brief general description of the common elements (e.g., sensors/aptamers and the various actuator domains) used to construct the subject signal processing/integration devices.

The sensor domain (aptamer) regulated nucleic acids are powerful, allosteric regulators of gene expression. A general design of such nucleic acids is based on conformational dynamics of nucleic acid folding to create a modular molecule comprising a modular actuator domain, a modular sensor (aptamer) domain, and an information transmission domain (ITD) that functionally couples the actuator domain and the sensor (aptamer) domain such that the latter two domains can remain truly modular. In contrast to the strand-slippage mechanism (see definition below) based information transmission domain, an ITD based on the strand-displacement mechanism is amenable to rational design. Such a strand-displacement mechanism uses competitive binding of two nucleic acid sequences (e.g., the competing strand and the switching strand) to a general transmission region of the switch (e.g., the base stem of the aptamer) to result in disruption or restoration of the actuator domain in response to restoration of the sensor domain.

In certain embodiments, the switching strand of the ITD is linked to the competing strand to form a continuous sequence. This design feature eliminates any free-floating ends of the switching/competing strands, thereby improving the kinetics of strand-displacement.

In general, the sensor domain-regulated nucleic acids are preferably designed such that they can adopt at least two conformations. In one conformation, the sensor domain is capable of binding to a ligand, and the actuator domain may adopt one activity state (e.g., more active state or less active state). In the other conformation, the sensor domain is incapable of binding to the ligand, and the actuator domain may adopt another activity state. The conformation change of the sensor domain may be transmitted through the information transmission domain to the coupled actuator domain, so that the actuator domain adopts one of the two activity states depending on whether the sensor domain can or cannot bind the ligand.

While not wishing to be bound by any particular theory, the two conformations are distributed partly based on the free energy differences between the two conformations. Ligand binding to one of the two conformations provides additional stability to the complex, thus shifting the distribution towards the conformation capable of ligand-binding, and thus favoring the activity state of the actuator domain associated with the ligand-binding sensor domain. Thus in macro level, it appears that ligand-binding has caused a conformation change from one conformation to the other, and "conformation change" may be used herein to describe the ligand binding-induced distribution shift.

The sensor-regulated nucleic acid platform is flexible, enabling both positive and negative regulations. For example, the ligand-bound sensor domain may be associated with the more active form of the actuator domain, or with the less active form of the actuator domain.

The switching dynamics of aptamer-regulated nucleic acids are amenable to tuning by forward engineering design strategies based on thermodynamic properties of nucleic acids. Altering the free energy of the actuator domain and/or the sensor domain alters the conformational dynamics of these molecules in a predictable fashion. Specifically, decreasing the stability of the actuator domain associated with one activity state (by, for example, reducing the length of perfectly matched base pairs in a stem structure within the actuator domain, or lower the quality of base-pairing) may favor the equilibrium/distribution shift to the other activity state of the actuator domain (and its associated sensor domain conformation), thus increasing or decreasing the ligand concentration necessary to induce the equilibrium/distribution shift between the two conformations. Similarly, changing the size of the sensor domain, and/or changing the affinity of the sensor (aptamer) domain for the ligand may also be used to fine tune the equilibrium/distribution between the two conformations. Furthermore, similar changes can be made to the ITD, where modifications can be used to fine tune the energetic (e.g., free energy) differences between the different conformations.

These fine tuning strategies may be used in combination to provide flexible yet predictable changes in activity of the sensor domain-regulated nucleic acids in response to different ligand concentrations or environmental condition change.

In addition, the aptamer-regulated nucleic acid platform (and thus the various SI schemes) is fully modular, enabling ligand response and actuator function (e.g., transcript targeting) to be engineered by swapping domains within the subject regulated nucleic acid. This provides a platform for the construction of tailor-made sensor domain regulated nucleic acids for a variety of different ligands. Ligand binding of the aptamer domain in aptamer-regulated nucleic acids is designed separately from the targeting capability of the actuator domain by swapping only the aptamer domain. Likewise, the targeting capability of the actuator domain can be designed separately from the ligand binding of the aptamer domain by swapping the actuator domain so that a different gene or molecule is targeted without affecting the aptamer domain. This feature is made possible by the unique property of the subject information transmission domain that employs the strand-displacement mechanism. Thus, the sensor domain-regulated nucleic acids present a powerful, flexible method of tailoring spatial and temporal gene expression in both natural and engineered contexts.

The sensor domain-regulated nucleic acids and the various signal processing/integration devices are novel, allosteric regulators of gene expression that can potentially function across a diverse range of organisms, from prokaryotes to humans, making them extremely useful in many different applications. For example, the subject devices present a powerful tool for gene therapy applications, where one would like to target specific transcripts in response to specific cellular environments that are indicative of a diseased state (Watkins et al., Curr Opin Mol Ther 4, 224-8 (2002)). As emerging technologies enable the metabolic profiling of disease states (Koch, J Biol Chem 219: 181-188, 1956), the subject devices can be designed to respond to various metabolic markers, or a specific concentration range of a metabolic marker, partly owning to the ability of the subject signal processing/integration devices to sense and respond to multiple input signals. For instance, the subject devices can be constructed to inhibit genes necessary for cell growth and division in response to oncogenic proteins or isoforms. One can also anticipate an exogenously delivered signal processing/integration device with an actuator domain that is an antisense construct or RNase III substrate acting as a therapeutic molecule, similar to exogenously delivered antisense oligonucleotides or RNAi therapeutic agents, thereby extending the functionality of current antisense/RNAi therapies by introducing ligand-specific or cell type-specific action to an already highly targeted therapy.

The subject signal processing/integration devices can further be used to engineer novel regulatory pathways and control loops for applications in metabolic engineering (Khosla et al., Nat Rev Drug Discov 2: 1019-1025, 2003) and synthetic circuit design (Kobayashi et al., Proc Natl Acad Sci USA 101: 8414-8419, 2004) by enabling the cell to sense and respond to intracellular metabolite levels and environmental signals. Because the subject devices are tunable over a range of ligand concentrations, the devices can be designed to inhibit or activate genes only when certain metabolites fail within certain concentrations. Balancing heterologous gene expression in biosynthetic pathways (Berens et al., Bioorg Med Chem 9: 2549-2556, 2001) to maximize product yield can be achieved with the subject signal processing/integration devices that regulate expression of biosynthetic genes in response to various pathway intermediate levels. Synthetic gene circuits have recently been used to understand and model cellular networks (Nagai et al., Nat Biotechnol 20: 87-90, 2002) and to achieve cellular control as a step towards "programmable" cell behavior (Watkins et al., Curr Opin Mol Ther 4: 224-228, 2002). Gene circuits can be built using the subject signal processing/integration devices as regulators for precise control schemes. The subject signal processing/integration devices are also useful tools in building and characterizing circuits that accurately model natural regulatory pathways and yield further insight into these prevalent regulation schemes.

Finally, the subject signal processing/integration devices present new tools for cellular imaging, measuring, and detection strategies enabling programmable concentration-specific detection of intracellular molecules. Such nucleic acids offer a unique platform to create tailor-made cellular sensors and "smart" regulators that potentially can target any gene in response to any target ligand, creating new avenues for cellular control and engineering.

The signal processing/integration devices of the invention may comprise modular actuator domain(s), modular sensor domain(s), and information transmission domain(s). Such devices may comprise DNA or RNA, or a combination thereof. The devices may also be single-stranded or double-stranded. The single-stranded polynucleotide may comprise one or more double-stranded regions (or stems) due to intramolecular interaction (e.g., RNA secondary structure). If one or more phosphodiester linkages between the nucleotides are broken, the folded polynucleotide may in fact be double-stranded while maintaining substantially the same secondary structure.

The subject devices may comprise multiple modular components, e.g., one or more aptamer domains and/or one or more actuator domains. The sensor-regulated polynucleotides may further comprise a functional group or a functional agent, e.g., an intercalator or an alkylating agent. The sensor-regulated polynucleotides may comprise synthetic or non-natural nucleotides and analogs (e.g., 6-mercaptopurine, 5-fluorouracil, 5-iodo-2'-deoxyuridine and 6-thioguanine) or may include modified nucleic acids. Exemplary modifications include cytosine exocyclic amines, substitution of 5-bromo-uracil, backbone modifications, methylations, and unusual base-pairing combinations. Additional analogs include at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The subject devices may also include labels, such as fluorescent, radioactive, chemical, or enzymatic labels.

The response of the sensor (aptamer) domain to the ligand may also depend on the ligand identity and/or the amount or concentration of ligand exposed to the sensor (aptamer) domain. For example, an aptamer may bind small molecules, such as drugs, metabolites, intermediates, cofactors, transition state analogs, ions, metals, nucleic acids, and toxins. Alternatively, an aptamer may bind natural and synthetic polymers, including proteins, peptides, nucleic acids, polysaccharides, glycoproteins, hormones, receptors and cell surfaces such as cell walls and cell membranes.

In certain other embodiments, the sensor domain of the subject ligand-controlled, sensor-regulated polynucleotide is responsive to environmental changes. Environmental changes include, but are not limited to changes in pH, temperature, osmolarity, or salt concentration.

Aptamers

An "aptamer" may be a nucleic acid molecule, such as RNA or DNA that is capable of binding to a specific molecule with high affinity and specificity (Ellington et al., *Nature* 346, 818-22 (1990); and Tuerk et al., *Science* 249, 505-10 (1990)). Exemplary ligands that bind to an aptamer include, without limitation, small molecules, such as drugs, metabolites, intermediates, cofactors, transition state analogs, ions, metals, nucleic acids, and toxins. Aptamers may also bind natural and synthetic polymers, including proteins, peptides, nucleic acids, polysaccharides, glycoproteins, hormones, receptors and cell surfaces such as cell walls and cell membranes. The binding of a ligand to an aptamer, which is typically RNA, causes or favors a conformational change in the actuator domain and alters its ability to interact with its target molecule. Therefore, ligand binding affects the actuator domain's ability to mediate gene inactivation, transcription, translation, or otherwise interfere with the normal activity of the target gene or mRNA, for example.

An aptamer will most typically have been obtained by in vitro selection for binding of a target molecule. However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants ($K_D$) of the aptamer for its ligand as compared to the dissociation constant of the aptamer for other materials in the environment or unrelated molecules in general. A ligand is one which binds to the aptamer with greater affinity than to unrelated material. Typically, the $K_D$ for the aptamer with respect to its ligand will be at least about 10-fold less than the $K_D$ for the aptamer with unrelated material or accompanying material in the environment. Even more preferably, the $K_D$ will be at least about 50-fold less, more preferably at least about 100-fold less, and most preferably at least about 200-fold less. An aptamer will typically be between about 10 and about 300 nucleotides in length. More commonly, an aptamer will be between about 30 and about 100 nucleotides in length.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

Aptamers are readily made that bind to a wide variety of molecules. Each of these molecules can be used as a modulator of gene expression using the methods of the invention. For example, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have been successfully used as target ligands for in vitro aptamer selections (Werstuck and Green, *Science* 282:296-298 (1998)). Other small organic molecules like dopamine, theophylline, sulforhodamine B, and cellobiose have also been used as ligands in the isolation of aptamers. Aptamers have also been isolated for antibiotics such as kanamycin A, lividomycin, tobramycin, neomycin B, viomycin, chloramphenicol and streptomycin. For a review of aptamers that recognize small molecules, see Famulok, *Science* 9:324-9 (1999).

In certain embodiments, the ligand of the aptamer of an aptamer-regulated nucleic acid of the invention is a cell-permeable, small organic molecule. Small organic molecules which do not have a general inhibitory effect on translation are preferred as ligands. The small molecule preferably also exhibits in vivo persistence sufficient for achieving the desired level of inhibition of translation. The molecules also can be screened to identify those that are bioavailable after, for example, oral administration. In certain embodiments of the invention, the ligand is nontoxic. The ligand may optionally be a drug, including, for example, a steroid. However, in some of the methods of controlling gene expression, it is preferable that the ligand be pharmacologically inert. In some embodiments, the ligand is a polypeptide whose presence in the cell is indicative of a disease or pathological condition. In other embodiments, the ligand for an aptamer is an antibiotic, such as chloramphenicol. In an alternative embodiment, the ligand of the aptamer is an organic dye such as Hoeschst dye 33258. In still another embodiment, the ligand may be a metal ion. In a specific embodiment, the aptamer domain of an aptamer-regulated nucleic acid responds to binding to caffeine.

The device of the invention can be entirely of RNA. In other embodiments of the invention, however, the device can instead be entirely of DNA, or partially of DNA, or partially of other nucleotide analogs. To specifically inhibit translation in vivo, RNAs are preferred. Such aptamer-regulated RNAs are preferably introduced into a cell by introducing a DNA that encodes the subject RNA device. Alternatively, an RNA signal processing/integration device can be introduced directly into a cell.

Aptamers are typically developed to bind particular ligands by employing known in vivo or in vitro (most typically, in vitro) selection techniques known as SELEX (Ellington et al., Nature 346, 818-22 (1990); and Tuerk et al., Science 249, 505-10 (1990)). Methods of making aptamers are also described in, for example, U.S. Pat. No. 5,582,981, PCT Publication No. WO 00/20040, U.S. Pat. No. 5,270,163, Lorsch and Szostak, Biochemistry, 33:973 (1994), Mannironi et al., Biochemistry 36:9726 (1997), Blind, Proc. Nat'l. Acad. Sci. USA 96:3606-3610 (1999), Huizenga and Szostak, Biochemistry, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptamer is preferably selected for ligand binding in the presence of salt concentrations and temperatures which mimic normal physiological conditions.

An improved aptamer selection scheme that is particularly suitable for selecting aptamers within the switch platform is described in the co-owned and co-pending U.S. application Ser. No. 12/218,628, filed on Jul. 16, 2008, the entire content of which is incorporated herein by reference.

One can generally choose a suitable ligand without reference to whether an aptamer is yet available. In most cases, an aptamer can be obtained which binds the ligand of choice by someone of ordinary skill in the art. The unique nature of the in vitro selection process allows for the isolation of a suitable aptamer that binds a desired ligand despite a complete dearth of prior knowledge as to what type of structure might bind the desired ligand.

For an aptamer to be suitable for use in the present invention, the binding affinity of the aptamer for the ligand must be sufficiently strong, and the structure formed by the aptamer when bound to its ligand must be significant enough, so as to switch an aptamer-regulated nucleic acid of the invention between a more active state and a less active (or inactive) state, or tune the function level of an aptamer-regulated nucleic acid.

The association constant for the aptamer and associated ligand is preferably such that the ligand functions to bind to the aptamer and have the desired effect at the concentration of ligand obtained upon administration of the ligand. For in vivo use, for example, the association constant should be such that binding occurs well below the concentration of ligand that can be achieved in the serum or other tissue, preferably well below the concentration of ligand that can be achieved intracellularly since cellular membranes may not be sufficiently permeable to allow the intracellular ligand concentration to approach the level in the serum or extracellular environment. Preferably, the required ligand concentration for in vivo use is also below that which could have undesired effects on the organism.

Actuator/Effector Domain

An actuator/effector nucleic acid domain may comprise an antisense nucleic acid or a DNA. An effector nucleic acid domain may also comprise a sequence that can be used as an RNAi sequence or precursor that gives rise to siRNA or miRNA. Yet other actuator domains can be an shRNA or precursor thereof, an RNase III substrate, an alternative splicing element, or an RNAi targeting sequence. In certain embodiments, the actuator of the invention does not include a ribozyme or other catalytic nucleic acids.

In preferred embodiments, ligand binding at the sensor (aptamer) domain mediates a change in the conformational dynamics of these molecules that allows or prevents the actuator domain to interact with a target nucleic acid, for example, an mRNA.

In one embodiment, the actuator domain interacts with a target gene by nucleic acid hybridization. For instance, the actuator domain may comprise a hybridization sequence that hybridizes to a target sequence of a gene. The binding of the ligand to the aptamer domain(s) favors a conformational change in the subject device that alters the ability (such as availability and/or $T_m$) of the hybridization sequence of the actuator domain to hybridize to a target sequence. Furthermore, an actuator domain may modulate the expression or activity of its target by any method known in the art.

In one embodiment, the actuator domain may comprise an antisense sequence and acts through an antisense mechanism in modulating expression of a target gene. For instance, an actuator domain may comprise an antisense sequence for inhibiting expression of a target gene. The binding of the ligand to the aptamer domain(s) causes a conformational change that alters the ability of the antisense sequence of the actuator domain to inhibit expression of the target sequence. As used herein, such aptamer-regulated nucleic acids are also referred to as "antiswitches." As used herein, "antisense" technology refers to administration or in situ generation of molecules or their derivatives which specifically hybridize (e.g., bind) under cellular conditions, with the target nucleic acid of interest (mRNA and/or genomic DNA) encoding one or more of the target proteins so as to inhibit expression of that protein, e.g., by inhibiting transcription and/or translation, such as by steric hindrance, altering splicing, or inducing cleavage or other enzymatic inactivation of the transcript. The binding may be by conventional base pair complementarity, or, for example, in the case of binding to DNA duplexes, through specific interactions in the major groove of the double helix. In general, "antisense" technology refers to the range of techniques generally employed in the art, and includes any therapy that relies on specific binding to nucleic acid sequences.

An antiswitch can be delivered as a component of an expression plasmid to produce an effector domain complementary to at least a unique portion of the target nucleic acid. Alternatively, the antiswitch can be generated outside of the target cell and introduced into a target cell, such that the antiswitch will inhibit expression by hybridizing with the target nucleic acid. Aptamer-regulated nucleic acids may be modified so that they are resistant to endogenous nucleases, e.g. exonucleases and/or endonucleases, and are therefore stable in vivo. Exemplary nucleic acid molecules for use in aptamer-regulated nucleic acids are phosphoramidate, phosphothioate and methylphosphonate analogs of DNA.

Several considerations may be taken into account when constructing antisense actuator domains for use in the compositions and methods of the invention: (1) antisense actuator domains preferably have a GC content of 50% or more; (2) generally, avoid sequences with stretches of 3 or more Gs; and (3) antisense actuator domains preferably should not be longer than 25-26 mers when in their "on" state and modulating a target gene. When testing an antisense actuator domain, a mismatched control can be constructed. The controls can be generated by reversing or scrambling the sequence order of the corresponding antisense oligonucleotide in order to conserve the same ratio of bases.

Antisense actuator domains may be complementary to the 5' end of an mRNA target, or complementary to the 3' untranslated sequences of mRNAs.

Antiswitches can be DNA or RNA or chimeric mixtures or derivatives or modified versions thereof, single-stranded or double-stranded. Antiswitches can be modified at the base moiety, sugar moiety, or phosphate backbone, for example, to improve stability of the molecule, hybridization, etc. Antiswitches may include other appended groups such as peptides (e.g., for targeting host cell receptors), or agents facilitating transport across the cell membrane (see, e.g., Letsinger et al., 1989, *Proc Natl Acad. Sci. USA* 86:6553-6556; Lemaitre et al., 1987, *Proc Natl Acad. Sci. USA* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, *BioTechniques* 6:958-976) or intercalating agents. (See, e.g., Zon, *Pharm. Res.* 5:539-549 (1988)). To this end, an antiswitch may be conjugated to another molecule, e.g., a peptide, hybridization triggered cross-linking agent, transport agent, hybridization-triggered cleavage agent, etc.

An antiswitch may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil; beta-D-mannosylqueosine, 5-methoxycarboxymethyluracil, 5-methoxyuracil, 5-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

An antiswitch may also comprise at least one modified sugar moiety selected from the group including but not limited to arabinose, 2-fluoroarabinose, xylulose, and hexose.

An antiswitch can also contain a neutral peptide-like backbone. Such molecules are termed peptide nucleic acid (PNA)-oligomers and are described, e.g., in Perry-O'Keefe et al. (1996) *Proc. Natl. Acad. Sci. USA* 93:14670 and in Eglom et al. (1993) *Nature* 365:566. One advantage of PNA oligomers is their capability to bind to complementary DNA essentially independently from the ionic strength of the medium due to the neutral backbone of the DNA. In yet another embodiment, an antiswitch comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, an antiswitch is an anomeric oligonucleotide. An anomeric oligonucleotide forms specific double-stranded hybrids with complementary RNA in which the strands run parallel to each other (Gautier et al., 1987, *Nucl. Acids Res.* 15:6625-6641). The oligonucleotide is a 2'-O-methylribonucleotide (Inoue et al., 1987, *Nucl. Acids Res.* 15:6131-6148), or a chimeric RNA-DNA analogue (Inoue et al., 1987, *FEBS Lett.* 215:327-330).

Upon delivery of an antiswitch-containing signal processing/integration device into a cell, it may be difficult to achieve intracellular concentrations of the device sufficient to affect the activity of a target gene or mRNA or interest in certain instances. Therefore, another approach utilizes a recombinant DNA construct in which the antiswitch or other aptamer-regulated nucleic acid in the device are placed under the control of a strong pol III or pol II promoter. This embodiment is useful for RNA devices that act in trans, but could also be used in the cis-acting embodiments if the entire gene construct containing both the target gene and the RNA devices in the 3' UTR of the gene were under the control of a strong promoter.

In another embodiment, the actuator domain may comprise an RNAi sequence and acts through an RNAi or miRNA mechanism in modulating expression of a target gene. For instance, binding of the ligand to the aptamer domain(s) causes a conformational change that alters the ability of the miRNA or siRNA sequence of the actuator domain to inhibit expression of the target sequence. In one embodiment, an effector domain comprises a miRNA or siRNA sequence that is between about 19 nucleotides and about 35 nucleotides in length, or preferably between about 25 nucleotides and about 35 nucleotides. In certain embodiments, the actuator domain is a hairpin loop that may be processed by RNase III enzymes (e.g., Drosha and Dicer). As used herein, the term "RNAi" means an RNA-mediated mechanism for attenuating gene expression and includes small RNA-mediated silencing mechanisms. RNA-mediated silencing mechanisms include inhibition of mRNA translation and directed cleavage of targeted mRNAs. Recent evidence has suggested that certain RNAi constructs may also act through chromosomal silencing, i.e., at the genomic level, rather than, or in addition to, the mRNA level. Thus, the sequence targeted by the actuator domain can also be selected from untranscribed sequences that regulate transcription of a target gene of the genomic level.

An RNAi construct contains a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "siRNAs." These nucleic acids are between about 19-35 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex or translation is inhibited. In a particular embodiment, the 21-23 nucleotides siRNA molecules comprise a 3' hydroxyl group.

In other embodiments, the subject RNAi constructs are "miRNAs." microRNAs (miRNAs) are small non-coding RNAs that direct post transcriptional regulation of gene expression through interaction with homologous mRNAs. miRNAs control the expression of genes by binding to complementary sites in target mRNAs from protein coding genes. miRNAs are similar to siRNAs. miRNAs are processed by nucleolytic cleavage from larger double-stranded precursor molecules. These precursor molecules are often hairpin structures of about 70 nucleotides in length, with 25 or more nucleotides that are base-paired in the hairpin. The RNase III-like enzymes Drosha and Dicer (which may also be used in siRNA processing) cleave the miRNA precursor to produce an miRNA. The processed miRNA is single-stranded and incorporates into a protein complex, termed RISC or miRNP. This RNA-protein complex targets a complementary mRNA. miRNAs inhibit translation or direct cleavage of target mRNAs. (Brennecke et al., Genome Biology 4:228 (2003); Kim et al., Mol. Cells. 19:1-15 (2005)).

In certain preferred embodiments, at least one strand of the siRNA sequence of an effector domain has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA sequence, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In another embodiment, the actuator domain may comprise a hairpin RNA which is processed to an siRNA in the treated cells.

The methods described herein may employ an expression vector having a coding sequence that is transcribed to produce one or more transcriptional products that produce a subject signal processing/integration device in the treated cells. Expression vectors appropriate for producing the subject signal processing/integration device are well-known in the art. For example, the expression vector may be selected from an episomal expression vector, an integrative expression vector, and a viral expression vector, etc.

In certain embodiments, the expression construct can be designed to include one or more subject devices in an RNA transcript, such as in the 3' UTR, so as to regulate transcription, stability and/or translation of that RNA transcript in a manner dependent on the ligand. To further illustrate, the expression construct can include a coding sequence for a gene product (e.g., a polypeptide or non-coding RNA) such that the RNA transcript includes both the coding sequence as well as one or more of the signal processing/integration devices of the invention. In this way, expression of the polypeptide/non-coding RNA can be rendered dependent on the ligand(s) to which the aptamer binds.

The invention further provides a class of in vivo nucleic acid sensors, for example, aptamer-regulated signal processing/integration devices that directly sense the presence or amount of intracellular molecules through changes in nucleic acid conformation upon ligand binding to the aptamer domain(s) of an aptamer-regulated signal processing/integration device. For example, ligands that interact with the aptamer domain(s) of a subject aptamer-regulated signal processing/integration devices switch "on" the actuator domain(s) of the aptamer-regulated signal processing/integration devices. The activated actuator domain(s) then targets a "reporter" molecule. The reporter molecule is activated or repressed by its interaction with the actuator domain. The amount or activity of the reporter molecule, therefore, correlates with the amount or concentration of the ligands of interest. Exemplary reporter molecules include, without limitation, fluorescent reporter proteins such as green fluorescent protein (GFP or any of its art-recognized variants) or luciferase, enzymatic reporters such as alkaline phosphatase, or colorimetric reporters such as β-galactosidase. Alternatively, the activated actuator domain(s) may target one or more non-reporter target genes, either in cis or in trans with the subject signal processing/integration devices.

5. Exemplary Formulations

The signal processing/integration devices of the invention may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject aptamer-regulated nucleic acids can be provided in formulations also including penetration enhancers, carrier compounds and/or transfection agents.

Representative United States patents that teach the preparation of such uptake, distribution and/or absorption assisting formulations which can be adapted for delivery of the subject signal processing devices include, but are not limited to, U.S. Pat. Nos. 5,108,921; 5,354,844; 5,416,016; 5,459,127; 5,521, 291; 51,543,158; 5,547,932; 5,583,020; 5,591,721; 4,426, 330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

Signal processing/integration devices of the invention also encompass any pharmaceutically acceptable salts, esters or salts of such esters, or any other compound which, upon administration to an animal including a human, is capable of providing (directly or indirectly) the biologically active metabolite or residue thereof. Accordingly, for example, the disclosure is also drawn to signal processing/integration devices and pharmaceutically acceptable salts, and other bioequivalents.

Pharmaceutically acceptable base addition salts are formed with metals or amines, such as alkali and alkaline earth metals or organic amines. Examples of metals used as cations are sodium potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of the acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids. Preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

Other formulations, delivery methods, and routes of administration are also provided, such as those described in U.S. Pat. App. Publication No. 20040063654.

6. Exemplary Uses

One aspect of the present invention provides methods for modulating the amount and/or activity of one or more ligands in a cell. The method may comprise designing and selecting one or more aptamers responsive to the ligands and designing an aptamer-regulated signal processing/integration device wherein the aptamers are coupled to one or more actuator domains, as described in the detailed description above. The actuator domains may be targeted to a molecule, a signaling and/or metabolic pathway in the cell, provided that the ligand is involved in the pathway, for example, as a metabolite or an intermediate molecule. A signal processing/integration device of the invention can also function as a non-invasive tool to sense and detect the presence of one or more metabolites levels in a cell.

In a similar manner, the present invention also provides methods for modulating a biological or biochemical response of a cell to the presence, amount and/or activity of one or more ligands in a cell. For example, the subject signal processing devices may be used to regulate the level of cellular ligand(s) by regulating enzyme/protein levels in cellular pathway in response to one or more ligands that are involved in the pathway. The ligands may bind to one or more aptamers of the subject device, and trigger the function of the actuators, which in turn may control (in cis or in trans) the expression of the enzymes/proteins.

In another example, the invention provides methods to regulate one or more target genes that regulate a cell trait in response to (bio)chemical signals, such that one has increased control and systems through which to regulate one or more traits in response to different signal combinations. The subject device can be programmed to respond to a specific combination of signals (e.g., the presence of certain ligands, preferably in certain concentration ranges, and/or the absence of certain other ligands, etc.). When all the pre-determined conditions are met, the device will increase or decrease the expression of one or more target genes. More than one such devices may be used concurrently in the same environment, each may control the expression of one specific target gene, or a subset of target genes.

Additional embodiments are also directed to a method of establishing a conditional genetic network. The method may comprise providing a subject signal integration/processing device, wherein the aptamer domains are responsive to one or more ligands and the actuator domain(s) is targeted to a molecule that is unassociated with a signaling, metabolic, enzymatic, or any biochemical pathway that produces the ligands or modulates the activity of the ligands. The method further comprises contacting the cell with the subject device in an effective amount and/or for a sufficient time period, when switched on, that modulates expression of the target molecule, thereby establishing a conditional genetic network. Accordingly, the subject signal processing devices may be used to engineer intracellular gene networks by sensing endogenously generated signals (e.g., ligands) and responding to these signals by affecting the expression of one or more genes in signaling pathways independent of the ligand. A conditional genetic network may be useful, for example, in engineering an intracellular signaling network. In addition, such signal processing devices may be used to allow cells to appropriately respond to the buildup of toxic intermediates and compounds, or to alter the physiology of a cell (e.g., growth, survival, or differentiation).

A signal processing/integration device of the present invention may also be employed to detect non-invasively the presence or absence or the amount of one or more target molecule in a sample.

In a further aspect, a method of the invention is used to inhibit, or at least reduce, unwanted growth of cells in vivo, and particularly the growth of transformed cells. In certain embodiments, the subject method utilizes a signal processing/integration device of the invention to selectively inhibit the expression of genes encoding proliferation-regulating proteins. For instance, the subject method can be used to inhibit expression of a gene product that is essential to mitosis in the target cell, and/or which is essential to preventing apoptosis of the target cell. In the devices of the present invention, the actuator domains can be designed to correspond to the coding sequence or other portions of mRNAs encoding the targeted proliferation-regulating protein. When exposed to the one or more ligands that bind to the aptamer domains, the present devices cause a loss-of-expression phenotype which causes the target cell to become quiescent or to undergo apoptosis.

In certain embodiments, the subject devices are selected to inhibit expression of gene products which stimulate cell growth and mitosis. One class of genes which can be targeted by the method of the present invention are those known as oncogenes. The human oncogenes against which signal processing/integration devices can designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In certain embodiments, the cell is a transformed cell so that the signal processing/integration device is used for the treatment of hyperplastic cell growth, including treatment of a cancer, and inhibiting activation of lymphocytes.

In certain embodiments, the subject signal processing/integration devices are selected by their ability to inhibit expression of a gene(s) essential for proliferation of a transformed cell, and particularly of a tumor cell. Such the aptamer-regulated nucleic acids can be used as part of the treatment or prophylaxis for neoplastic, anaplastic and/or hyperplastic cell growth in vivo, including as part of a treatment of a tumor.

In some embodiments, the subject signal processing/integration devices are selected by their ability to inhibit expression of a gene(s) essential for activation of lymphocytes, e.g., proliferation of B-cells or T-cells, and particularly of antigen-mediated activation of lymphocytes. In certain related embodiments, the methods described herein can be employed for the treatment of autoimmune disorders. In other embodiments, the subject signal processing/integration devices are selected for their ability to inhibit expression of a gene(s) implicated in the onset or progression of diabetes. In still other embodiments, the subject signal processing/integration devices are selected for their ability to inhibit expression of ICAM-1 (intracellular adhesion molecule).

In preferred embodiments, the subject signal processing/integration devices are selected by their ability to inhibit expression of a gene(s) essential for proliferation of smooth muscle cells or other cells of endothelium of blood vessels, such as proliferating cells involved in neointima formation. In such embodiments, the subject method can be used as part of a treatment or prophylaxis for restenosis. Merely to illustrate, signal processing/integration devices applied to the blood vessel endothelial cells after angioplasty can reduce proliferation of these cells after the procedure.

In other embodiments, signal processing/integration devices can serve as tools for interfacing with the environment including both intracellular environment and extracellular environment. For example, a signal processing/integration device can be used to "transport" a target RNA to a cell membrane or other cellular locations, potentially by the aptamer domain that recognizes a signal peptide, and alternatively, a particular target.

EXAMPLES

Having generally described the invention, Applicants refer to the following illustrative examples to help to understand the generally described invention. These specific examples are included merely to illustrate certain aspects and embodiments of the present invention, and they are not intended to limit the invention in any respect. Certain general principles described in the examples, however, may be generally applicable to other aspects or embodiments of the invention.

Example 1

Higher-Order Cellular Information Processing with Synthetic RNA Devices

Applicants provide herein a framework for the construction of RNA devices based on the assembly of three functional components: a sensor component, made of an aptamer; an actuator component (such as one made of a hammerhead ribozyme); and an information transmission domain (or simply "a transmitter component"), made of a sequence that couples the sensor and actuator components. The resulting devices distribute between two primary conformations: one in which the input cannot bind the sensor, and the other in which the input can bind the sensor as a result of competitive hybridization events within the transmitter component. Input binding shifts the distribution to favor the input-bound conformation as a function of increasing input concentration and is translated to a change in the activity of the actuator. In the context of a ribozyme-based system, a "ribozyme-active" state results in self-cleavage of the ribozyme. The RNA device can be coupled to the 3' UTR of the target gene, where ribozyme self-cleavage inactivates the transcript and thereby lowers gene expression independent of cell-specific machinery. Applicants made simple RNA devices that function as single-input Buffer and Inverter gates that convert a molecular input to increased and decreased gene expression output, respectively (18).

The utility of such a composition framework depends, in part, on the extensibility of the framework itself. A framework that provides a general approach for the forward engineering of multi-input devices will allow the combinatorial assembly of many information processing, transduction, and control devices from a smaller number of components. Thus, Applicants used defined points of integration to facilitate the assembly of putatively modular RNA components into sophisticated information processing devices (see FIG. 1A) and specified three exemplary signal integration (SI) schemes (FIG. 1B). SI 1 was used to construct RNA devices that acted as logic gates (AND or NOR gates) and signal and bandpass filters through the assembly of independent single-input gates. SI 2 was used to construct devices that allowed other logic operations (NAND or OR gates) through the assembly of sensor-transmitter components linked to both stems of the ribozyme. SI 3 was used to construct devices that acted as logic gates (AND or OR gates) and exhibited cooperativity through the assembly of two sensor-transmitter components linked to a single ribozyme stem. The various operations were achieved by altering the function or input responsiveness of the single-input gates in SI 1 or sensor-transmitter components in SI 2 and 3. Applicants assembled multiple RNA devices from various components for all operations to demonstrate the generality of the integration schemes.

It should be noted that these exemplary SI schemes are not mutually exclusive, in that any two or more may be combined to achieve higher-order signal processing/integration. Other SI schemes are also possible based on the general description of the invention.

In SI 1, the single-input gates act independently such that computation is performed through integration of individual gate operations in the 3' UTR of the target transcript. Since only one of the ribozymes needs to be in an active state to inactivate the transcript, the device output (gene expression activity) is high only when both ribozymes of the single-input gates are in their inactive states. Applicants engineered signal filters by coupling representative Buffer or Inverter gates (18) responsive to either theophylline or tetracycline (SI 1.1; FIG.

2A). Coupled-gate devices exhibited a device response that was shifted lower compared to that of the single-input gate, indicating the independent action of each single-input gate (FIG. 2B, Examples 2 and 3, Table 1).

Figure 5:
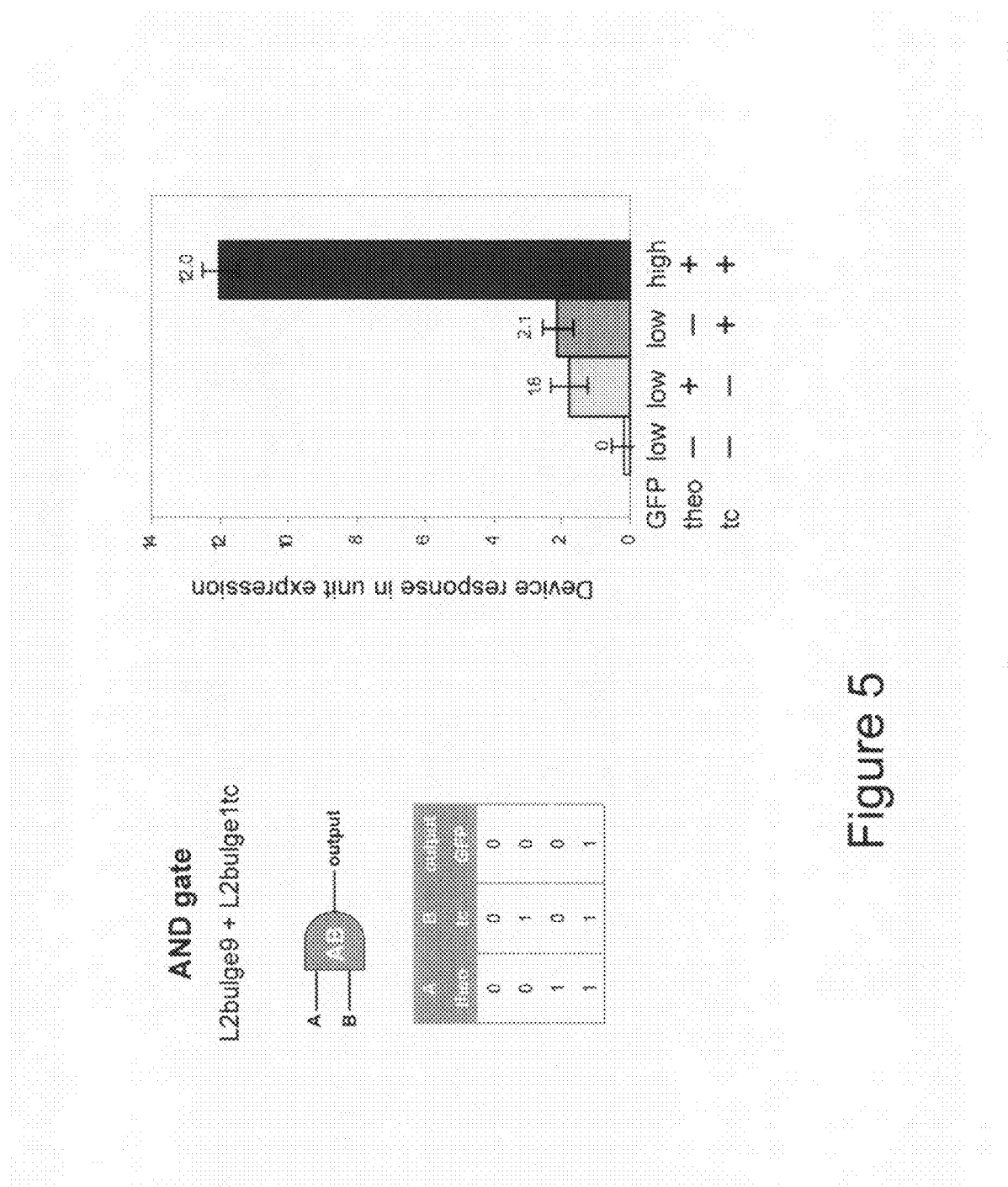
FIG. 5 illustrates the device response and truth table of an AND gate (L2bulge9+L2bulge1tc) based on SI 1.2. The RNA device is constructed by coupling a theophylline-responsive Buffer gate (L2bulge9) and a tetracycline-responsive Buffer gate (L2bulge1tc) in the 3'UTR of a target transcript. Device response under different input conditions (theo or tc(−), 0 mM; theo(+), 5 mM; tc(+), 0.5 mM) is reported as the difference between gene expression activity in the absence of both inputs and that at the indicated input conditions.

Applicants constructed an AND gate that exhibited high output only when both inputs were present by coupling a theophylline-responsive Buffer gate and a tetracycline-responsive Buffer gate (SI 1.2; FIG. 2C). In this composition, only in the presence of both molecular inputs (theophylline and tetracycline) did both Buffer gates favor the ribozyme-inactive state, resulting in high device output (FIG. 2D and FIG. 5).

Figure 6:
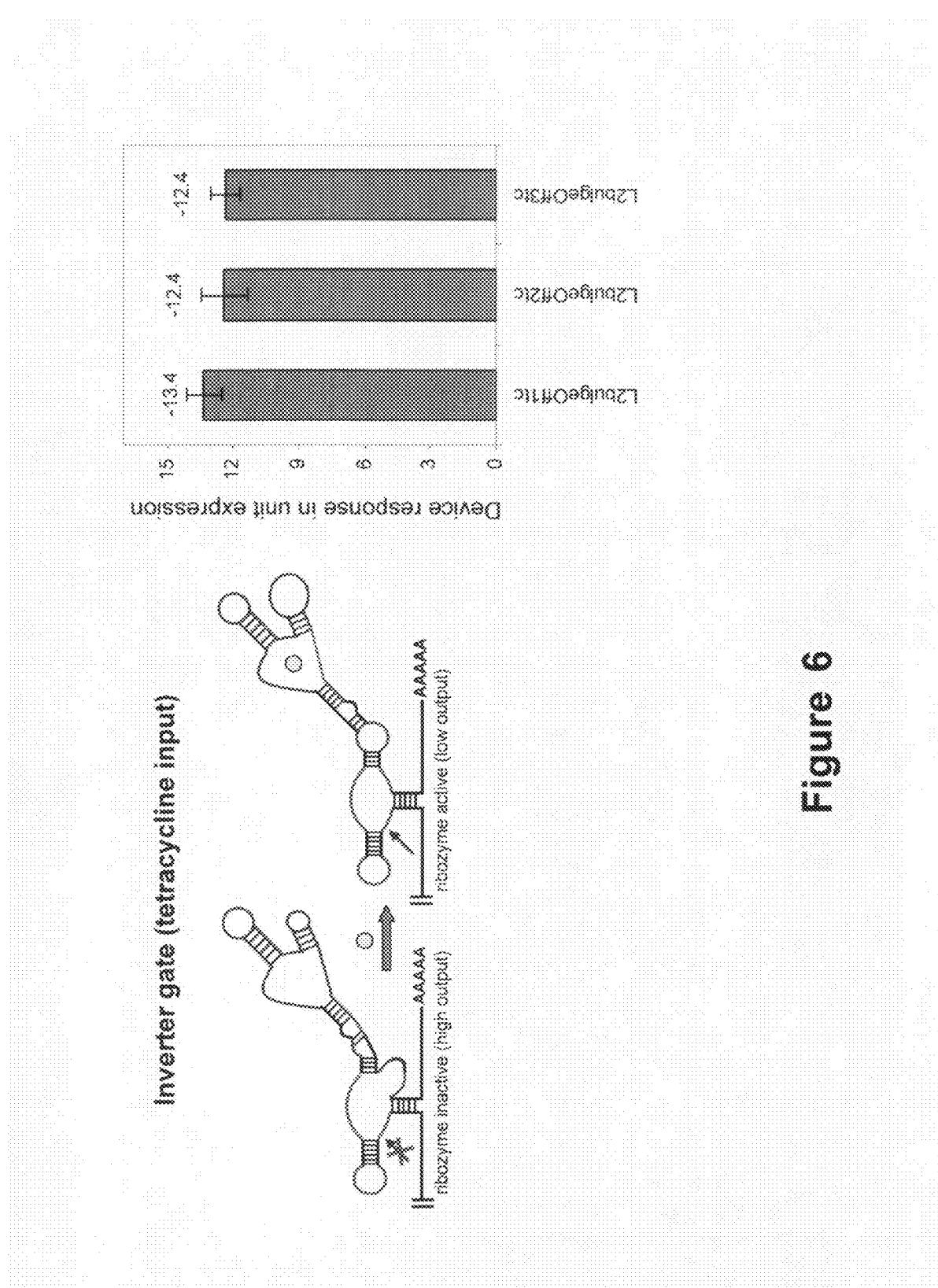
FIG. 6 is a schematic representation and device response of tetracycline-responsive Inverter gates. Device response is reported as the difference between expression activities in the absence and presence of 0.5 mM tetracycline. The negative sign indicates the down-regulation of target gene expression by the Inverter gates.
Figure 7:
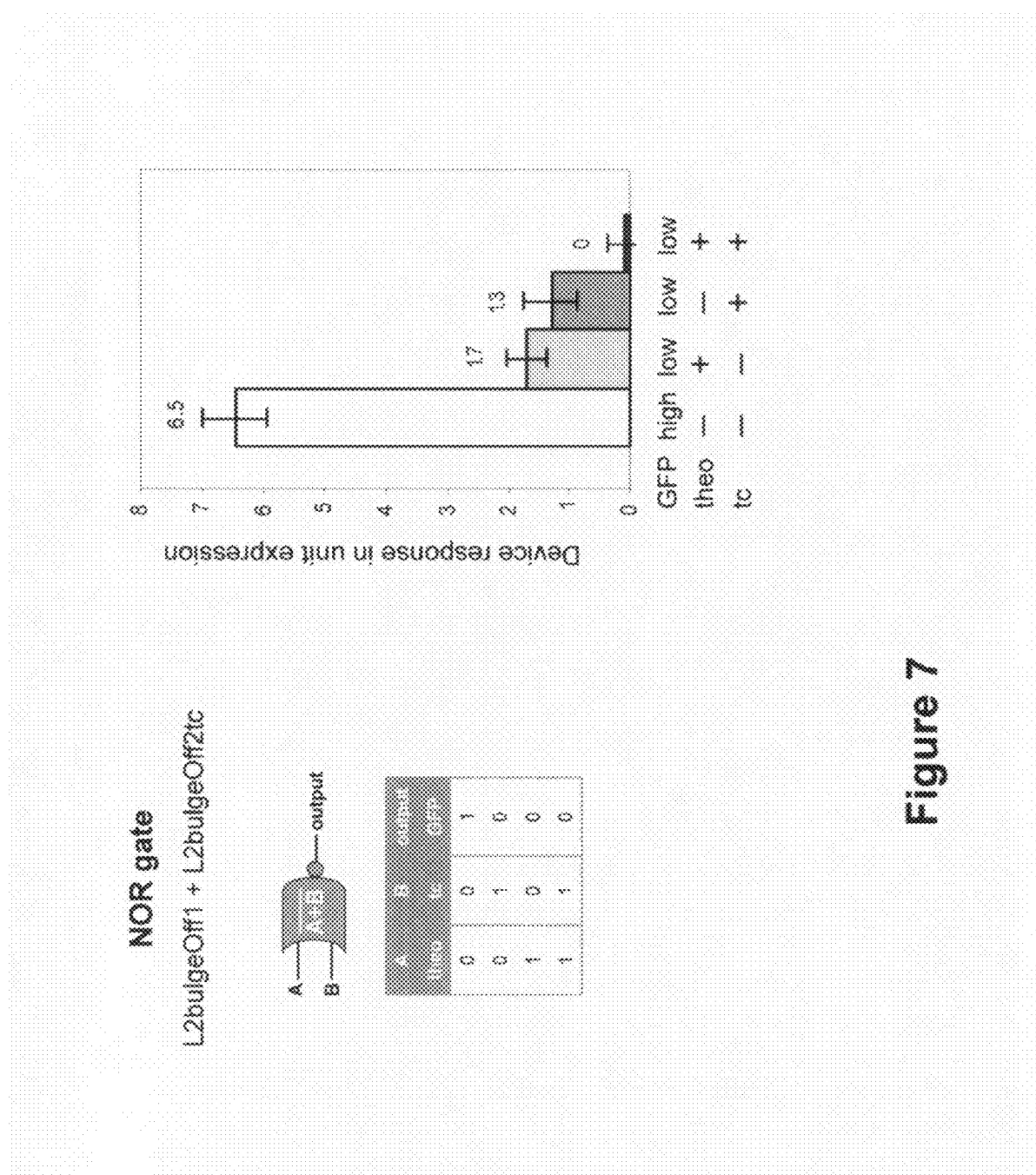
FIG. 7 illustrates the device response and truth table of a NOR gate (L2bulgeOff1+L2bulgeOff2tc) based on SI 1.3. The RNA device is constructed by coupling a theophylline-responsive Inverter gate (L2bulgeOff1) and a tetracycline-responsive Inverter gate (L2bulgeOff2tc) in the 3' UTR of a target transcript. Device response under different input conditions (theo or tc(−), 0 mM; theo(+), 10 mM; tc(+), 0.5 mM) is reported as the difference between expression activity in the presence of both inputs and that at the indicated input conditions.

Applicants constructed a NOR gate that exhibited high output only when both inputs were absent by coupling a theophylline-responsive Inverter gate and a tetracycline-responsive Inverter gate (SI 1.3; FIG. 2E and FIG. 6). In this composition, only in the absence of both inputs did both Inverter gates favor the ribozyme-inactive state, resulting in high device output (FIG. 2F and FIG. 7). Applicants also engineered a bandpass filter that exhibited high output only over intermediate input concentrations by coupling theophylline-responsive Buffer and Inverter gates (FIG. 8). The various devices demonstrated that diverse information processing operations can be assembled through SI 1, where layering strategies can extend the attainable operations (Example 4).

Figure 3:
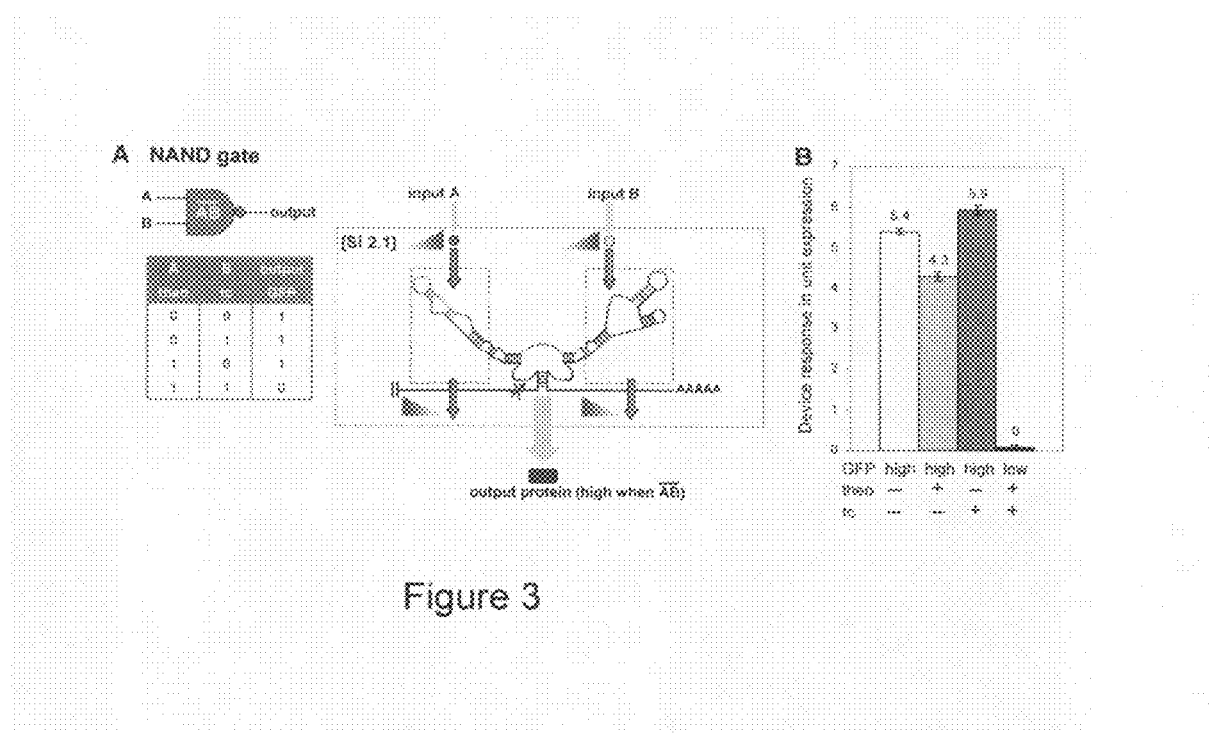
FIG. 3 shows RNA devices based on signal processing/integration at the ribozyme core (SI 2). Internal gates are indicated in dashed boxes, and triangles indicate relationships between associated internal gate inputs and outputs. (A) An RNA device that performs a NAND operation by coupling two internal Inverter gates responsive to different inputs to different ribozyme stems and the associated truth table. (B) The device response of a NAND gate (L1cm10-L2bulgeOff3tc). Device response under different input conditions (theo or tc (−), 0 mM; theo (+), 10 mM; tc (+), 1 mM) is reported as in FIG. 2F.
Figure 9:
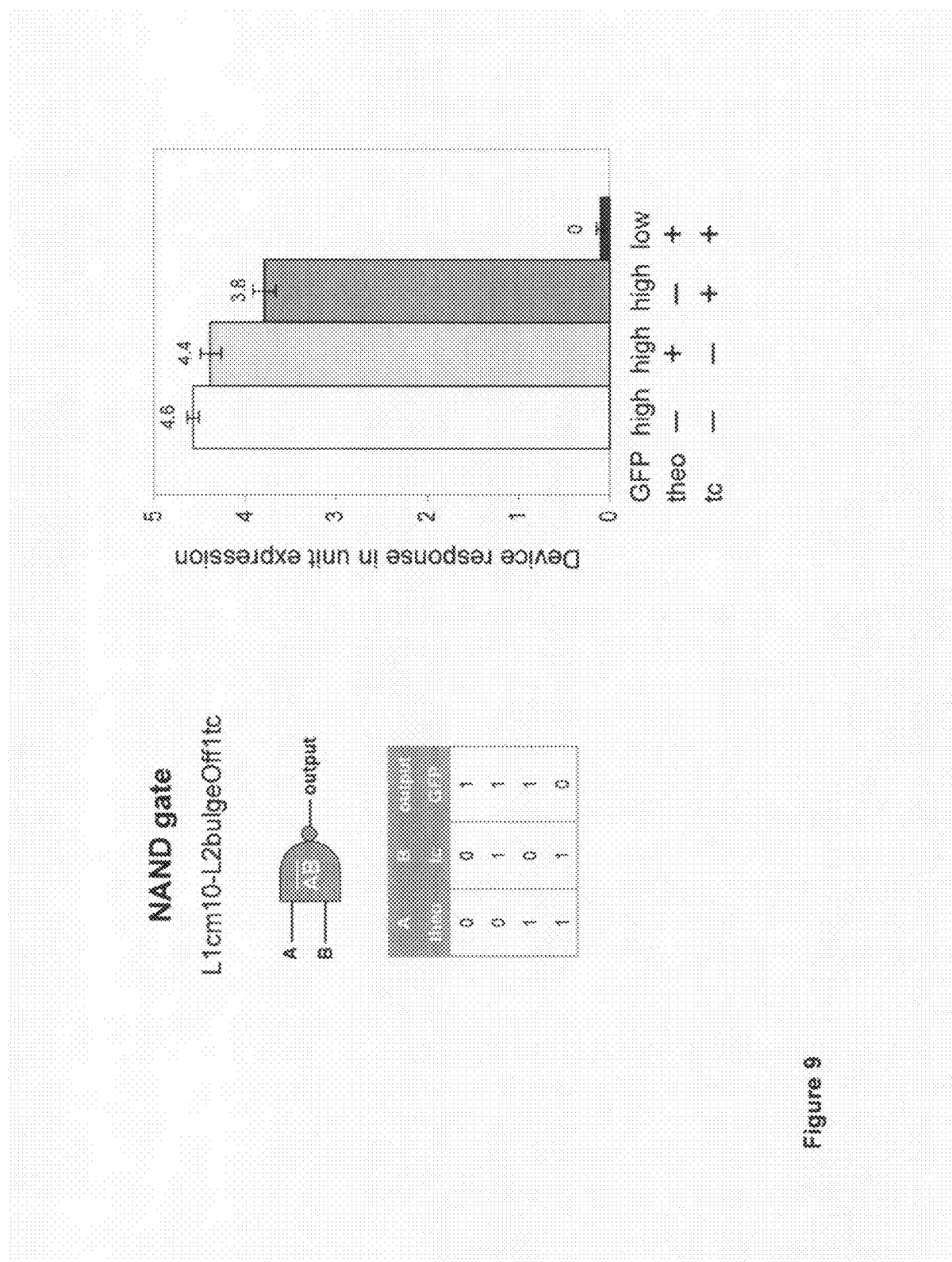
FIG. 9 shows the device response and truth table of a NAND gate (L1cm10–L2bulgeOff1tc) based on SI 2.1. The RNA device is constructed by coupling a theophylline-responsive internal Inverter gate (L1cm10) and a tetracycline-responsive internal Inverter gate (L2bulgeOff1tc) to stems I and II, respectively, of a ribozyme. Device response under different input conditions (theo or tc(−), 0 mM; theo(+), 10 mM; tc(+), 1 mM) is reported as the difference between expression activity in the presence of both inputs and that at the indicated input conditions.

Devices constructed through SI 2 and 3 consisted of multiple sensor-transmitter components, or internal gates (FIG. 1B). An internal Inverter or Buffer gate is defined as a sensor-transmitter component that activates or inactivates, respectively, a coupled component, such as an actuator or other internal gate, in the presence of input. In SI 2, the internal gates act independently through the linked ribozyme stems and therefore computation is performed through the integration of individual internal gate operations in the ribozyme core. The single ribozyme is only in the active state, corresponding to low device output, when both sensor-transmitter components are in states that activate the coupled ribozyme. Applicants constructed a NAND gate by coupling a theophylline-responsive internal Inverter gate through stem I and a tetracycline-responsive internal Inverter gate (FIG. 6) through stem II (SI 2.1; FIG. 3A). The device exhibited low output only in the presence of both inputs, as both internal Inverter gates favored the ribozyme-active state (FIG. 3B and FIG. 9). Other logic operations can be performed by SI 2 devices, such as an OR operation through the coupling of two internal Buffer gates (Example 5).

Figure 10:
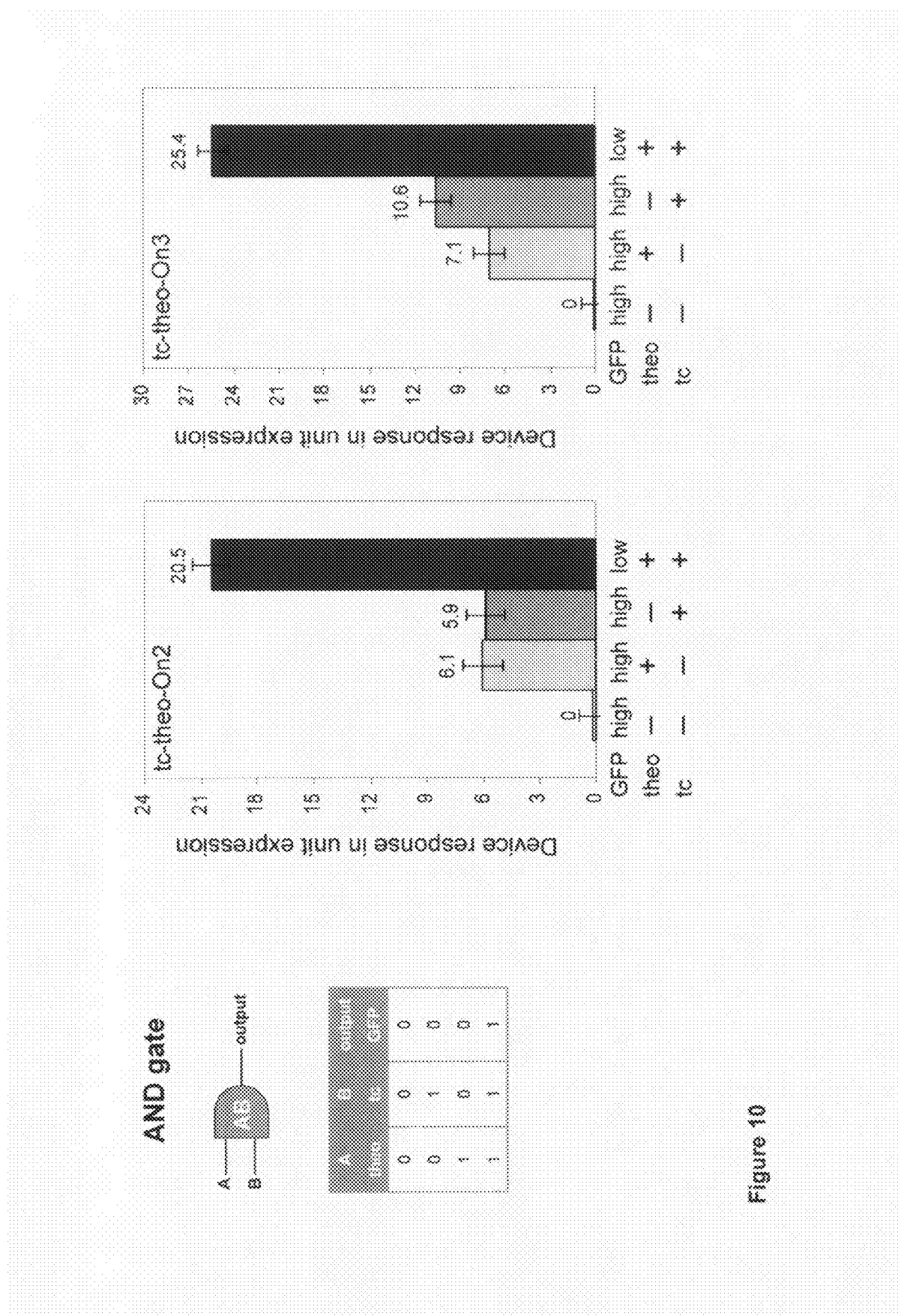
FIG. 10 is the device response and truth table of AND gates (tc-theo-On2 and tc-theo-On3) based on SI 3.1. The RNA devices are constructed by coupling a theophylline-responsive internal Buffer gate (IG1) and a tetracycline-responsive internal Inverter gate (IG2) to stem II of a ribozyme. Device response under different input conditions (theo or tc(−), 0 mM; theo(+), 2.5 mM; tc(+), 0.5 mM) is reported as the difference between expression activity in the absence of both inputs and that at the indicated input conditions.

In SI 3, the sensor-transmitter components are coupled within a ribozyme stem and computation occurs via the integrated operations of the internal gates. Internal gates were linked through the aptamer loop of the lower gate, IG(n), and the transmitter of the higher gate, IG(n+1). The operation of the higher internal gate determines the state of the lower internal gate, where an internal gate can perform its encoded operation when it is in an active state, and the state of the internal gate linked to the ribozyme (IG1) determines the state of the device. Applicants constructed an alternative AND gate by coupling a theophylline-responsive internal Buffer gate (IG1) and a tetracycline-responsive internal Inverter gate (IG2) at stem II (SI 3.1; FIG. 4A). In this composition, only in the presence of both inputs did IG1 change the state of the RNA device to favor the ribozyme-inactive state, resulting in high device output (FIG. 4B and FIG. 10). Applicants also constructed RNA devices that perform an OR operation through SI 3 (Example 5).

Figure 12:
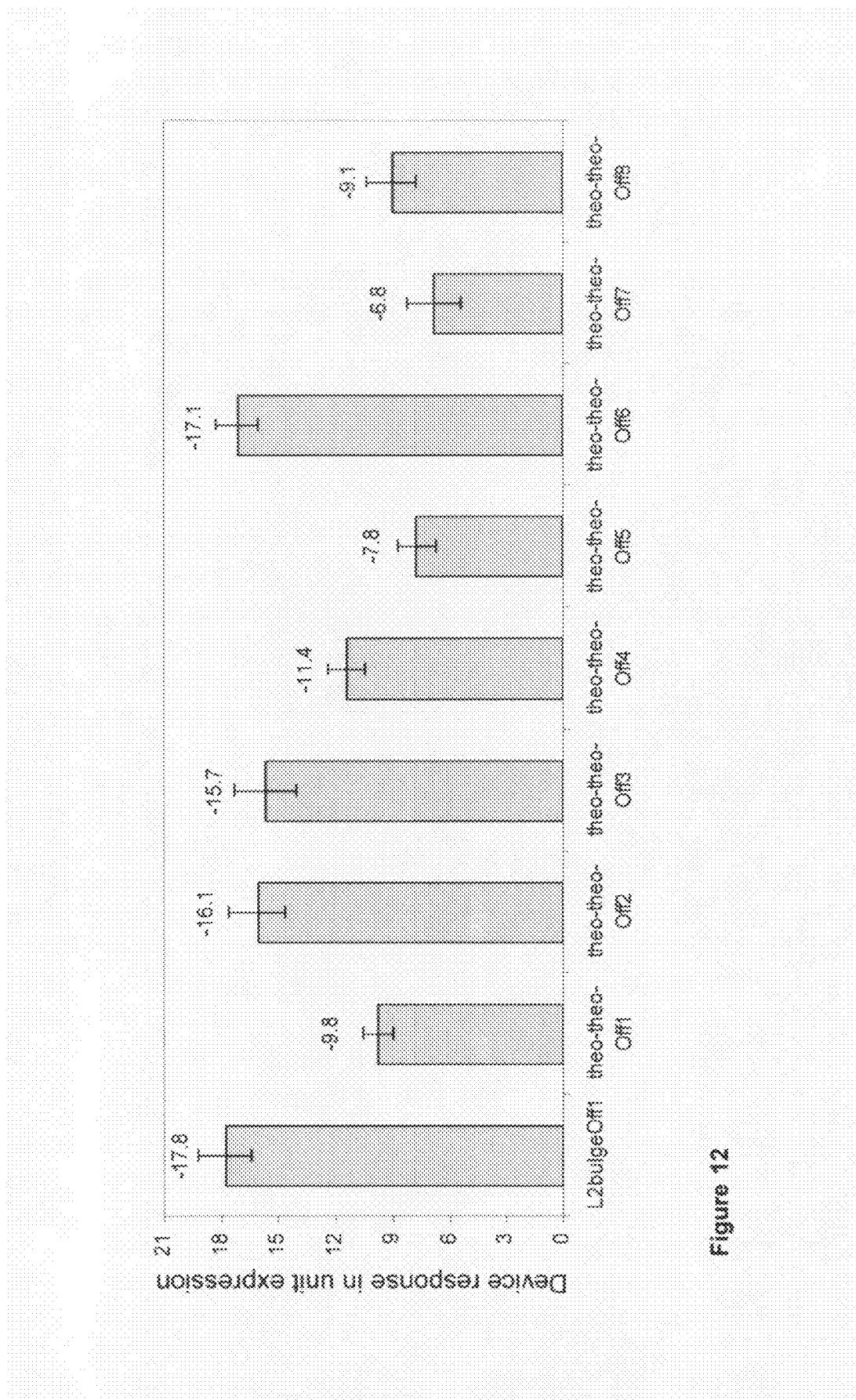
FIG. 12 shows the device response of RNA devices composed of two internal Inverter gates and their single-internal gate device counterpart (L2bulgeOff1). The RNA devices are constructed by coupling two theophylline-responsive internal Inverter gates (IG1, IG2) to stem II of a ribozyme. Device response is reported as the difference between expression activities in the absence and presence of 10 mM theophylline. The negative sign indicates the down-regulation of target gene expression. While all eight devices performed Inverter operations like L2bulgeOff1, only one (theo-theo-Off6) exhibited a low degree of programmed cooperativity (see FIG. 13).
Figure 13:
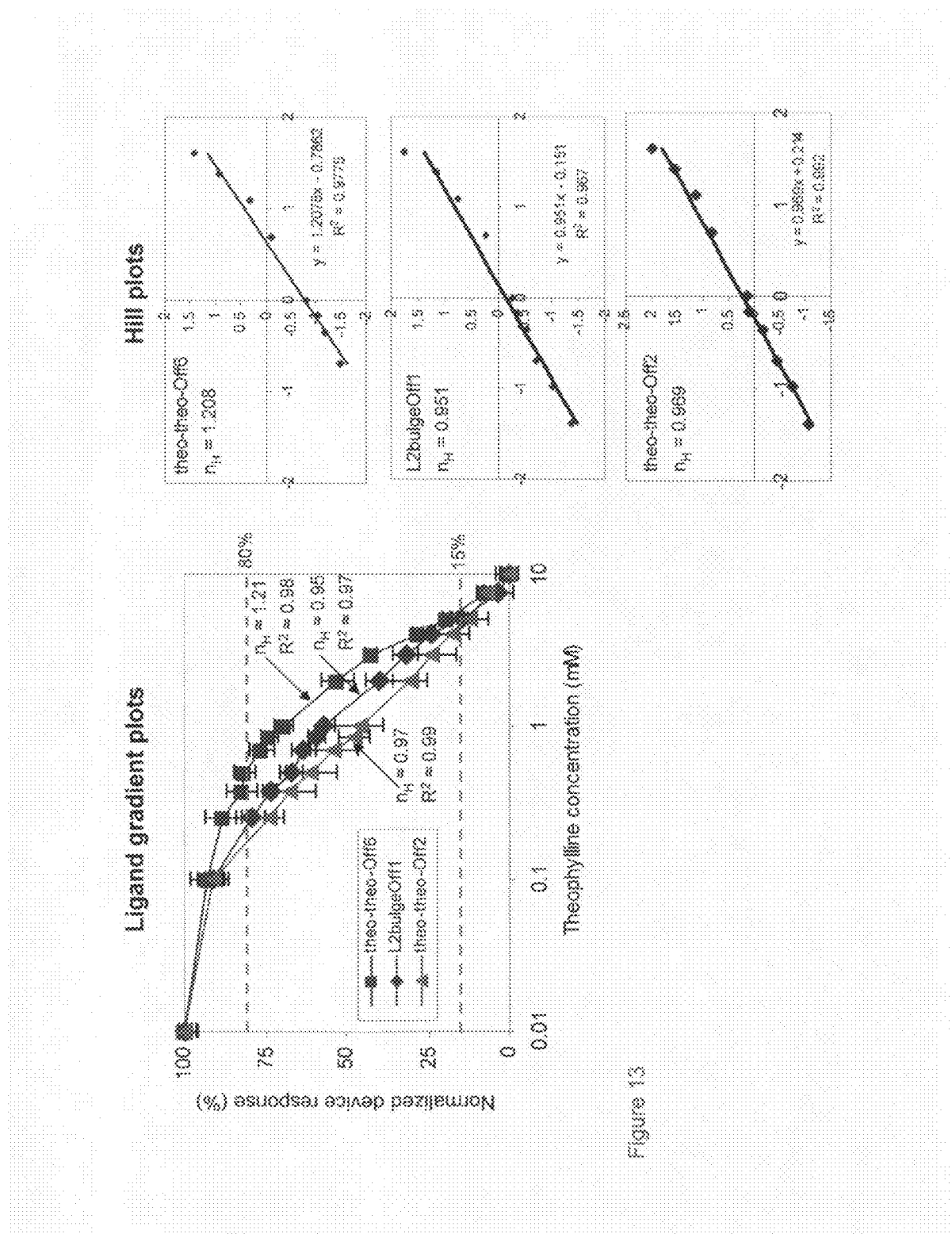
FIG. 13 shows the device response over varying theophylline concentrations of representative RNA devices composed of two internal Inverter gates (theo-theo-Off2, $n_H \approx 1$; theo-theo-Off6, $n_H \approx 1.2$), and their single-internal gate device counterpart (L2bulgeOff1, $n_H \approx 1$). The device response is normalized to the response at 10 mM theophylline. Corresponding Hill plots are constructed for 15-80% of each normalized device response by plotting log [fraction repressed/(1−fraction repressed)] against log [input concentration], where the slope represents the Hill coefficient ($n_H$).
Figure 14:
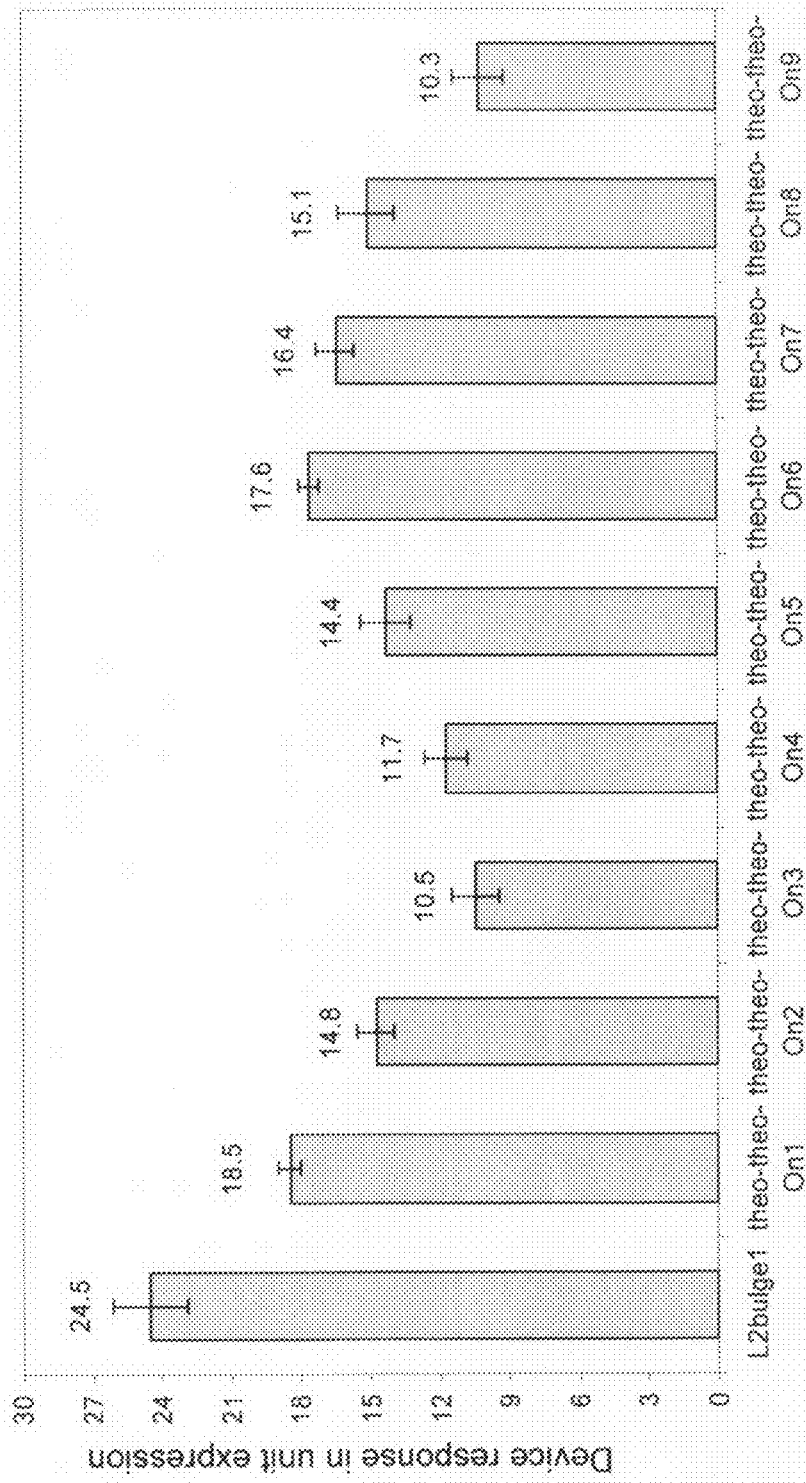
FIG. 14 shows the device response of RNA devices composed of internal Buffer and Inverter gates and their single-internal gate device counterpart (L2bulge1). The RNA devices are constructed by coupling theophylline-responsive internal Buffer (IG1) and Inverter (IG2) gates to stem II of a ribozyme. Device response is reported as the difference between expression activities in the absence and presence of 10 mM theophylline. While all nine devices performed Buffer operations like L2bulge1, none of them exhibited programmed cooperativity where $\Delta\Delta G_{IG1}=0.3$ kcal/mol was used. In contrast, when $\Delta\Delta G_{IG1}$ was increased to 1 kcal/mol, the devices exhibited substantial degrees of cooperativity (see FIG. 4E and FIG. 11), indicating that $\Delta\Delta G_{IG1}$ was important to the observed cooperative response.
Figure 15:
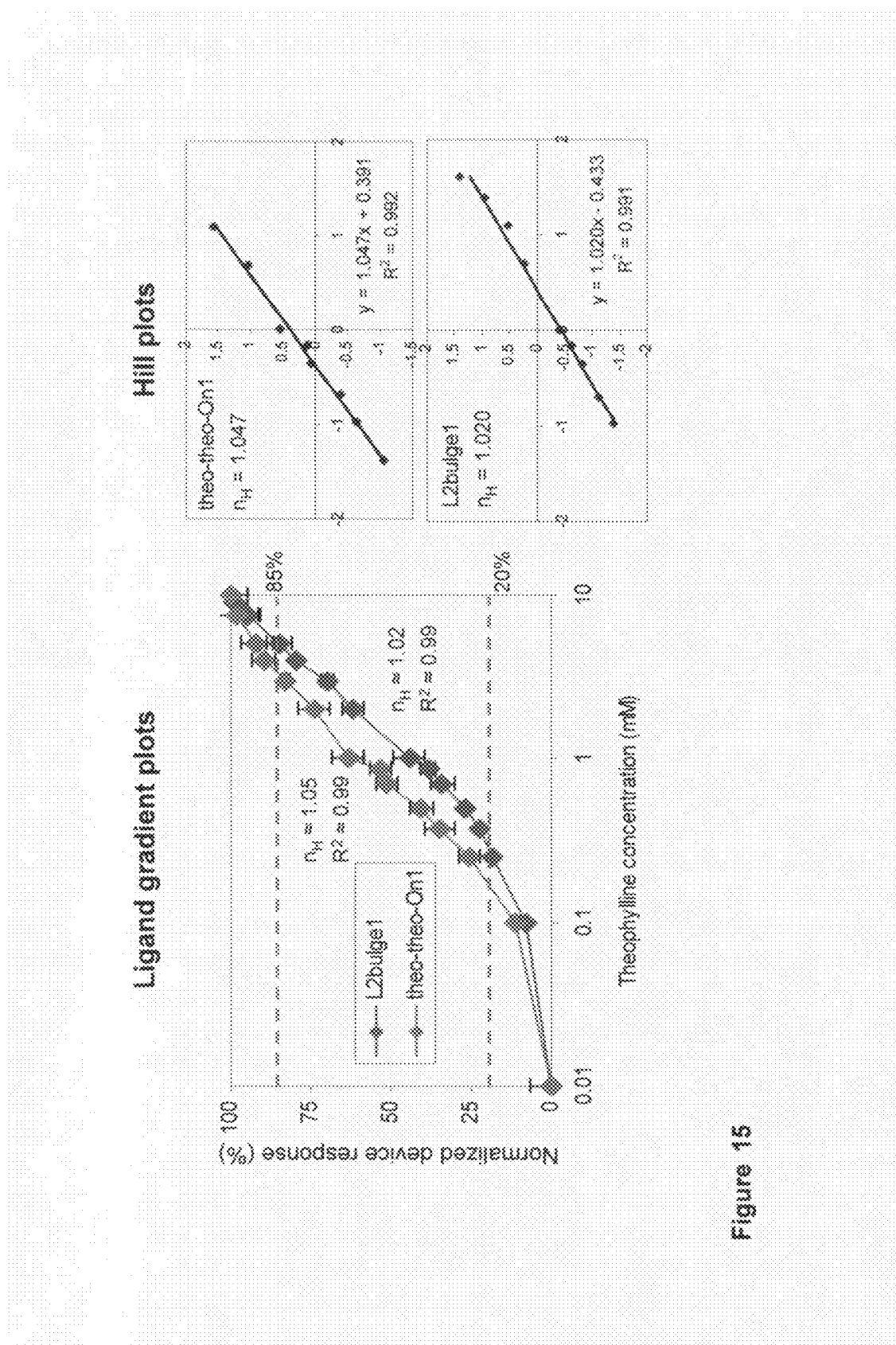
FIG. 15 shows that the device response over varying theophylline concentrations of a representative RNA device composed of internal Buffer and Inverter gates (theo-theo-On1) and its single-internal gate device counterpart (L2bulge1) demonstrates no programmed cooperativity ($n_H \approx 1$). The device response is normalized to the response at 10 mM theophylline. Corresponding Hill plots are constructed for 20-85% of each normalized device response by plotting log [fraction expressed/(1−fraction expressed)] against log [input concentration], where the slope represents the Hill coefficient ($n_H$).
Figure 16:
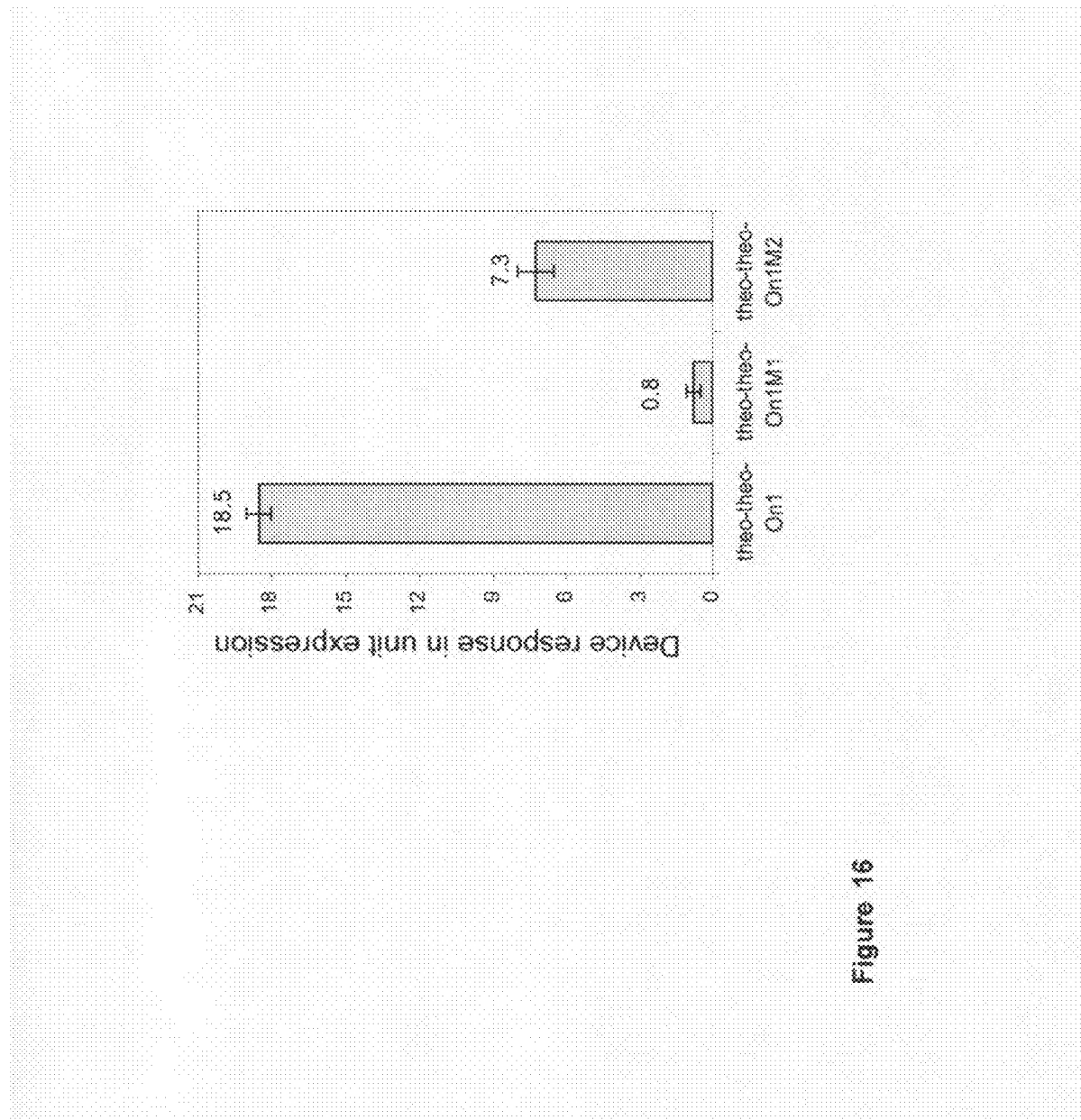
FIG. 16 shows that the device response of a representative RNA device composed of internal Buffer and Inverter gates (theo-theo-On1) and its mutated sensor variants demonstrates that input binding at both internal gates is responsible for the overall device response. Theo-theo-On1M1, mutation to the sensor in IG1; theo-theo-On1M2, mutation to sensor in IG2. Device response is reported as the difference in expression activities in the absence and presence of 10 mM theophylline. Individual mutations in both internal gates exhibited considerably lower output levels, supporting that both internal gates contribute to the overall device response. However, it was observed that theo-theo-On1M2 demonstrated less inhibition of device response compared to theo-theo-On1M1. The mutation of IG1 is anticipated to have a more significant impact on device performance as the device response is directly regulated by IG1.
Figure 17:
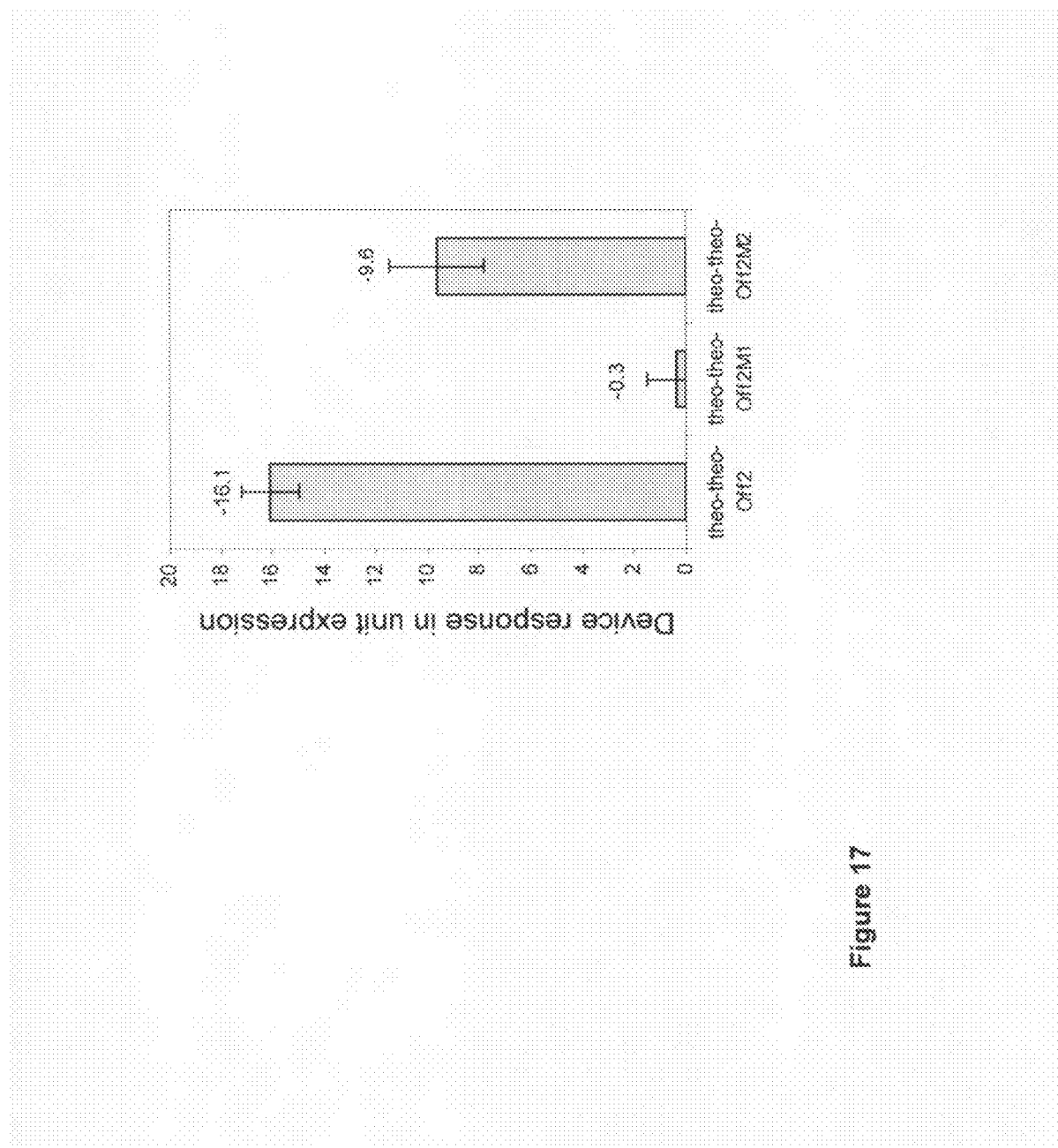
FIG. 17 shows that the device response of a representative RNA device composed of two internal Inverter gates (theo-theo-Off2) and its mutated sensor variants demonstrates that input binding at both internal gates is responsible for the overall device response. Theo-theo-Off2M1, mutation to the sensor in IG1; theo-theo-Off2M2, mutation to sensor in IG2. Device response is reported as the difference in expression activities in the absence and presence of 10 mM theophylline. The negative sign indicates the down-regulation of target gene expression. The mutation of IG1 is anticipated to have a more significant impact on device performance as the device response is directly regulated by IG1.
Figure 18:
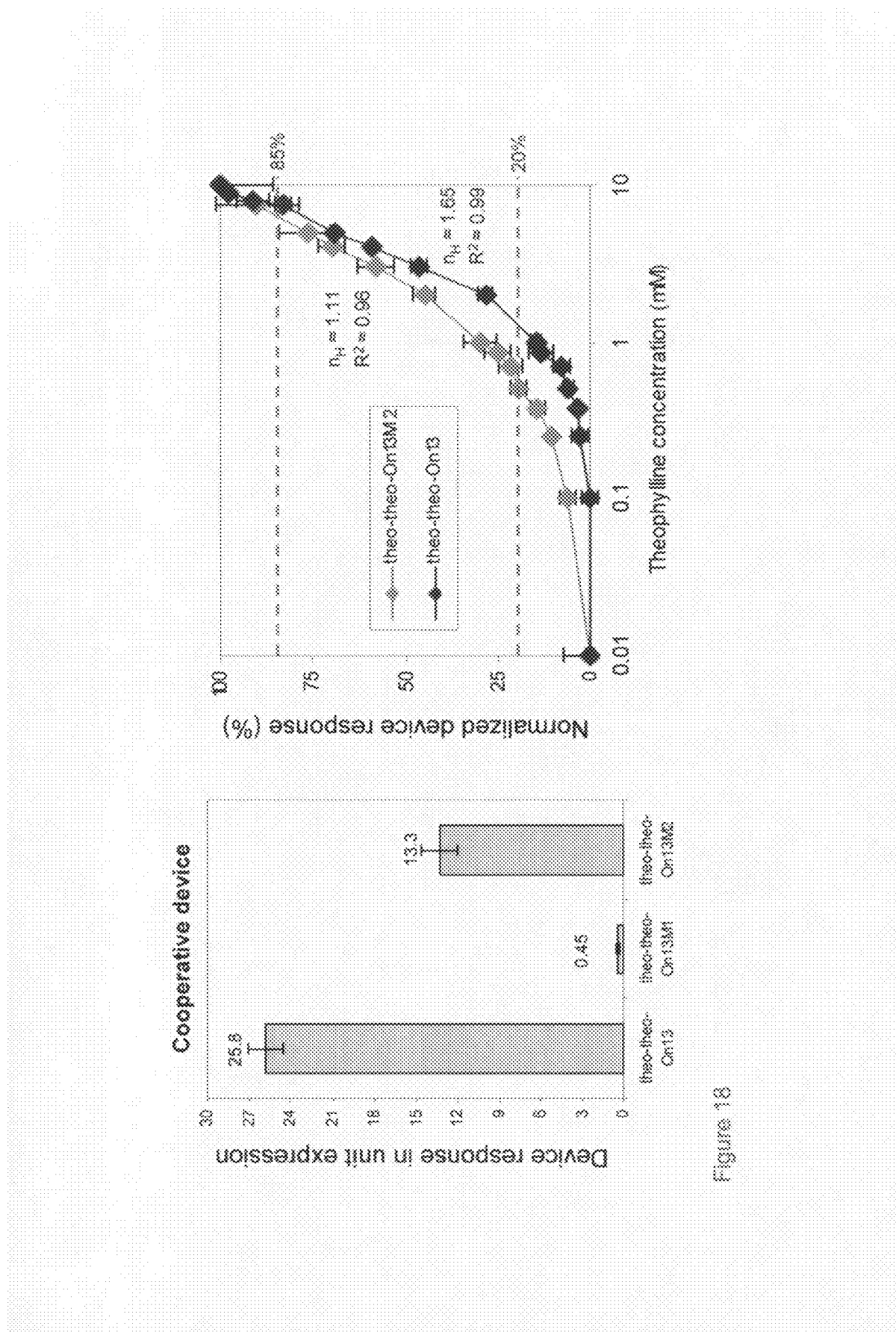
FIG. 18 shows that the device response of a representative RNA device composed of internal Buffer and Inverter gates that exhibits programmed cooperativity (theo-theo-On13) and its mutated sensor variants demonstrates that input binding at both internal gates is responsible for the overall device response. Theo-theo-On13M1, mutation to the sensor in IG1; theo-theo-On13M2, mutation to sensor in IG2. Device response is reported as the difference in expression activities in the absence and presence of 10 mM theophylline. The device response is normalized to the response at 10 mM theophylline. Corresponding Hill plots are constructed for 20-85% of each normalized device response by plotting log [fraction expressed/(1−fraction expressed)] against log [input concentration], where the slope represents the Hill coefficient ($n_H$). The mutation of IG1 is anticipated to have a more significant impact on device performance as the device response is directly regulated by IG1.
Figure 19:
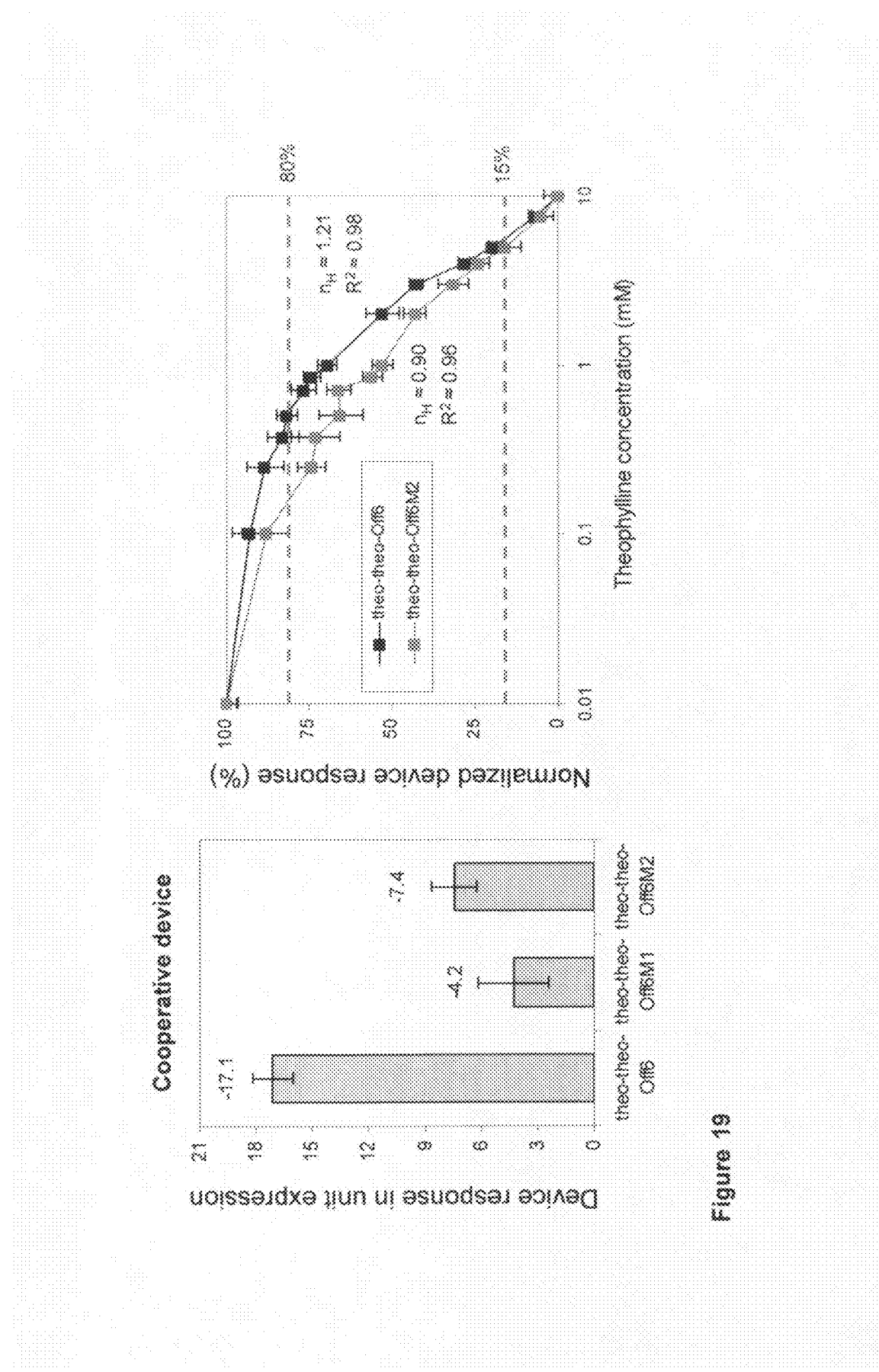
FIG. 19 shows that the device response of a representative RNA device composed of two internal Inverter gates that exhibits programmed cooperativity (theo-theo-Off6) and its mutated sensor variants demonstrates that input binding at both internal gates is responsible for the overall device response. Theo-theo-Off6M1, mutation to the sensor in IG1; theo-theo-Off6M2, mutation to sensor in IG2. Device response is reported as the difference between expression activities in the absence and presence of 10 mM theophylline. The negative sign indicates the down-regulation of target gene expression. The device response is normalized to the response at 10 mM theophylline. Corresponding Hill plots are constructed for 15-80% of each normalized device response by plotting log [fraction repressed/(1−fraction repressed)] against log [input concentration], where the slope represents the Hill coefficient ($n_H$). The mutation of IG6 is anticipated to have a more significant impact on device performance as the device response is directly regulated by IG1.

Applicants engineered RNA devices that exhibited programmed cooperativity through SI 3 by manipulating the relative energies required to switch the device between different states (Example 6). RNA devices were composed of theophylline-responsive internal Buffer (IG1) and Inverter (IG2) gates (SI 3.2; FIG. 4C), in which the energetic differences between the input-unbound (1) and single input-bound (2) states were varied (programmed through IG2; $\Delta\Delta G_{IG2}$; table S2) and the differences between the single input-bound and two input-bound (3) states were kept constant (programmed through IG1; $\Delta\Delta G_{IG1}$=1 kcal/mol). The devices exhibited Buffer operations and substantial degrees of cooperativity (FIG. 4D and FIG. 11), where one device exhibited a degree of cooperativity (Hill coefficient ($n_H$)≈1.65; FIG. 4E) similar to a naturally-occurring cooperative riboswitch (22). Applicants also placed internal Inverter gates into IG1 to construct a device that performed an Inverter operation and exhibited cooperativity (FIGS. 12 and 13). Control studies indicated that the value of $\Delta\Delta G_{IG1}$ was important to the observed cooperative response (FIGS. 14 and 15) and verified that the response was achieved through input binding to both sensors (FIGS. 16-19).

Applicants have developed a composition framework for constructing higher-order RNA devices. Functional modularity is a critical element of any composition framework and achieved in part here through the separation of device functions into distinct components. Although the functions of sensing and actuation frequently rely on tertiary interactions, which are not accounted for in this framework, the integration of these functions into a device is simplified via a transmitter that insulates component functions and controls the interactions between components through predictive hybridization interactions. The variety of information processing operations demonstrated from a small number of standard components emphasizes the utility of modular assembly. In addition, three of the devices have naturally-occurring functional counterparts (22-24), supporting the biological-relevance of such information processing operations. The framework may be further extended to more complex devices by combining multiple SI schemes within a device and implementing layering strategies. Applicants anticipate that further insight into RNA structure-function relationships (25), and improved predictions of RNA secondary and tertiary structures (16), may allow the development of improved modular assembly schemes, in which an important design challenge will be to insulate device functions across distinct components and control interactions between these components.

REFERENCES

1. C. C. Guet, M. B. Elowitz, W. Hsing, S. Leibler, Science 296, 1466 (2002).
2. B. P. Kramer, C. Fischer, M. Fussenegger, Biotechnol Bioeng 87, 478 (2004).
3. R. S. Cox, 3rd, M. G. Surette, M. B. Elowitz, Mol Syst Biol 3, 145 (2007).
4. J. C. Anderson, C. A. Voigt, A. P. Arkin, Mol Syst Biol 3, 133 (2007).
5. G. Seelig, D. Soloveichik, D. Y. Zhang, E. Winfree, Science 314, 1585 (2006).
6. Y. Benenson, B. Gil, U. Ben-Dor, R. Adar, E. Shapiro, Nature 429, 423 (2004).
7. R. M. Dirks, N. A. Pierce, Proc Natl Acad Sci USA 101, 15275 (2004).
8. M. N. Stojanovic, D. Stefanovic, Nat Biotechnol 21, 1069 (2003).
9. R. Penchovsky, R. R. Breaker, Nat Biotechnol 23, 1424 (2005).
10. R. R. Breaker, Curr Opin Biotechnol 13, 31 (2002).

11. M. P. Robertson, A. D. Ellington, Nat Biotechnol 17, 62 (1999).
12. F. J. Isaacs, D. J. Dwyer, J. J. Collins, Nat Biotechnol 24, 545 (2006).
13. B. Suess, J. E. Weigand, RNA Biol 5, 24 (2008).
14. K. Rinaudo et al., Nat Biotechnol 25, 795 (2007).
15. B. D. Brown et al., Nat Biotechnol 25, 1457 (2007).
16. M. Parisien, F. Major, Nature 452, 51 (2008).
17. D. H. Mathews, D. H. Turner, Curr Opin Struct Biol 16, 270 (2006).
18. M. N. Win, C. D. Smolke, Proc Natl Acad Sci USA 104, 14283 (2007).
19. T. Hermann, D. J. Patel, Science 287, 820 (2000).
20. A. Khvorova, A. Lescoute, E. Westhof, S. D. Jayasena, Nat Struct Biol 10, 708 (2003).
21. See Materials and methods section.
22. M. Mandal et al., Science 306, 275 (2004).
23. N. Sudarsan et al., Science 314, 300 (2006).
24. R. Welz, R. R. Breaker, RNA 13, 573 (2007).
25. M. T. Woodside et al., Proc Natl Acad Sci USA 103, 6190 (2006).
26. D. L. Nelson, M. M. Cox, Lehninger Principles of Biochemistry (W. H. Freeman and Company, New York, ed. fourth, 2005), pp. 167-174.

All references cited herein are hereby incorporated by reference in their entirety.

Materials And Methods

Plasmid Construction, Cloning, and Cell Strains

Figure 20:
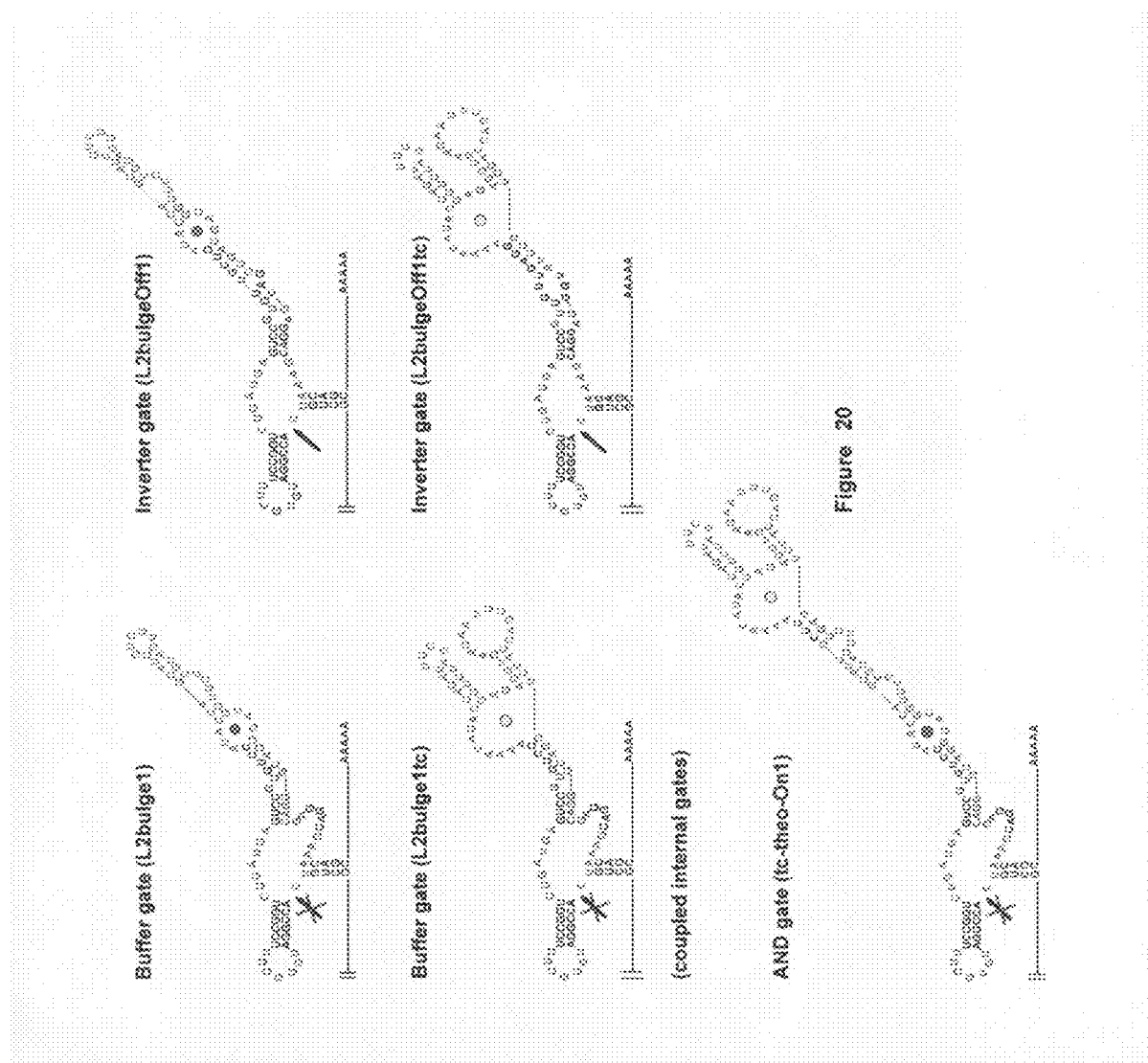
FIG. 20 shows secondary structures and sequences of input-bound states of representative RNA devices. Single-input Buffer gates: L2bulge1 (SEQ ID NO: 1), L2bulge1tc (SEQ ID NO: 3); single-input Inverter gates: L2bulgeOff1 (SEQ ID NO: 2), L2bulgeOff1tc (SEQ ID NO: 4); RNA device composed of internal Buffer (IG1) and Inverter (IG2) gates responsive to different inputs, illustrating points of integration of two sensor-transmitter domains: tc-theo-On1 (SEQ ID NO: 5).
Figure 21:
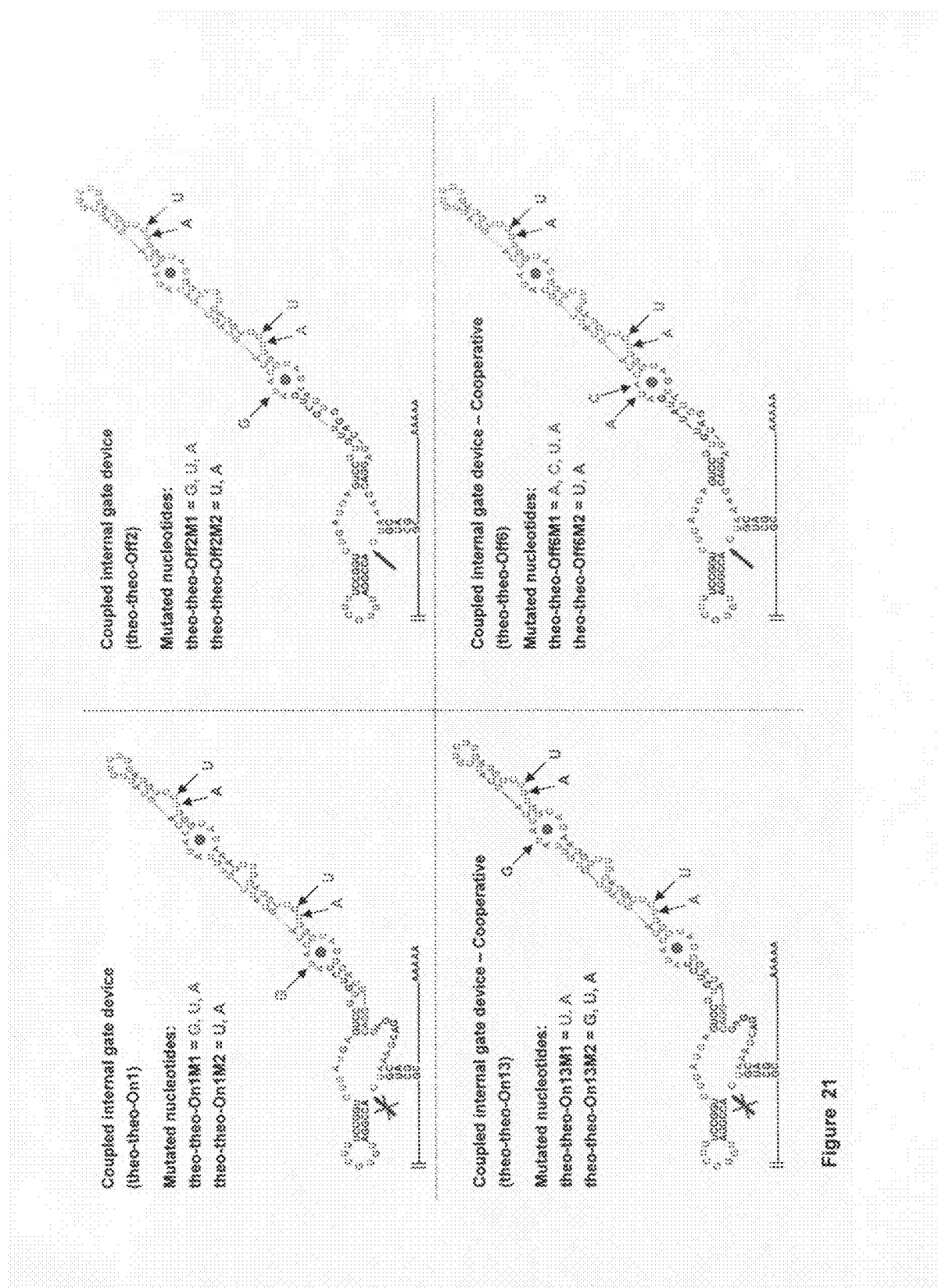
FIG. 21 shows secondary structures and sequences of input-bound states of representative RNA device composed of internal Buffer and Inverter gates responsive to the same input, illustrating points of integration of two sensor-transmitter domains. Nucleotides that were altered in the mutational studies are indicated for the sensors in IG1 and IG2. RNA devices that do not exhibit programmed cooperativity: theo-theo-On1 (SEQ ID NO: 6), theo-theo-Off2 (SEQ ID NO: 7); RNA devices that exhibit programmed cooperativity: theo-theo-On13 (SEQ ID NO: 8), theo-theo-Off6 (SEQ ID NO: 9).

Using standard molecular biology techniques (S1), the plasmid pRzS, harboring the yeast-enhanced green fluorescence protein (yEGFP) (S2) under the control of a GAL 1-10 promoter, was constructed as previously described (S3) and employed as a universal vector for the characterization of all higher-order RNA devices. All RNA device constructs were generated by PCR amplification using the appropriate oligonucleotide templates and primers. All oligonucleotides were synthesized by Integrated DNA Technologies (IDT). Single ribozyme devices (SI 2 and 3) were cloned into two unique restriction sites, AvrII and XhoI, 3 nucleotides downstream of the stop codon of yEGFP and upstream of an ADH1 terminator sequence. For dual ribozyme devices (SI 1), the second single-input gate including spacer sequences was cloned immediately downstream of the first single-input gate in the second restriction site (XhoI). The functions and sequences of all devices are described in Example 7. Representative secondary structures and sequences are illustrated in FIGS. 20 and 21. Cloned plasmids were transformed into an electrocompetent *Escherichia coli* strain, DH10B (Invitrogen) and all constructs were confirmed by subsequent sequencing (Laragen, Inc). Confirmed plasmid constructs were transformed into a *Saccharomyces cerevisiae* strain (W303 MATα his3-11, 15 trp1-1 leu2-3 ura3-1 ade2-1) using standard lithium acetate procedures (S4).

RNA secondary structure prediction, free energy calculation, and corresponding proposed mechanism RNAstructure 4.2 (rna.urmc.rochester dot edu/mastructure.html) was used to predict the secondary structures of all RNA devices and their corresponding thermodynamic properties as previously described (S3). Prediction of the secondary structures of the RNA devices based on SI 1 and 2 has been previously described (S3). RNA sequences that are predicted to adopt at least two stable conformations (ribozyme-active and -inactive) were constructed and characterized for their functional activity.

Our design strategy is based on engineering competitive hybridization events within the transmitter components that enable the devices to distribute between two primary conformations: one in which the ligand-binding pocket is not formed (input cannot bind the sensor), and the other in which the ligand-binding pocket is formed (input can bind the sensor). Input binding shifts the distribution to favor the input-bound conformation as a function of increasing input concentration and is translated to a change in activity of the ribozyme, where a ribozyme-active state results in self-cleavage of the ribozyme. A representative schematic of an Inverter gate is illustrated in FIG. 6. For RNA devices composed of two internal gates linked through a single ribozyme stem (SI 3), RNA sequences that are predicted to adopt generally at least three stable conformations of interest (FIG. 4, A and C) were constructed and characterized for their functional activity. The device design strategies and their regulatory mechanisms closely follow those described above.

In Vivo Assays for Characterization of RNA Device Properties and Fluorescence Quantification

*S. cerevisiae* cells harboring plasmids carrying appropriate RNA devices were grown in synthetic complete medium supplemented with an appropriate amino acid dropout solution and sugar (2% raffinose, 1% sucrose) overnight at 30° C. (S3). The overnight cell cultures were back-diluted into fresh medium to an $OD_{600}$ of approximately 0.1. At the time of back-dilution, an appropriate volume of galactose (2% final concentration) or an equivalent volume of water were added to the cultures for the induced and non-induced controls, respectively. In addition, an appropriate volume of concentrated input stock dissolved in medium, or an equivalent volume of the medium (no input control) was added to the cultures (to the appropriate final concentration of theophylline, tetracycline, or both inputs, as described in the figure legends). The back-diluted cells were then grown to an $OD_{600}$ of 0.8-1.0 or for a period of approximately 6 hours before measuring output GFP levels on a Cell Lab Quanta SC flow cytometer (Beckman Coulter). Output GFP expression level distributions within the cell populations were measured using the following settings: 488 nm laser line, 525 nm bandpass filter, and a PMT setting of 5.83. Fluorescence data were collected from 10,000 viable cell counts of each culture sample under low flow rates. A non-induced cell population was used to set a background level, and cells exhibiting fluorescence above this background level are defined as the GFP-expressing cell population. The gene expression activity of a device construct is reported as the mean fluorescence value of the gated GFP-expressing cell population.

Characterization of Device Higher-Order Information Processing Properties

Device responses are reported as the arithmetic difference between the gene expression activities of a construct in the absence and presence of the appropriate molecular inputs in fluorescence units of expression, unless otherwise indicated. One unit expression was defined as the gene expression activity of the construct carrying the parental active ribozyme sTRSV relative to that of the inactive ribozyme sTRSV Contl in the absence of input (S3 and see below for the mathematical description). The expression activity of the sTRSV construct is ~2% of that of the construct carrying the inactive ribozyme control sTRSV Contl or the full transcriptional range of 50 units of expression. The following equations provide the device output data evaluation and presentation schemes used in this work.

$$1 \text{ unit expression } (U_{ex}) = \text{the gene expression activity of the}$$
$$\text{parental active ribozyme } sTRSV \text{ relative}$$
$$\text{to that of the inactive ribozyme } sTRSV$$
$$Contl \text{ in the absence of input}$$
$$= r_0/c_0$$
$$\approx r_L/c_L$$

where r and c represent the expression activities of the active sTRSV and inactive sTRSV Contl ribozyme constructs, respectively, and the subscripts, 0 and L, indicate the absence and presence of the appropriate molecular input(s), respectively.

$$\text{Device signal } (S_d) = \text{the gene expression activity of an } RNA$$
$$\text{device relative to that of } sTRSV \text{ Contl}$$
$$= s/c$$

where s represents the expression activity of the device. To report device signal as a percentage, the device signal ($S_d$) was multiplied with 100%. To report device signal in units of expression, the device signal ($S_d$) was divided by $U_{ex}$. Device response ($R_{d,L}$) is the arithmetic difference between the device signals in the absence and presence of the appropriate molecular input(s) (denoted as $S_{d,0}$ and $S_{d,L}$, respectively) and mathematically represented as $R_{d,L}=S_{d,L}-S_{d,0}$, unless otherwise indicated. In all of the above equations, r, c, and s values were taken from at least three independent experiments.

Cooperative binding activities of RNA devices were determined using the Hill equation:

$$y = y_{max} x^{n_H}/(x^{n_H} + K^{n_H})$$

where y is the gene expression activity at an input concentration x, $y_{max}$ is the maximum gene expression activity or saturation level, and $n_H$ and K represent the Hill coefficient and the ligand concentration at the half maximal response, respectively. Experiments demonstrate that the device responses begin to saturate at 10 mM theophylline, such that Hill coefficients were determined by normalizing the device response to the response at 10 mM theophylline and plotting log [fraction expressed (or repressed)/(1−fraction expressed (or repressed))] versus log [input concentration], where the slope represents the Hill coefficient ($n_H$). All fluorescence data and mean±S.D. are reported from at least three independent experiments.

Example 2

RNA Device Response Properties and Standards in Data Presentation

There has been significant effort directed to the characterization of natural and engineered RNA devices. These efforts have resulted in important descriptions and demonstrations of RNA devices; however, the work is often reported through different metrics and standards. Standard means of reporting the characterized device properties are needed to accurately evaluate, compare, and appreciate the functional properties of the diverse RNA devices that have been developed or will be developed.

Figure 22:
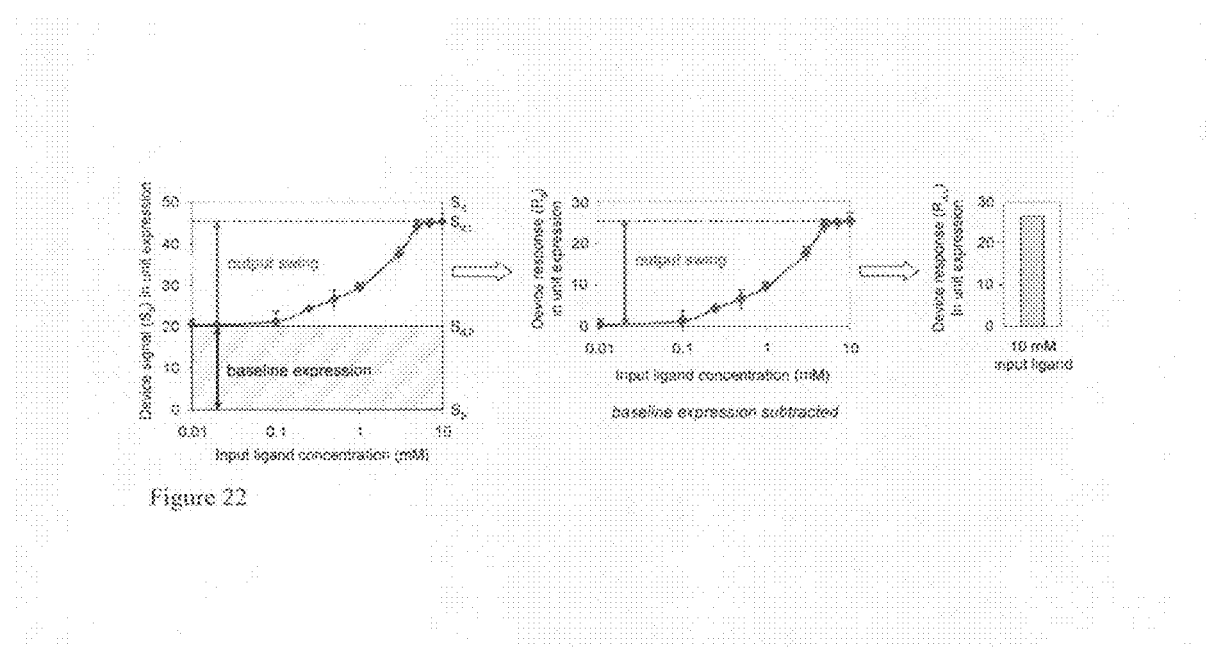
FIG. 22 is a pictorial description of evaluation of device response data.

The RNA device properties that characterize the performance of a device include output swing ($R_d$, absolute difference of the dynamic range; here reported as device response), output fold induction or repression ($S_{d,L}/S_{d,0}$, ratio of the dynamic range), baseline expression ($S_{d,0}$, expression activity in the absence of input ligand; here reported as output basal signal), and input swing (input concentration over which device output changes) (see Materials and Methods and FIG. 22 for details). FIG. 22 provides a pictorial description of how device response data were evaluated in this work. In order to fully characterize the dynamic range of an RNA device, either the baseline expression and the output swing or the baseline expression and the output fold induction (repression) should be reported. However, such dynamic range data cannot be compared across different genetic constructs and systems which can alter the observed response of an RNA device. For example, different organisms will have different transcriptional capacities; different regulated genes will have different fold expression/activity levels (e.g., enzyme-based reporters exhibit turnover of a substrate and an amplified fold induction range relative to fluorescent protein-based reporters); and different promoters will have different fold transcriptional ranges. Therefore, reporting device response properties relative to standards are critical to enabling comparison of the performance of different devices within the context of different genetic constructs and systems.

Here, Applicants used two standards in RNA device characterization: (i) the gene expression activity from the genetic construct (including promoter, gene, etc.) in the absence of the RNA device (100%; signal standard, $S_S$ (Example 2, FIG. 22)), and (ii) the gene expression activity in the absence of the genetic construct (0%; background standard, $S_B$ (FIG. 22). These standards allow one to determine the performance of the RNA device across the full transcriptional range of a specified promoter, without any non-specific effects that an inactive RNA device might exhibit due to its location relative to other components in the genetic construct and its secondary structure. The use of reference standards is important because the RNA device (and therefore its performance) is coupled to other components in the genetic construct, including a promoter. Therefore, components can be changed to alter the baseline expression level relative to the signal standard as appropriate for a given application.

A device architecture that enables modification of baseline expression activities of single-input gates is shown in FIG. 2A, where multiple single-input gates are coupled in a device to alter both the baseline expression and output swing. Applicants selected single-input gates with varying baseline expression activities to demonstrate the effects of gate coupling on baseline expression from the device (FIG. 2B; Example 3). Applicants have previously reported on a tuning strategy targeted to the transmitter component that can be used to build single-input gates with lower baseline expression activities (Buffer 8; ~12%) (3). Therefore, the combination of these two strategies (transmitter tuning and gate coupling) results in devices that exhibit much lower baseline expression activities (2× Buffer 8; ~7%). Applicants report output swing (device response) and baseline expression (device signal in the absence of input) in FIG. 2B to demonstrate the tuning of baseline expression. To simplify data presentation and focus on the response of the RNA devices to inputs, Applicants report only output swing for most of the other devices in the main figures, and report baseline expression activities in Table 1. In addition, another straightforward way to alter the baseline expression from an RNA device is to alter the promoter that it is coupled to. For example, in the systems reported here all devices are coupled to a very strong promoter (GAL1-10). If that promoter is replaced with a weaker promoter, the baseline expression activity would be much lower relative to the signal standard.

With the goal of integrating RNA devices into different genetic circuits (composed of various biological components), such standardized characterization information is critical to match properties of the components in the circuit to achieve the desired system response. RNA devices do not necessarily need to exhibit output swings that span the full transcriptional range of a very strong promoter in order to be biologically relevant. Many endogenous proteins and enzymes are expressed at levels much lower than that obtained from the stronger promoters commonly used in recombinant work. In addition, proteins can exhibit very different thresholds of titratable function depending on their activities, such that a very low baseline expression is not always necessary. Even natural riboswitches may not be used to titrate enzyme concentrations across their full response curves, as that would require cells to regulate input metabolite concentrations to these regulators over a ~$10^4$-$10^5$-fold range. As such, an important property of RNA devices is their ability to be tuned to exhibit different device response properties using (1) energetic tuning strategies targeted to the transmitter component (S3); (2) coupled single-input gates (FIG. 2B); and (3) component matching (S5, S6). These strategies provide important flexibility in tuning RNA device response to fit applications with different performance requirements. Applicants have demonstrated previously that the output swings and baseline expression activities exhibited by RNA devices are biologically relevant, specifically in the application of intracellular detection of metabolic concentrations (where an output swing outside the noise in gene expression is important) and the regulation of cell growth/death (where the ability to titrate the output swing across a threshold concentration of the regulated protein is important) (S3). In addition, there are many other examples where non-coding RNAs play key regulatory roles in controlling biological function without exhibiting regulatory ranges across the full transcriptional range of the promoter system of the genetic construct (S7-S10).

Example 3

Predicted and Observed Response Properties of Coupled Single-Input Gates

Coupled single-input gate devices (SI 1) are composed of single-input gates that are expected to act independently. Independent function of the single-input gates results in several predictions, regarding the response properties of such coupled gate devices relative to the single-input gates. However, the predicted changes in the device response properties were not shown to be exhibited by the naturally-occurring functional counterpart (S11), and are examined here for the synthetic devices.

The first predicted property of a coupled single-input gate device is that it will exhibit decreased basal output signals from the single-input gate. The expected decrease in basal output signal can be predicted from the single-input gate responses and follows a straightforward probability determination that both gates are in the ribozyme-inactive state (requiring AND behavior):

$$p_d = P_1 * p_2$$

where p is the fraction in the ribozyme-inactive state (determined as the gene expression activity relative to that of the ribozyme-inactive control, here reported as device signal); subscripts 1, 2, and d indicate single-input gate 1, single-input gate 2, and the coupled single-input gate device, respectively. The predicted and measured basal output signals are shown in table SI. For most of the coupled single-input gate devices the predicted and measured basal output signals match well, supporting the independent function of the single-input gates. There are two coupled single-input gate devices, both composed of L2cm4, for which there is not a strong match between the predicted and measured values. The results indicate that L2cm4 may not function independently when coupled in a higher-order device. L2cm4 has a transmitter component that functions through a different mechanism than the other single-input gates examined here (S3), specifically through a helix-slipping mechanism (S12). This information transmission mechanism requires the presence of non-Watson-Crick base pairs within the transmitter component, which may result in weaker device structural stability, potentially allowing non-specific interactions with surrounding sequences and thus interfering with the independent function of this single-input gate.

The effect of decreased basal output signal, has also been predicted to result in an increased device response for such systems (S11). This would generally be true under situations in which the input concentration is saturating to the response of the system and irreversible rates do not dominate reversible rates. In the experimental systems examined here, the input ligands may not be at fully saturating concentrations due to transport limitations across the cell membrane and toxicity of the input molecules at high concentrations. In addition, in certain systems the irreversible rate of ribozyme cleavage may compete with the reversible rate of conformational switching.

The second and third predicted properties of coupled single-input gate devices apply to devices that respond to the same inputs (SI 1.1) and apply to the characteristics of the input-response curve. The second property is associated with the sensitivity of the device to input concentration. As previously pointed out, devices that couple Inverter gates (repress gene expression) are predicted to trigger a gene control response at lower input concentrations (S11, S13). This behavior results from such coupled Inverter gate devices functioning essentially through OR behavior, as the independent activation of either single-input gate through input binding results in the repression of gene expression from a transcript. However, devices that couple Buffer gates (activate gene expression) are expected to trigger a gene control response at higher input concentrations, as the independent activation of both gates through input binding (AND behavior) is required to activate gene expression from a transcript.

The third property is associated with the slope of the response curve over ranges in gene expression. Coupled single-input gate devices are predicted to result in a more "digital" response curve (S11), where the same output dynamic range can be achieved with a lower change in input concentration. This effect should be true for both coupled Inverter and Buffer gate devices, although the actual increase in the "digital" nature of the response curve is predicted to be quite low (S11). In addition, this effect would only generally be true under situations in which the input concentration is saturating to the response of the system. For example, at lower input concentrations (i.e., input concentrations lower than the midway point of the input swing), the coupled Inverter gate device is predicted to have a higher slope than the single-input gate, whereas the coupled Buffer gate device is predicted to have a lower slope than the single-input gate. Therefore, the predicted effects on the slope of the response curve are anticipated to be small.

Figure 23:
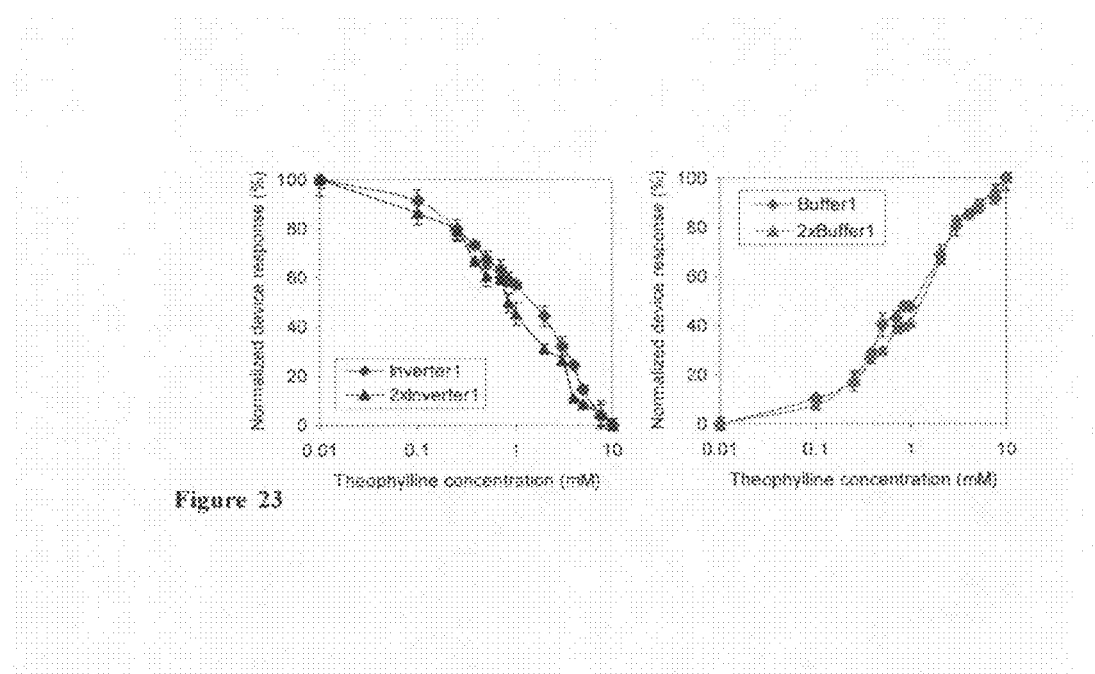
FIG. 23 shows the normalized device response over varying input concentrations of representative coupled gate devices (2×Inverter1, left; 2×Buffer1, right) constructed through SI 1.1 and their corresponding single-gate device counterparts (Inverter1, Buffer1). The device response is normalized to the device response in 10 mM theophylline.

Applicants measured the ligand response curves of two representative coupled single-input gate devices and their single-gate counterparts (FIG. 23). The coupled Inverter gate device (2×Inverter1) exhibited a response at slightly lower concentrations of input than the single Inverter gate (Inverter1), whereas the coupled Buffer gate device (2×Buffer1) exhibited a response at slightly higher concentrations of input than the single Buffer gate (Buffer1). However, the observed changes in the response curves were very slight, such that strong conclusions on the effects of gate coupling on the input-response curves cannot be made.

Example 4

Layered Architectures Extend the Information Processing Capabilities of SI 1

Figure 24:
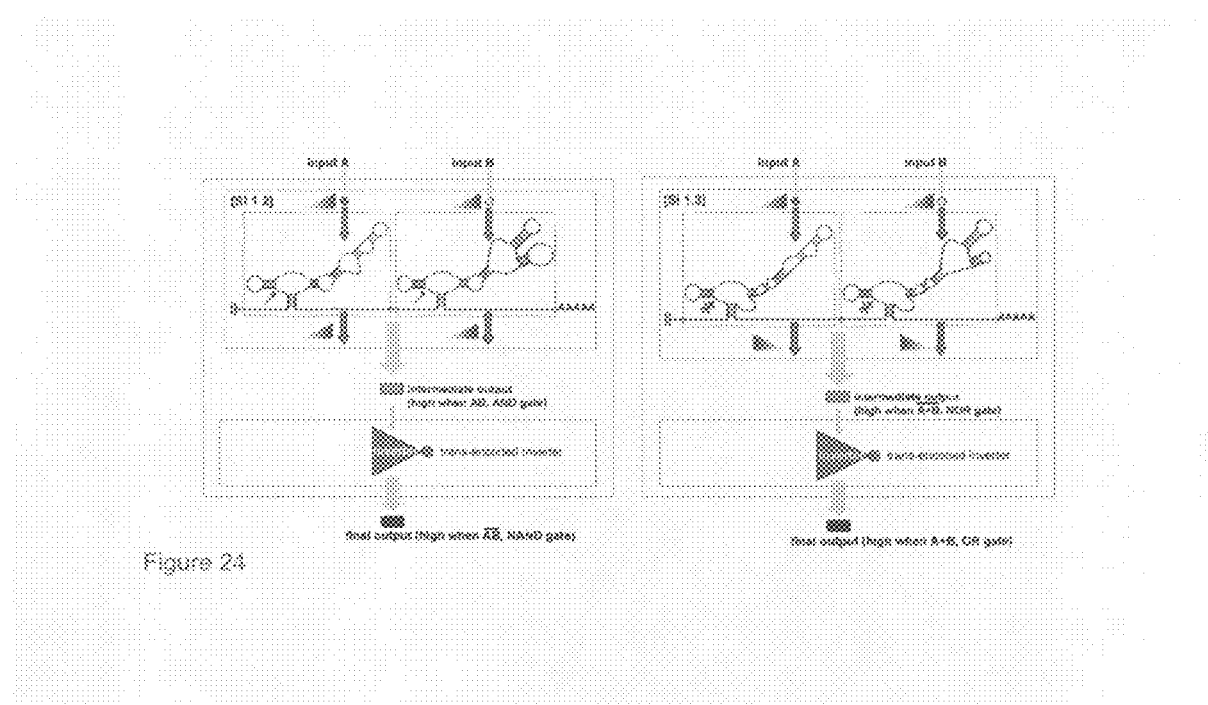
FIG. 24 is a schematic representation of layered architectures that extend the information processing capabilities of SI 1. Left, schematic illustrating a NAND operation by inverting the output of an AND gate. Right, schematic illustrating an OR operation by inverting the output of a NOR gate.

The first assembly scheme based on signal processing/integration within the 3' UTR provides modular composition frameworks for two basic logic operators, AND and NOR gates. Additional logic operators may be desired, including NAND and OR gates. One way in which to directly obtain these logic operations from the assembled operations in SI 1 is to invert the output from the AND and NOR gates, respectively (FIG. 24). For example, the resulting output of the AND and NOR gates can be an Inverter device such as a repressor protein (S14) or an inhibitory noncoding RNA (S15) that acts on a separately encoded gene product resulting in the desired NAND and OR operations, respectively. However, this proposed framework results in a layered architecture, which may have less desirable properties such as loss of signal and longer signal processing times. Alternative assembly strategies for obtaining additional logic operations that result in non-layered architectures are described herein.

Example 5

Non-Layered Architectures (SI 2, SI 3) for an or Operation

The second assembly scheme based on signal processing/integration at the ribozyme core (SI 2) should be as flexible a composition framework as that specified for integration within the 3' UTR (SI 1). For example, SI 2 can be implemented to construct a higher-order RNA device capable of performing an OR operation by coupling internal Buffer gates responsive to different molecular inputs to stems I and II of the ribozyme (SI 2.2, FIG. 25). This device is expected to exhibit low output only in the absence of both inputs, as both internal Buffer gates favor the ribozyme-active state. Therefore, SI 2 can provide logic operations that are not attainable through SI 1 with non-layered architectures.

Alternatively, devices that perform an OR operation were constructed through SI 3 (signal processing/integration through a single ribozyme stem) by coupling a theophylline-responsive internal Buffer gate (IG1) and a tetracycline-responsive internal Inverter gate (IG2) at stem II (FIG. 26A). The assembly scheme is similar to that used to construct devices that perform an AND operation, described in FIG. 4A, except that the energetic requirements for switching between the conformational states were different. This RNA device (SI 3.3) assumed the conformation in which the binding pockets for both inputs are formed (FIG. 26A) with a lower energetic requirement than an AND gate device ($\Delta\Delta G_{IG12}$ in SI 3.3 < $\Delta\Delta G_{IG2}+\Delta\Delta G_{IG1}$ in SI 3.1), effectively allowing either input to bind to its corresponding sensor. In this composition, IG1 changed the state of the RNA device to favor the ribozyme-inactive state in the presence of either input or both, resulting in high device output (FIG. 26B). Applicants constructed two OR gate devices, tc/theo-On1 and tc/theo-On2, based on different IG2 transmitter components.

Example 6

Programming Cooperativity Through Multiple Sensor-Transmitter Components

Cooperativity in biological molecules is often a result of multiple binding sites that transit from a low-affinity state to a high-affinity state as more ligands occupy the available binding sites. In RNA devices composed of two internal gates to the same input, although the sensor components exhibit similar input binding affinities ($K_{apt}$), their effective affinities are a combined effect of the sensor affinity ($K_{apt}$) and the energetic requirements for the device to switch between two states ($K_{IG}$), the latter of which can be programmed into the transmitter component ($\Delta\Delta G_{IG}$). Thus, the difference in free energies between states 1 and 3 ($\Delta\Delta G_{IG2}+\Delta\Delta G_{IG1}$) represents an energetic contribution which lowers the effective binding affinity of IG1 to its input. The difference in free energies between states 1 and 2 ($\Delta\Delta G_{IG2}$) represents a lower energetic contribution to the effective binding affinity of IG2 to its input, such that the effective binding affinity of IG2 is higher than that of IG1. However, binding of input to IG2 lowers the energetic contribution to IG1 to the difference in free energies between states 2 and 3 ($\Delta\Delta G_{IG1}$), resulting in an increase in the effective binding affinity of the device as a result of input binding to IG2. The RNA device design is expected to result in a larger change in the device response as input concentrations increase and IG0 transits from a lower affinity state to a higher affinity state. By programming the energetic differences between the different conformational states ($\Delta\Delta G_{IG2}$ and $\Delta\Delta G_{IG1}$), we can program the degree of cooperativity exhibited by the device (Table 2).

Example 7

Device Sequences

The functions and sequences of all devices used in this work are described in FIG. 27. Formatting schemes in the sequences correspond to those in the schematic device diagrams: black box, catalytic core of the ribozyme or actuator component; gray box, loop regions of the actuator component; outlined, aptamer or sensor component; bold text and dashed underline, strands within the transmitter component that participate in the competitive hybridization event, respectively; gray text, strands within the transmitter component that participate in a helix slipping event; italicized, spacer sequences; double underlined, restriction sites.

TABLE 1

| Device | Device signal (%) (over then full transcriptional range) | | | | Predicted basal signal (%) for coupled devices |
|---|---|---|---|---|---|
| | theo, tc (−) | theo (+) | tc (+) | theo, tc (+) | |
| SI 1.1 | | | | | |
| L2bulge1tc (Buffer-tc) | 37 | | 96 | | |
| 2xL2bulge1tc (2xBuffer-tc) | 16 | | 46 | | 14 |
| L2bulge1 (Buffer1) | 40 | 89 | | | |
| 2xL2bulge1 (2xBuffer1) | 20 | 37 | | | 16 |
| L2bugle8 (Buffer8) | 12 | 48 | | | |
| 2xL2bulge8 (2xBuffer8) | 7 | 19 | | | 1 |
| L2bulge5 (Buffer5) | 82 | 100 | | | |
| L2bulge1 + L2bulge5 (Buffer1 + Buffer5) | 25 | 43 | | | 33 |
| L2bulgeOff1 (Inverter1) | 62 | 26 | | | |
| 2xL2bulgeOff1 (2xInverter1) | 37 | 21 | | | 38 |
| L2cm4 (Inverter4) | 78 | 41 | | | |
| 2xL2cm4 (2xInverter4) | 32 | 20 | | | 61 |
| L2bulgeOff1 + L2cm4 (Inverter1 + Inverter4) | 31 | 17 | | | 48 |
| tc-responsive Inverter gates | | | | | |
| L2bulgeOff1tc (Inverter) | 39 | | 12 | | |
| L2bulgeOff2tc (Inverter) | 42 | | 17 | | |
| L2bulgeOff3tc (Inverter) | 42 | | 17 | | |
| SI 1.2 (AND gate) | | | | | |
| L2bulge1 + L2bulge1tc | 18 | 22 | 24 | 46 | 15 |
| L2bulge9 + L2bulge1tc | 12 | 15 | 16 | 36 | 11 |
| L2bulge9 (single-input Buffer) | 30 | 72 | | | |
| S1 1.3 (NOR gate) | | | | | |
| L2bulgeOff1 + L2bulgeOff1tc | 27 | 15 | 13 | 11 | 24 |
| L2bulgeOff1 + L2bulgeOff2tc | 28 | 18 | 17 | 15 | 26 |
| SI 2.1 (NAND gate) | | | | | |
| L1cm10 + L2bulgeOff3tc | 54 | 52 | 55 | 43 | |
| L1cm10 + L2bulgeOff1tc | 51 | 51 | 50 | 42 | |

| Device | Device signal (%) (over the full transcriptional range) | | | |
|---|---|---|---|---|
| | theo, tc (−) | theo (+) | tc (+) | theo, tc (+) |
| SI 3.1 (AND gate) | | | | |
| tc-theo-On1 | 36 | 48 | 50 | 89 |
| tc-theo-On2 | 39 | 51 | 51 | 80 |
| tc-theo-On3 | 39 | 53 | 61 | 90 |
| SI 3.2 (dual sensor-transmitter) | | | | |
| Buffer function | | | | |
| theo-theo-On1 | 36 | 73 | | |
| theo-theo-On2 | 41 | 70 | | |
| theo-theo-On3 | 54 | 75 | | |
| theo-theo-On4 | 66 | 89 | | |
| theo-theo-On5 | 69 | 98 | | |
| theo-theo-On6 | 46 | 81 | | |
| theo-theo-On7 | 42 | 75 | | |
| theo-theo-On8 | 31 | 61 | | |
| theo-theo-On9 | 23 | 44 | | |
| theo-theo-On10 (cooperative) | 16 | 54 | | |
| theo-theo-On11 (cooperative) | 13 | 55 | | |
| theo-theo-On12 (cooperative) | 12 | 60 | | |
| theo-theo-On13 (cooperative) | 23 | 75 | | |
| Inverter function | | | | |
| theo-theo-Off1 | 34 | 15 | | |
| theo-theo-Off2 | 60 | 27 | | |
| theo-theo-Off3 | 67 | 36 | | |
| theo-theo-Off4 | 47 | 24 | | |
| theo-theo-Off5 | 40 | 24 | | |
| theo-theo-Off6 (cooperative) | 58 | 24 | | |
| theo-theo-Off7 | 54 | 40 | | |
| theo-theo-Off8 | 43 | 24 | | |
| SI 3.3 (OR gate) | | | | |
| tc/theo-On1 | 48 | 65 | 64 | 72 |
| tc/theo-On2 | 42 | 60 | 62 | 71 |

TABLE 2

| Device | $\Delta\Delta G_{IG2}$ (kcal/mol) | $\Delta\Delta G_{IG1}$ (kcal/mol) | Degree of programmed cooperativity |
|---|---|---|---|
| Non-cooperative | | | |
| theo-theo-On1 | 0.3 | 0.3 | none |
| theo-theo-On2 | 2.8 | 0.3 | none |
| theo-theo-On3 | 1.8 | 0.3 | none |
| theo-theo-On4 | 1.9 | 0.3 | none |
| theo-theo-On5 | 0.0 | 0.3 | none |
| theo-theo-On6 | 0.9 | 0.3 | none |
| theo-theo-On7 | 3.0 | 0.3 | none |
| theo-theo-On8 | 2.8 | 0.3 | none |
| theo-theo-On9 | 2.9 | 0.0 | none |
| Cooperative | | | |
| theo-theo-On10 | 0.3 | 1.0 | $n_H \approx 1.32$ |
| theo-theo-On11 | 1 | 1.0 | $n_H \approx 1.63$ |
| theo-theo-On12 | 1.4 | 1.0 | $n_H \approx 1.47$ |
| theo-theo-On13 | 2.2 | 1.0 | $n_H \approx 1.65$ |

Supporting References

S1. J. Sambrook, D. W. Russell, Molecular cloning: a laboratory manual (Cold Spring Harbor Laboratory Press, Cold Spring Harbor, N.Y., ed. 3, 2001).
S2. C. Mateus, S. V. Avery, Yeast 16, 1313 (2000).
S3. M. N. Win, C. D. Smolke, Proc Natl Acad Sci USA 104, 14283 (2007).
S4. R. Gietz, R. Woods, in Guide to Yeast Genetics and Molecular and Cell Biology, Part B, C. Guthrie, G. Fink, Eds. (Academic Press, San Diego, 2002), vol. 350, pp. 87-96.
S5. Y. Yokobayashi, R. Weiss, F. H. Arnold, Proc Natl Acad Sci USA 99, 16587 (2002).
S6. S. Basu, R. Mehreja, S. Thiberge, M. T. Chen, R. Weiss, Proc Natl Acad Sci USA 101, 6355 (2004).
S7. E. Levine, Z. Zhang, T. Kuhlman, T. Hwa, PLoS Biol 5, e229 (2007).
S8. S. S. Hebert et al., Proc Natl Acad Sci USA 105, 6415 (2008).
S9. G. A. Calin et al., Proc Natl Acad Sci USA 105, 5166 (2008).
S10. A. Ventura et al., Cell 132, 875 (2008).
S11. R. Welz, R. R. Breaker, RNA 13, 573 (2007).
S12. G. A. Soukup, G. A. Emilsson, R. R. Breaker, J Mol Biol 298, 623 (2000).
S13. D. A. Rodionov, I. Dubchak, A. Arkin, E. Alm, M. S. Gelfand, Genome Biol 5, R90 (2004).
S14. K. Rinaudo et al., Nat Biotechnol 25, 795 (2007).
S15. T. L. Deans, C. R. Cantor, J. J. Collins, Cell 130, 363 (2007).

We claim:

1. A signal processing device for modulating the expression of a gene product depending on the presence or absence of ligands, the device comprising an RNA comprising:
   (1) a coding sequence for the gene product;
   (2) two or more aptamer-regulated polynucleotides, each said aptamer-regulated polynucleotides comprising at least one aptamer domain and an actuator domain, wherein each of said aptamer domain binds one ligand, and each of said actuator domain(s) has a functional activity that affects the expression of the gene product,
   wherein at least one of said aptamer-regulated polynucleotides further comprises:
   (3) an information transmission domain not overlapping with said actuator domain, said information transmission domain comprising:
      (a) a general transmission region,
      (b) a switching strand,
      (c) a competing strand,
      wherein the switching strand and the competing strand compete to bind to the general transmission region through hybridization interactions,
   wherein binding of said aptamer domains by their respective ligands favors a conformation change in the actuator domain through a strand-displacement mechanism; and, wherein said conformation change modulates said functional activity, thereby affecting the expression of the gene product.

2. The signal processing device of claim 1, wherein the gene product is a protein or a noncoding RNA.

3. The signal processing device of claim 1, wherein the actuator domain for one of said aptamer-regulated polynucleotides is a ribozyme.

4. The signal processing device of claim 1, wherein the actuator domain for one of said aptamer-regulated polynucleotides is a target sequence for siRNA or miRNA.

5. The signal processing device of claim 1, wherein the switching strand and the competing strand are continuous.

6. The signal processing device of claim 1, wherein at least two of said aptamer-regulated polynucleotides bind to different ligands.

7. The signal processing device of claim 1, wherein for each of said aptamer-regulated polynucleotides, independently, binding of its aptamer domain by a ligand favors a conformational change that leads to increased activity in its actuator domain.

8. A signal processing device for modulating the expression of a gene product depending on the presence or absence of ligands, the device comprising an RNA comprising:
   (1) a coding sequence for the gene product;
   (2) two or more aptamer domains and one actuator domain, wherein each of said aptamer domains binds one ligand, and said actuator domain has a functional activity that affects the expression of the gene product, and wherein said two or more aptamer domains are linked to the actuator domain,
   wherein binding of said aptamer domains by their respective ligands favors a conformation change in the actuator domain through a strand-displacement mechanism; and, wherein said conformation change modulates said functional activity, thereby affecting the expression of the gene product.

9. The signal processing device of claim 8, wherein said actuator domain is a cis-acting hammerhead ribozyme comprising a catalytic core and stem I, stem II and stem III duplex regions extending therefrom, said stem I having a loop I single-stranded loop region opposite to said catalytic core, and said stem II having a loop II single-stranded loop region opposite to said catalytic core;
   the signal processing device further comprising two information transmission domains, each having a first and second end and being directly coupled to said loop I or loop II through said first end;

wherein each of said two or more aptamers are coupled to one of said information transmission domains through said second end, each said aptamer binds a ligand, wherein, binding of said ligand to said aptamer favors a conformation change in the ITD such that said ribozyme undergoes self-cleavage of a backbone phosphodiester bond at a rate dependent upon the presence or absence of said ligand.

10. The signal processing device of claim 8, further comprising:
   (3) one or more information transmission domain(s) between said aptamer domains and said actuator domain, each said information transmission domain(s) comprising:
      (a) a general transmission region,
      (b) a switching strand,
      (c) a competing strand,
   wherein the switching strand and the competing strand compete to bind to the general transmission region through hybridization interactions.

11. The signal processing device of claim 1, wherein at least two of said aptamer domains are in tandem, such that one aptamer domain is linked to a single actuator domain.

12. The signal processing device of claim 1, wherein the RNA is a transcription product.

13. A vector or expression construct encoding the signal processing device of claim 1.

14. A method for processing and integrating two or more biological inputs into a processed output, said method comprising:
   (1) providing a signal processing device of claim 1 or 8, wherein each of said aptamer domains binds one ligand, and each of said biological inputs is represented by the presence or absence of a ligand;
   (2) monitoring the expression level and/or activity of the gene product as the processed output.

15. A method for rendering expression of a target gene in a cell dependent on the presence or absence of two or more ligands, comprising introducing into the cell a signal processing device of claim 1 or 8, wherein each said ligand is bound by at least one of said aptamer domains, and wherein said gene product modulates the expression of the target gene.

16. The method of claim 15, wherein said gene product is a transcriptional repressor that inhibits the expression of the target gene.

17. The method of claim 15, wherein said gene product is a transcriptional activator that increases the expression of the target gene.

18. A method for causing phenotypic regulation of cell growth, differentiation or viability in cells of a patient, comprising introducing into cells in said patient a signal processing device of claim 1 or 8, where said aptamer domains bind to one or more ligands, the concentrations of which ligands are dependent on cellular phenotype, wherein binding of said ligands to said aptamer domains modulates expression of the gene product which inhibits or activates a target gene essential for altering the regulation of cell growth, differentiation or viability in said cells.

19. A pharmaceutical preparation comprising a signal processing device of claim 1 or 8, or an expression construct which, when transcribed, produces said signal processing device, and a pharmaceutically acceptable carrier suitable for administering to a human or non-human patient.

20. A vector or expression construct encoding the signal processing device of claim 8.

21. A cell engineered to include the signal processing device of claim 1 or 8, or the vector or expression construct of claim 13 or 20.

22. A method for regulating expression of a target gene, comprising:
   (i) providing a cell of claim 21, wherein the gene product is a transcription activator or repressor of the target gene, or a non-coding RNA inhibitor of the target gene,
   (ii) contacting the cell with one or more ligands that bind said two or more aptamer domains, thereby affecting the expression of the gene product and the expression of the target gene.

23. The signal processing device of claim 1, wherein the device is incorporated into 3'-UTR of the coding sequence.

24. The signal processing device of claim 8, wherein the device is incorporated into 3'-UTR of the coding sequence.

25. The signal processing device of claim 8, wherein the actuator domain is a ribozyme.

26. The signal processing device of claim 8, wherein the actuator domain is a target sequence for siRNA or miRNA.

* * * * *

SEQUENCE LISTING

```
<160> NUMBER OF SEQ ID NOS: 63

<210> SEQ ID NO 1
<211> LENGTH: 100
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gcugucaccg gaugugcuuu ccggucugau gaguccgugu ccauaccagc aucgucuuga      60
ugcccuuggc agggacggga cgaggacgaa acagcaaaaa                          100

<210> SEQ ID NO 2
<211> LENGTH: 102
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gcugucaccg gaugugcuuu ccggucugau gaguccgugu ugcugauacc agcaucgucu      60
ugaugcccuu ggcagcagug gacgaggacg aaacagcaaa aa                       102

<210> SEQ ID NO 3
<211> LENGTH: 117
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gcugucaccg gaugugcuuu ccggucugau gaguccgugu ccaaaacaua ccagauuucg      60
aucuggagag gugaagaauu cgaccaccug gacgggacga ggacgaaaca gcaaaaa       117
```

```
<210> SEQ ID NO 4
<211> LENGTH: 120
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gcugucaccg gaugugcuuu ccggucugau gaguccguug uugaggaaaa cauaccagau    60
uucgaucugg agaggugaag aauucgacca ccuccuuaug ggaggacgaa acagcaaaaa   120

<210> SEQ ID NO 5
<211> LENGTH: 153
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gcugucaccg gaugugcuuu ccggucugau gaguccgugu ccauaccagc aucgcucaaa    60
acauaccaga uuucgaucug gagaggugaa gaauucgacc accugagucu ugaugcccuu   120
ggcagggacg ggacgaggac gaaacagcaa aaa                                153

<210> SEQ ID NO 6
<211> LENGTH: 136
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gcugucaccg gaugugcuuu ccggucugau gaguccgugu ccauaccagc aucguuuaua    60
ccagcaucgu cuugaugccc uuggcagaaa ucuugaugcc cuuggcaggg acgggacgag   120
gacgaaacag caaaaa                                                   136

<210> SEQ ID NO 7
<211> LENGTH: 136
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcugucaccg gaugugcuuu ccggucugau gaguccgugu ugcugauacc agcaucgaca    60
uaccagcauc gucuugaugc ccuuggcagg uucuugaugc ccuuggcagc aguggacgag   120
gacgaaacag caaaaa                                                   136

<210> SEQ ID NO 8
<211> LENGTH: 138
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gcugucaccg gaugugcuuu ccggucugau gaguccgugu ccauaccagc aucguguuau    60
```
accagcaucg ucuugaugcc cuuggcagaa ugucuugaug cccuuggcag ggauaggacg    120
acgacgaaac agcaaaaa                                                138

<210> SEQ ID NO 9
<211> LENGTH: 134
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gcugucaccg gaugugcuuu ccggucugau gaguccgugu uaugauacca gcaucggcau    60
accagcaucg ucuugaugcc cuuggcaggu ucuugaugcc cuuggcagca uggacgagga    120
cgaaacagca aaa                                                     134

<210> SEQ ID NO 10
<211> LENGTH: 134
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cctaggaaac aaacaaagct gtcaccggat gtgctttccg gtctgatgag tccgtgtcca    60
taccagcatc gtcttgatgc ccttggcagg gacgggacga ggacgaaaca gcaaaagaa    120 aaataaaact cgag                                                    134

<210> SEQ ID NO 11
<211> LENGTH: 136
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cctaggaaac aaacaaagct gtcaccggat gtgctttccg gtctgatgag tccgtgtcca    60
ataccagcat cgtcttgatg cccttggcag tggacgggac gaggacgaaa cagcaaaaag    120
aaaaataaaa ctcgag                                                  136

<210> SEQ ID NO 12
<211> LENGTH: 136
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cctaggaaac aaacaaagct gtcaccggat gtgctttccg gtctgatgag tccgttgtcc    60
ataccagcat cgtcttgatg cccttggcag ggacgggacg gaggacgaaa cagcaaaaag    120
aaaaataaaa ctcgag                                                  136

<210> SEQ ID NO 13
<211> LENGTH: 139
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
cctaggaaac aaacaaagct gtcaccggat gtgctttccg gtctgatgag tccgttgtcc    60
aataccagca tcgtcttgat gcccttggca gtggatgggg acggaggacg aaacagcaaa   120
aagaaaataa aaactcgag                                                139

<210> SEQ ID NO 14
<211> LENGTH: 151
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cctaggaaac aaacaaagct gtcaccggat gtgctttccg gtctgatgag tccgtgtcca    60
aaacatacca gatttcgatc tggagaggtg aagaattcga ccacctggac gggacgagga   120
cgaaacacaa aagaaaaat aaaaactcga g                                   151

<210> SEQ ID NO 15
<211> LENGTH: 136
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cctaggaaac aaacaaagct gtcaccggat gtgctttccg gtctgatgag tccgtgttgc    60
tgataccagc atcgtcttga tgcccttggc agcagtggac gaggacgaaa cagcaaaaag   120
aaaaataaaa ctcgag                                                   136

<210> SEQ ID NO 16
<211> LENGTH: 154
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cctaggaaac aaacaaagct gtcaccggat gtgctttccg gtctgatgag tccgttgttg    60
aggaaaacat accagatttc gatctggaga ggtgaagaat tcgaccacct ccttatggga   120
ggacgaacag caaaagaaa aataaaaact cgag                                154

<210> SEQ ID NO 17
<211> LENGTH: 152
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cctaggaaac aaacaaagct gtcaccggat gtgctttccg gtctgatgag tccgtatgag    60
gaaaacatac cagatttcga tctggagagg tgaagaattc gaccacctcc ttagaggagg   120
acgaaacgca aaagaaaaa taaaaactcg ag                                  152

```
<210> SEQ ID NO 18
<211> LENGTH: 154
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cctaggaaac aaacaaagct gtcaccggat gtgctttccg gtctgatgag tccgttgatg    60
aggaaaacat accagatttc gatctggaga ggtgaagaat tcgaccacct ccttagagga   120
ggacgaacag caaaaagaaa aataaaaact cgag                               154

<210> SEQ ID NO 19
<211> LENGTH: 131
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cctaggaaac aaacaaagct gtcaccggat gtgctttccg gtctgatgag tccgtcctgg    60
ataccagcat cgtcttgatg cccttggcag tcatagagga cgaaacagca aaagaaaaa   120 taaaaaccga g                                                       131

<210> SEQ ID NO 20
<211> LENGTH: 130
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cctaggaaac aaacaaagct gtcaccggat gtaaatgata ccagcatcgt cttgatgccc    60
ttggcagctg cgctttccgg tctgatgagt ccgtgaggac gaaacagcaa aagaaaaat   120 aaaaactgag                                                         130

<210> SEQ ID NO 21
<211> LENGTH: 262
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cctaggaaac aaacaaagct gtcaccggat gtgctttccg gtctgatgag tccgtgtcca    60
taccagcatc gtcttgatgc ccttggcagg gacgggacga ggacgaaaca gcaaaaagaa   120 aaataaaaact cgagaaacaa acaaagctgt caccggatgt gctttccggt ctgatgagtc   180
cgtgtccata ccagcatcgt cttgatgccc ttggcaggga cgggacgagg acgaaacagc   240
aaaaagaaaa ataaaaactcg ag                                           262

<210> SEQ ID NO 22
<211> LENGTH: 266
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 22

```
cctaggaaac aaacaaagct gtcaccggat gtgctttccg gtctgatgag tccgtgttgc    60
tgataccagc atcgtcttga tgcccttggc agcagtggac gaggacgaaa cagcaaaaag   120
aaaaataaaa ctcgagaaac aaacaaagct gtcaccggat gtgctttccg gtctgatgag   180
tccgtgttgc tgataccagc atcgtcttga tgcccttggc agcagtggac gaggacgaaa   240
cagcaaaaag aaaataaaaa ctcgag                                         266
```

<210> SEQ ID NO 23
<211> LENGTH: 279
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23

```
cctaggaaac aaacaaagct gtcaccggat gtgctttccg gtctgatgag tccgtgtcca    60
taccagcatc gtcttgatgc ccttggcagg gacgggacga ggacgaaaca gcaaaaagaa   120
aaataaaact cgagaaacaa acaaagctgt caccggatgt gctttccggt ctgatgagtc   180
cgtgtccaaa acataccaga tttcgatctg gagaggtgaa gaattcgacc acctggacgg   240
gacgaggacg aaacgcaaaa agaaaaataa aaactcgag                          279
```

<210> SEQ ID NO 24
<211> LENGTH: 284
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24

```
cctaggaaac aaacaaagct gtcaccggat gtgctttccg gtctgatgag tccgttgtcc    60
aataccagca tcgtcttgat gcccttggca gtggatgggg acggaggacg aaacagcaaa   120
aagaaaataa aaactcgaga aacaaacaaa gctgtcaccg gatgtgcttt ccggtctgat   180
gagtccgtgt ccaaaacata ccagatttcg atctggagag gtgaagaatt cgaccacctg   240
gacgggacga ggacaaacag caaaaagaaa ataaaaact cgag                     284
```

<210> SEQ ID NO 25
<211> LENGTH: 284
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25

```
cctaggaaac aaacaaagct gtcaccggat gtgctttccg gtctgatgag tccgtgttgc    60
tgataccagc atcgtcttga tgcccttggc agcagtggac gaggacgaaa cagcaaaaag   120
aaaaataaaa ctcgagaaac aaacaaagct gtcaccggat gtgctttccg gtctgatgag   180
tccgttgttg aggaaaacat accagatttc gatctggaga ggtgaagaat cgaccacct   240 ccttatggga ggacaaacag caaaagaaa aataaaaact cgag                     284
```

<210> SEQ ID NO 26
<211> LENGTH: 282

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cctaggaaac aaacaaagct gtcaccggat gtgctttccg gtctgatgag tccgtgttgc     60
tgataccagc atcgtcttga tgcccttggc agcagtggac gaggacgaaa cagcaaaaag    120
aaaaataaaa ctcgagaaac aaacaaagct gtcaccggat gtgctttccg gtctgatgag    180
tccgtatgag gaaaacatac cagatttcga tctggagagg tgaagaattc gaccacctcc    240
ttagaggagg acgaacagca aaagaaaaa taaaaactcg ag                        282

<210> SEQ ID NO 27
<211> LENGTH: 264
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctaggaaac aaacaaagct gtcaccggat gtgctttccg gtctgatgag tccgtgtcca     60
taccagcatc gtcttgatgc ccttggcagg gacgggacga ggacgaaaca gcaaaaagaa    120
aaataaaact cgagaaacaa acaaagctgt caccggatgt gctttccggt ctgatgagtc    180
cgtgttgctg ataccagcat cgtcttgatg cccttggcag cagtggacga ggacgaaaca    240
gcaaaaagaa aataaaaact cgag                                           264

<210> SEQ ID NO 28
<211> LENGTH: 193
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cctaggaaac aaacaaagct gtcaccggat gtaaatgata ccagcatcgt cttgatgccc     60
ttggcagctg cgctttccgg tctgatgagt ccgttgttga ggaaaacata ccagatttcg    120
atctggaagg tgaagaattc gaccacctcc ttatgggagg acgaaacagc aaaagaaaa    180 ataaaaactc gag                                                       193

<210> SEQ ID NO 29
<211> LENGTH: 193
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cctaggaaac aaacaaagct gtcaccggat gtaaatgata ccagcatcgt cttgatgccc     60
ttggcagctg cgctttccgg tctgatgagt ccgttgatga ggaaaacata ccagatttcg    120
atctggaagg tgaagaattc gaccacctcc ttagaggagg acgaaacagc aaaagaaaa    180 ataaaaactc gag                                                       193

<210> SEQ ID NO 30
```

<211> LENGTH: 187
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cctaggaaac aaacaaagct gtcaccggat gtgctttccg gtctgatgag tccgtgtcca    60
taccagcatc gctcaaaaca taccagattt cgatctggag aggtgaagaa ttcgaccacc    120
tgagtctgat gcccttggca gggacgggac gaggacgaaa cagcaaaaag aaaaataaaa    180
actcgag    187

<210> SEQ ID NO 31
<211> LENGTH: 185
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cctaggaaac aaacaaagct gtcaccggat gtgctttccg gtctgatgag tccgtgtcca    60
taccagcatc gctaaaacat accagatttc gatctggaga ggtgaagaat tcgaccacct    120
agtcttgtgc ccttggcagg gacgggacga ggacgaaaca gcaaaagaa aataaaaac    180 tcgag    185

<210> SEQ ID NO 32
<211> LENGTH: 187
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cctaggaaac aaacaaagct gtcaccggat gtgctttccg gtctgatgag tccgtgtcca    60
taccagcatc gtgtaaaaca taccagattt cgatctggag aggtgaagaa ttcgaccacc    120
tacatctgat gcccttggca gggacgggac gaggacgaaa cagcaaaaag aaaaataaaa    180
actcgag    187

<210> SEQ ID NO 33
<211> LENGTH: 191
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cctaggaaac aaacaaagct gtcaccggat gtgctttccg gtctgatgag tccgtgtcca    60
taccagcatc gggcctaaaa cataccagat ttcgatctgg agaggtgaag aattcgacca    120
cctaggttct tgatgccctt ggcagggacg ggacgaggac gaaacagcaa aagaaaaat    180 aaaaactcga g    191

<210> SEQ ID NO 34
<211> LENGTH: 191
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 34
cctaggaaac aaacaaagct gtcaccggat gtgctttccg gtctgatgag tccgtgtcca       60
taccagcatc ggtggtaaaa cataccagat ttcgatctgg agaggtgaag aattcgacca      120
cctaccatct tgatgccctt ggcagggacg ggacgaggac gaaacagcaa aagaaaaat      180 aaaaactcga g                                                          191

<210> SEQ ID NO 35
<211> LENGTH: 170
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cctaggaaac aaacaaagct gtcaccggat gtgctttccg gtctgatgag tccgtgtcca       60
taccagcatc gtttatacca gcatcgtctt gatgcccttg gcagaaatct tgatgccctt     120
ggcagggcgg gacgaggacg aaacagcaaa agaaaaata aaaactcgag                  170

<210> SEQ ID NO 36
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cctaggaaac aaacaaagct gtcaccggat gtgctttccg gtctgatgag tccgtgtcca       60
taccagcatc gttgaatacc agcatcgtct tgatgccctt ggcagttgat cttgatgccc     120
ttggcaggac gggacgagga cgaaacagca aaagaaaaa taaaaactcg ag               172

<210> SEQ ID NO 37
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cctaggaaac aaacaaagct gtcaccggat gtgctttccg gtctgatgag tccgtgtcca       60
taccagcatc gattgatacc agcatcgtct tgatgccctt ggcagcagtt cttgatgccc     120
ttggcaggac gggacgagga cgaaacagca aaagaaaaa taaaaactcg ag               172

<210> SEQ ID NO 38
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cctaggaaac aaacaaagct gtcaccggat gtgctttccg gtctgatgag tccgtgtcca       60
taccagcatc gtatgatacc agcatcgtct tgatgccctt ggcagcgtat cttgatgccc     120
```
ttggcaggac gggacgagga cgaaacagca aaaagaaaaa taaaaactcg ag            172

<210> SEQ ID NO 39
<211> LENGTH: 170
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cctaggaaac aaacaaagct gtcaccggat gtgctttccg gtctgatgag tccgtgtcca    60
taccagcatc gatcatacca gcatcgtctt gatgcccttg gcaggattct tgatgccctt   120
ggcagggcgg gacgaggacg aaacagcaaa agaaaaata aaaactcgag               170

<210> SEQ ID NO 40
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cctaggaaac aaacaaagct gtcaccggat gtgctttccg gtctgatgag tccgtgtcca    60
taccagcatc gattgatacc agcatcgtct tgatgccctt ggcagcaatt cttgatgccc   120
ttggcaggac gggacgagga cgaaacagca aaagaaaaa taaaaactcg ag            172

<210> SEQ ID NO 41
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cctaggaaac aaacaaagct gtcaccggat gtgctttccg gtctgatgag tccgtgtcca    60
taccagcatc ggtaaatacc agcatcgtct tgatgccctt ggcagttgct cttgatgccc   120
ttggcaggac gggacgagga cgaaacagca aaagaaaaa taaaaactcg ag            172

<210> SEQ ID NO 42
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cctaggaaac aaacaaagct gtcaccggat gtgctttccg gtctgatgag tccgtgtcca    60
taccagcatc gttgaatacc agcatcgtct tgatgccctt ggcagttgat cttgatgccc   120
ttggcaggac gggacgagga cgaaacagca aaagaaaaa taaaaactcg ag            172

<210> SEQ ID NO 43
<211> LENGTH: 174
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cctaggaaac aaacaaagct gtcaccggat gtgctttccg gtctgatgag tccgtgtcca    60
taccagcatc ggttgaatac cagcatcgtc ttgatgccct tggcagttga ttcttgatgc   120
ccttggcggg acgggacgag gacgaaacag caaaaagaaa aataaaaact cgag         174

<210> SEQ ID NO 44
<211> LENGTH: 174
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cctaggaaac aaacaaagct gtcaccggat gtgctttccg gtctgatgag tccgtgtcca    60
taccagcatc ggttgaatac cagcatcgtc ttgatgccct tggcagttga ctcttgatgc   120
ccttggcggg ataggacgag gacgaaacag caaaaagaaa aataaaaact cgag         174

<210> SEQ ID NO 45
<211> LENGTH: 174
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cctaggaaac aaacaaagct gtcaccggat gtgctttccg gtctgatgag tccgtgtcca    60
taccagcatc ggttgaatac cagcatcgtc ttgatgccct tggcagttga ttcttgatgc   120
ccttggcggg ataggacgag gacgaaacag caaaaagaaa aataaaaact cgag         174

<210> SEQ ID NO 46
<211> LENGTH: 174
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cctaggaaac aaacaaagct gtcaccggat gtgctttccg gtctgatgag tccgtgtcca    60
taccagcatc gattgaatac cagcatcgtc ttgatgccct tggcagttga ttcttgatgc   120
ccttggcggg ataggacgag gacgaaacag caaaaagaaa aataaaaact cgag         174

<210> SEQ ID NO 47
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cctaggaaac aaacaaagct gtcaccggat gtgctttccg gtctgatgag tccgtgtcca    60
taccagcatc gtgttatacc agcatcgtct tgatgccctt ggcagaatgt cttgatgccc   120
ttggcaggat aggacgagga cgaaacagca aaagaaaaa taaaaactcg ag            172

<210> SEQ ID NO 48

```
<211> LENGTH: 168
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cctaggaaac aaacaaagct gtcaccggat gtgctttccg gtctgatgag tccgtgttat      60
gataccagca tcgacatacc agcatcgtct tgatgccctt ggcaggttct tgatgccctt     120
ggcagcagga cgaggacgaa acagcaaaaa gaaaaataaa aactcgag                  168

<210> SEQ ID NO 49
<211> LENGTH: 170
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cctaggaaac aaacaaagct gtcaccggat gtgctttccg gtctgatgag tccgtgttgc      60
tgataccagc atcgacatac cagcatcgtc ttgatgccct tggcaggttc ttgatgccct     120
tggcagcgtg gacgaggacg aaacagcaaa aagaaaaata aaaactcgag                170

<210> SEQ ID NO 50
<211> LENGTH: 170
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cctaggaaac aaacaaagct gtcaccggat gtgctttccg gtctgatgag tccgtgttat      60
gataccagca tcggacatac cagcatcgtc ttgatgccct tggcaggttt cttgatgccc     120
ttggcagatg gacgaggacg aaacagcaaa aagaaaaata aaaactcgag                170

<210> SEQ ID NO 51
<211> LENGTH: 169
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cctaggaaac aaacaaagct gtcaccggat gtgctttccg gtctgatgag tccgtgtgtc      60
tgataccagc atcgacatac cagcatcgtc ttgatgccct tggcaggttc ttgatgccct     120
tggcagcggg acgaggacga aacagcaaaa agaaaaataa aaactcgag                 169

<210> SEQ ID NO 52
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cctaggaaac aaacaaagct gtcaccggat gtgctttccg gtctgatgag tccgtgtgtc      60
```
ctgataccag catcggacat accagcatcg tcttgatgcc cttggcaggt ttcttgatgc    120
ccttggcgca gggacgagga cgaaacagca aaagaaaaa taaaaactcg ag    172

<210> SEQ ID NO 53
<211> LENGTH: 168
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cctaggaaac aaacaaagct gtcaccggat gtgctttccg gtctgatgag tccgtgttat    60
gataccagca tcggcatacc agcatcgtct tgatgccctt ggcaggttct tgatgccctt   120
ggcagcagga cgaggacgaa acagcaaaaa gaaaataaa aactcgag    168

<210> SEQ ID NO 54
<211> LENGTH: 169
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cctaggaaac aaacaaagct gtcaccggat gtgctttccg gtctgatgag tccgtgttgc    60
tgataccagc atcgacatac cagcatcgtc ttgatgccct tggcaggttc ttgatgccct   120
tggcagcggg acgaggacga aacagcaaaa agaaaaataa aaactcgag    169

<210> SEQ ID NO 55
<211> LENGTH: 169
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cctaggaaac aaacaaagct gtcaccggat gtgctttccg gtctgatgag tccgtgtgtt    60
tgataccagc atcgacatac cagcatcgtc ttgatgccct tggcaggttc ttgatgccct   120
tggcagcagg acgaggacga aacagcaaaa agaaaaataa aaactcgag    169

<210> SEQ ID NO 56
<211> LENGTH: 170
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cctaggaaac aaacaaagct gtcaccggat gtgctttccg gtctgatgag tccgtgtcca    60
gaccagcatc gtttatacca gcatcgtctt gatgcccttg gcagaaatct tgatgcctat   120
ggcagggcgg gacgaggacg aaacagcaaa agaaaaata aaaactcgag    170

<210> SEQ ID NO 57
<211> LENGTH: 170
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
cctaggaaac aaacaaagct gtcaccggat gtgctttccg gtctgatgag tccgtgtcca      60
taccagcatc gtttatacca gcatcgtctt gatgcctatg cagaaatct tgatgccctt      120 ggcagggcgg gacgaggacg aaacagcaaa aagaaaaata aaaactcgag               170

<210> SEQ ID NO 58
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cctaggaaac aaacaaagct gtcaccggat gtgctttccg gtctgatgag tccgtgtcca      60
taccagcatc gtgttatacc agcatcgtct tgatgccctt ggcagaatgt cttgatgcct     120
atggcaggat aggacgagga cgaaacagca aaagaaaaa taaaaactcg ag              172

<210> SEQ ID NO 59
<211> LENGTH: 172
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cctaggaaac aaacaaagct gtcaccggat gtgctttccg gtctgatgag tccgtgtcca      60
taccagcatc gtgttagacc agcatcgtct tgatgcctat ggcagaatgt cttgatgccc     120
ttggcaggat aggacgagga cgaaacagca aaagaaaaa taaaaactcg ag              172

<210> SEQ ID NO 60
<211> LENGTH: 170
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cctaggaaac aaacaaagct gtcaccggat gtgctttccg gtctgatgag tccgtgttgc      60
tgagaccagc atcgacatac cagcatcgtc ttgatgccct tggcaggttc ttgatgccta    120
tggcagcgtg gacgaggacg aaacagcaaa aagaaaaata aaaactcgag               170

<210> SEQ ID NO 61
<211> LENGTH: 170
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cctaggaaac aaacaaagct gtcaccggat gtgctttccg gtctgatgag tccgtgttgc      60
tgataccagc atcgacatac cagcatcgtc ttgatgccta tggcaggttc ttgatgccct    120
tggcagcgtg gacgaggacg aaacagcaaa aagaaaaata aaaactcgag               170

-continued

```
<210> SEQ ID NO 62
<211> LENGTH: 168
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cctaggaaac aaacaaagct gtcaccggat gtgctttccg gtctgatgag tccgtgttat        60
gaacccagca tcggcatacc agcatcgtct tgatgccctt ggcaggttct tgatgcctat       120
ggcagcagga cgaggacgaa acagcaaaaa gaaaaataaa aactcgag                    168

<210> SEQ ID NO 63
<211> LENGTH: 168
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cctaggaaac aaacaaagct gtcaccggat gtgctttccg gtctgatgag tccgtgttat        60
gataccagca tcggcatacc agcatcgtct tgatgcctat ggcaggttct tgatgccctt       120
ggcagcagga cgaggacgaa acagcaaaaa gaaaaataaa aactcgag                    168
```